(12) United States Patent
Shluzas et al.

(10) Patent No.: US 10,912,894 B2
(45) Date of Patent: Feb. 9, 2021

(54) CARTRIDGE SAFETY INJECTION SYSTEM AND METHODS

(71) Applicant: Credence MedSystems, Inc., Menlo Park, CA (US)

(72) Inventors: Alan E. Shluzas, San Carlos, CA (US); Mina M. Leung, Mountain View, CA (US); Stephen H. Diaz, Palo Alto, CA (US); Jeff Tillack, Foster City, CA (US)

(73) Assignee: CREDENCE MEDSYSTEMS, INC., Menlo Park, CA (US)

( * ) Notice: Subject to any disclaimer, the term of this patent is extended or adjusted under 35 U.S.C. 154(b) by 185 days.

(21) Appl. No.: 15/801,281

(22) Filed: Nov. 1, 2017

(65) Prior Publication Data

US 2018/0117260 A1    May 3, 2018

Related U.S. Application Data

(60) Provisional application No. 62/542,230, filed on Aug. 7, 2017, provisional application No. 62/480,276, filed
(Continued)

(51) Int. Cl.
*A61M 5/32* (2006.01)
*A61M 5/178* (2006.01)
(Continued)

(52) U.S. Cl.
CPC .......... *A61M 5/3221* (2013.01); *A61M 5/178* (2013.01); *A61M 5/2066* (2013.01);
(Continued)

(58) Field of Classification Search
CPC .............. A61M 5/2066; A61M 5/3221; A61M 5/2448; A61M 5/2484; A61M 5/3148;
(Continued)

(56) References Cited

U.S. PATENT DOCUMENTS 9,814,842 B2    11/2017  Diaz et al.
2004/0215150 A1 10/2004  Shue
(Continued)

FOREIGN PATENT DOCUMENTS

WO    WO 02/096488       12/2002
WO    WO-2015164839 A2 * 10/2015

OTHER PUBLICATIONS

PCT International Preliminary Report on Patentability (Chapter I of the Patent Cooperation Treaty) for PCT/US2017/059612, Applicant: Credence MedSystems, Inc., Form PCT/ISA/326 and 373, dated May 16, 2019.
(Continued)

*Primary Examiner* — Tiffany Legette
(74) *Attorney, Agent, or Firm* — Vista IP Law Group LLP

(57) ABSTRACT

A system for injecting includes a cartridge body defining a proximal opening and a distal needle interface. The system also includes a plunger member defining a plunger interior and configured to be manually manipulated to insert a stopper member relative to the cartridge body. The plunger member includes a needle retention feature disposed in the plunger interior, an energy-storage member disposed in the plunger interior, and an energy-storage member latching member disposed in the plunger interior. The system further includes a needle hub assembly coupled to the distal needle interface of the cartridge body. The needle assembly includes a needle having a needle proximal end feature, a hub, and a needle latching member configured to couple the needle to the hub. The needle is retractable into plunger interior upon manipulation of the plunger member to actuate the energy-storage member latching member.

18 Claims, 93 Drawing Sheets

Related U.S. Application Data on Mar. 31, 2017, provisional application No. 62/431,382, filed on Dec. 7, 2016, provisional application No. 62/416,102, filed on Nov. 1, 2016.

(51) Int. Cl.
  *A61M 5/24* (2006.01)
  *A61M 5/20* (2006.01)
  *A61M 5/28* (2006.01)
  *A61M 5/315* (2006.01)
  *A61M 5/31* (2006.01)
  *A61J 1/20* (2006.01)

(52) U.S. Cl.
  CPC ............ *A61M 5/2448* (2013.01); *A61M 5/28* (2013.01); *A61M 5/284* (2013.01); *A61M 5/3137* (2013.01); *A61M 5/3148* (2013.01); *A61M 5/31501* (2013.01); *A61M 5/31511* (2013.01); *A61M 5/31513* (2013.01); *A61M 5/3202* (2013.01); *A61M 5/322* (2013.01); *A61M 5/3234* (2013.01); *A61J 1/2006* (2015.05); *A61J 1/2096* (2013.01); *A61M 5/3232* (2013.01); *A61M 5/3293* (2013.01); *A61M 2005/323* (2013.01); *A61M 2005/3223* (2013.01); *A61M 2005/3231* (2013.01); *A61M 2005/3241* (2013.01)

(58) Field of Classification Search
  CPC .............. A61M 5/31501; A61M 5/322; A61M 2005/3231; A61M 2005/323; A61M 2005/3241; A61M 5/178; A61M 5/28; A61M 5/284; A61M 5/3137; A61M 5/31511; A61M 5/31513; A61M 5/3202; A61M 5/3232; A61M 5/3293; A61M 5/3222; A61M 2005/3223; A61M 5/3234; A61J 1/2006; A61J 1/2096
  See application file for complete search history.

(56) References Cited

U.S. PATENT DOCUMENTS

| | | |
|---|---|---|
| 2008/0140005 A1 | 6/2008 | Luo |
| 2015/0005706 A1 | 1/2015 | Diaz |
| 2015/0148748 A1* | 5/2015 | Shluzas ............... A61M 5/2466 604/196 |
| 2015/0273161 A1* | 10/2015 | Bengtsson ............ A61M 5/001 604/198 |
| 2016/0206834 A1 | 7/2016 | Shluzas |
| 2018/0117261 A1 | 5/2018 | Steese-Bradley |
| 2018/0133408 A1 | 5/2018 | Shluzas |

OTHER PUBLICATIONS

PCT International Search Report for PCT/US2017/059612, Applicant: Credence MedSystems, Inc., Form PCT/ISA/210 and 220, dated Mar. 26, 2018.

PCT Written Opinion of the International Search Authority for PCT/US2017/059612, Applicant: Credence MedSystems, Inc., Form PCT/ISA/237, dated Mar. 26, 2018.

* cited by examiner

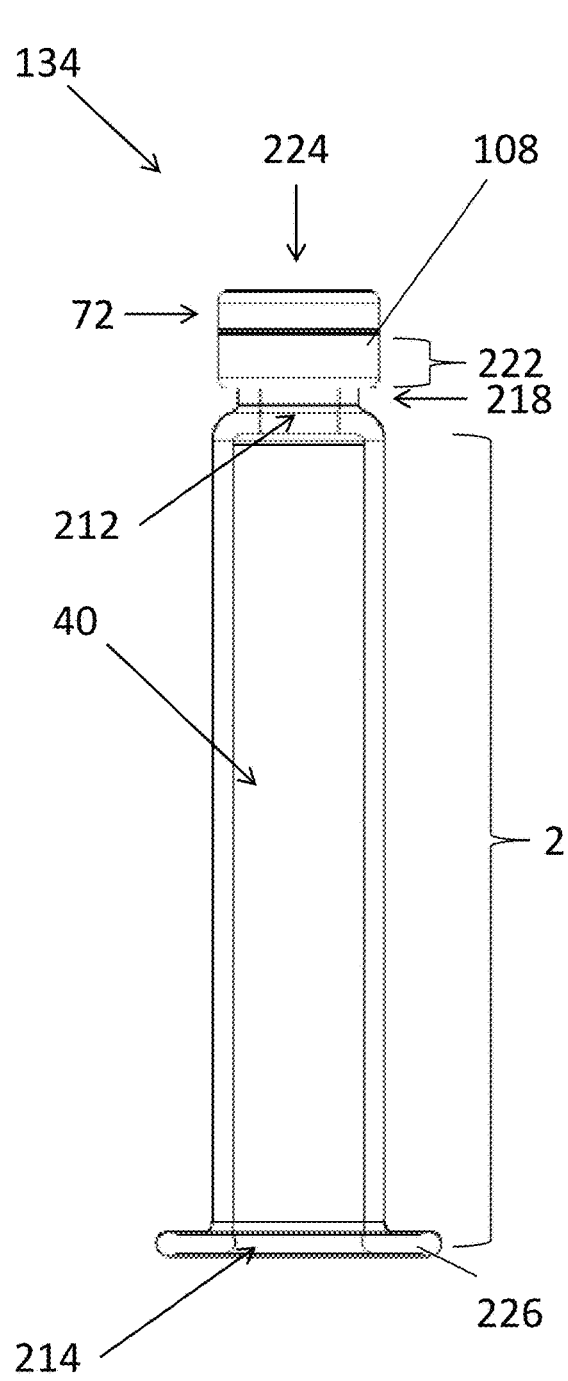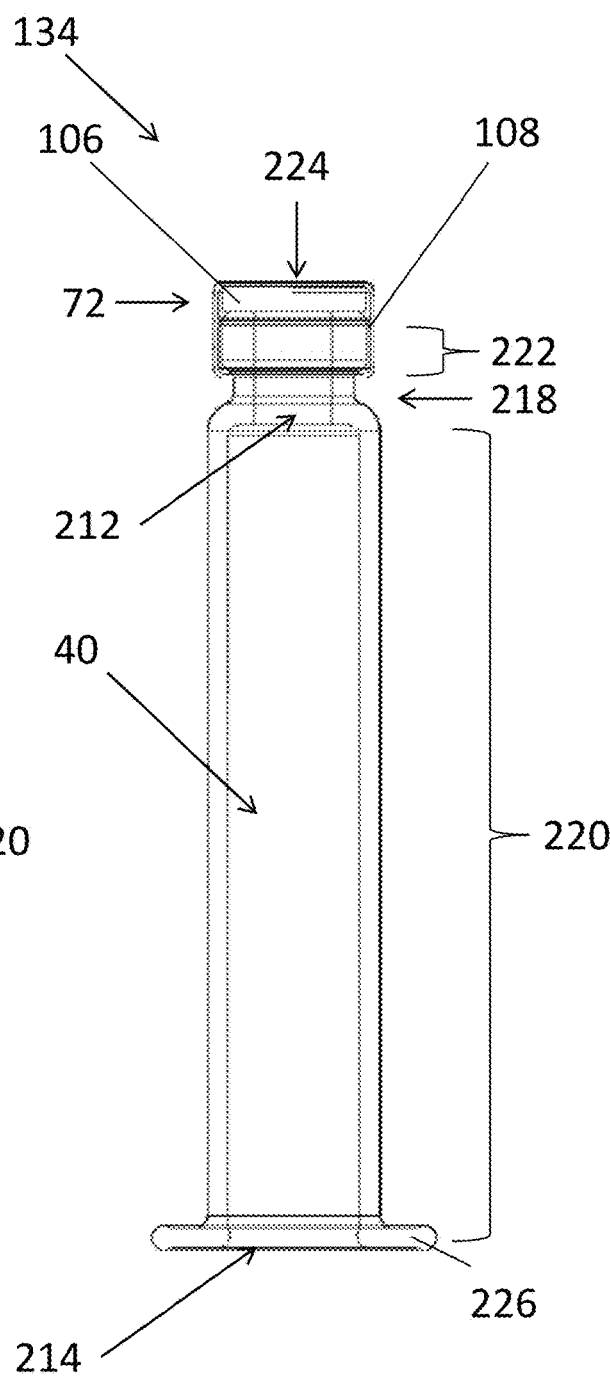

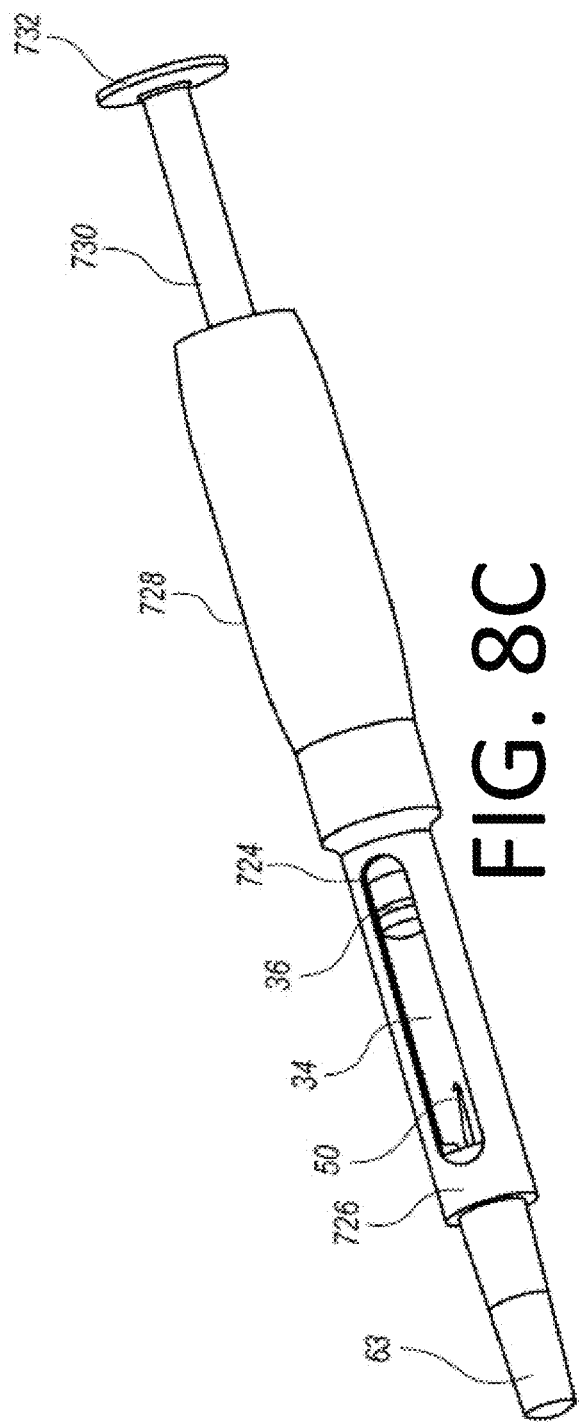
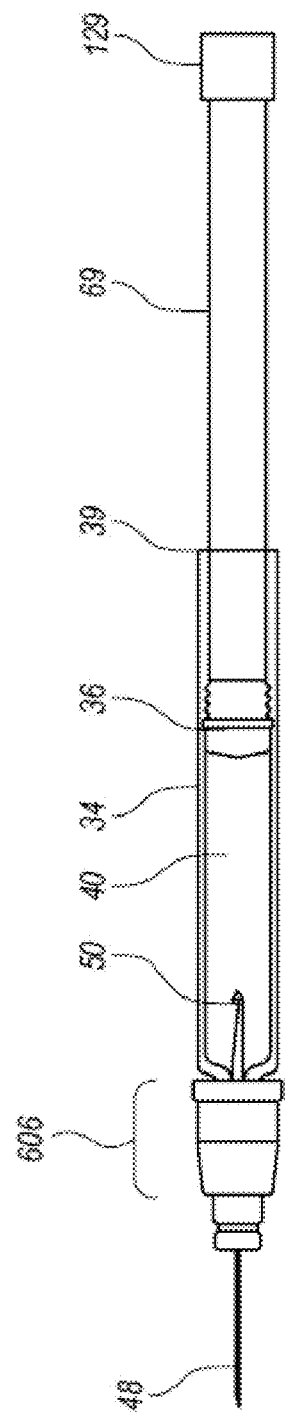
FIG. 8C
FIG. 8D

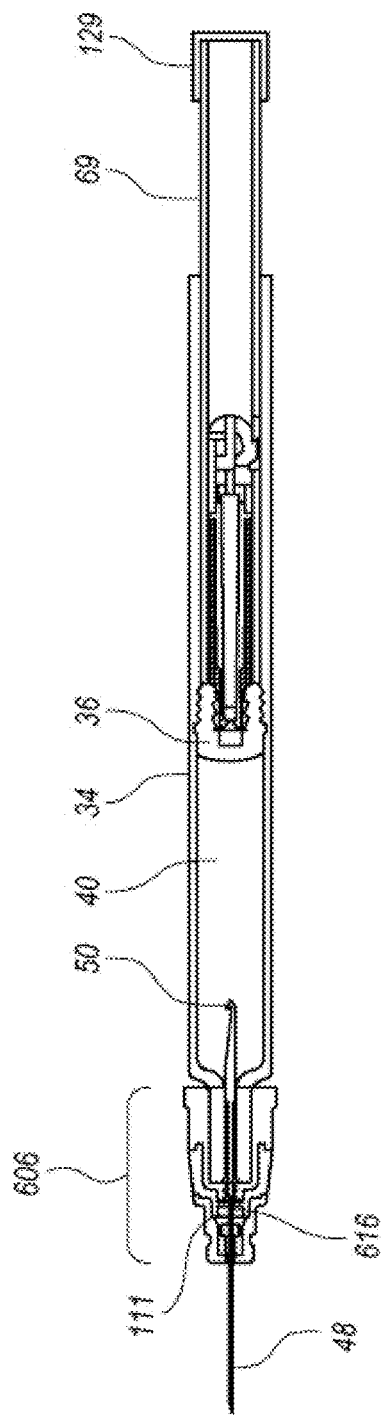
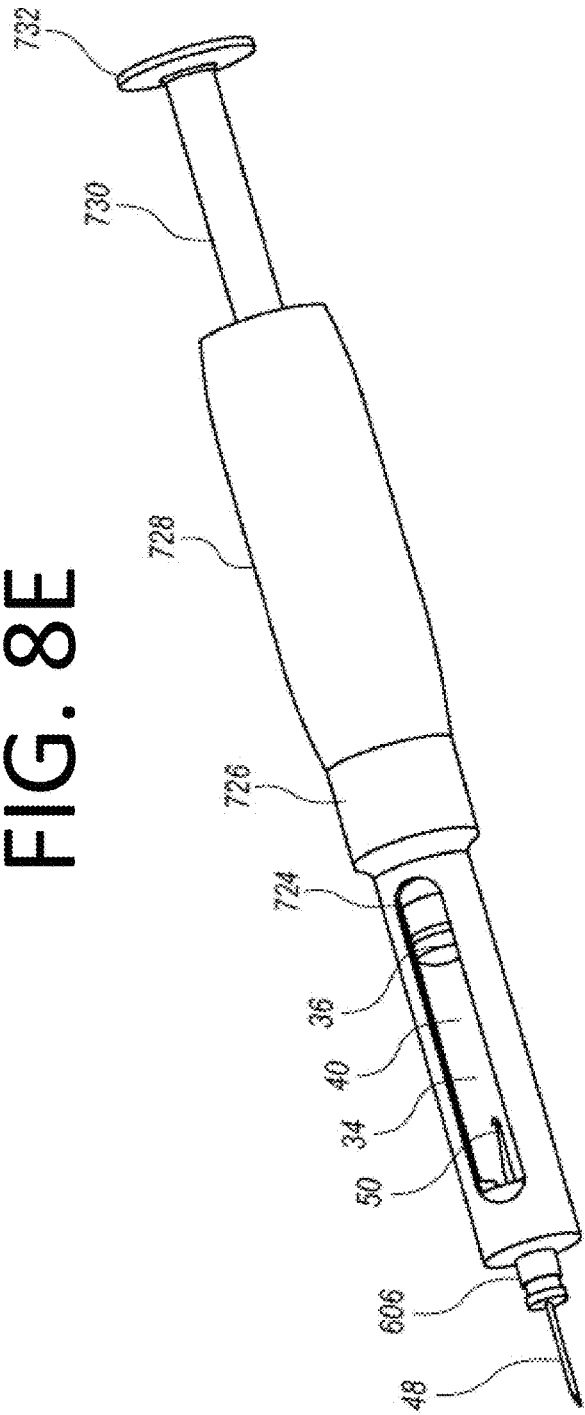
FIG. 8E
FIG. 8F

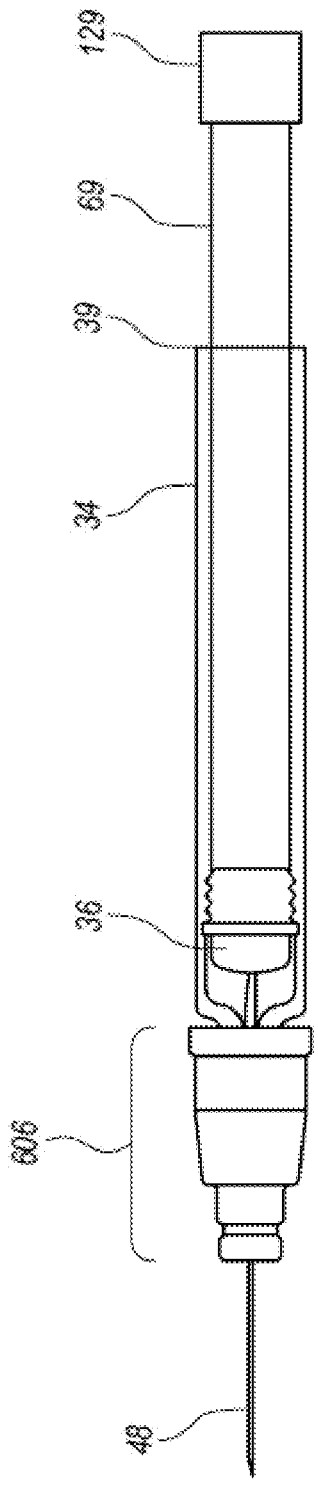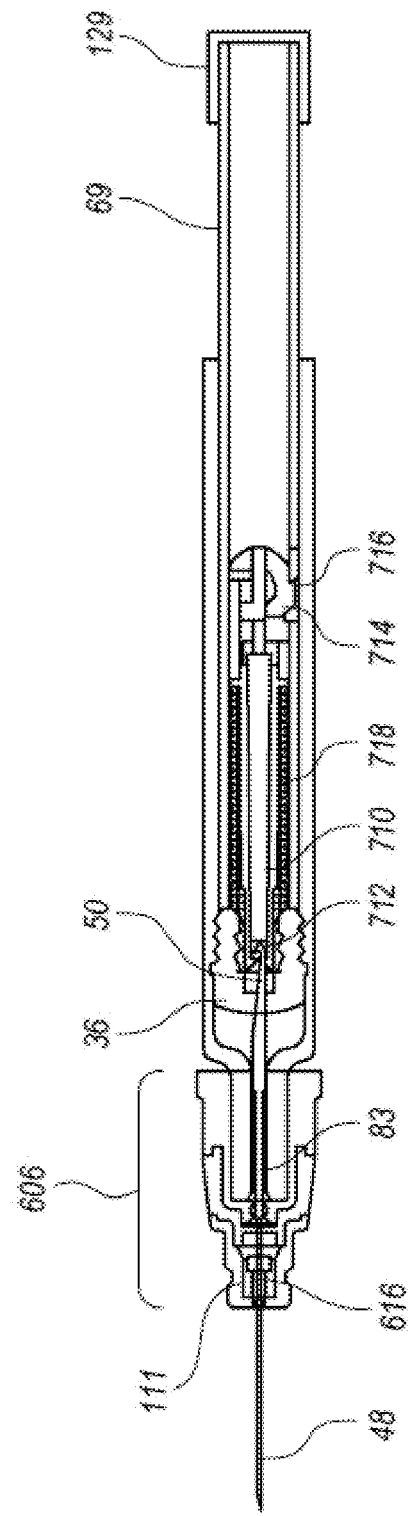
FIG. 8G
FIG. 8H

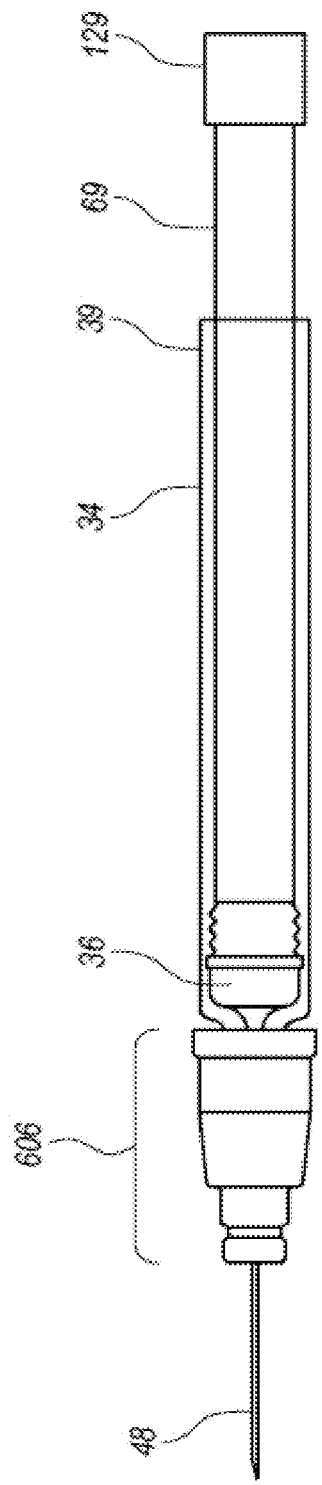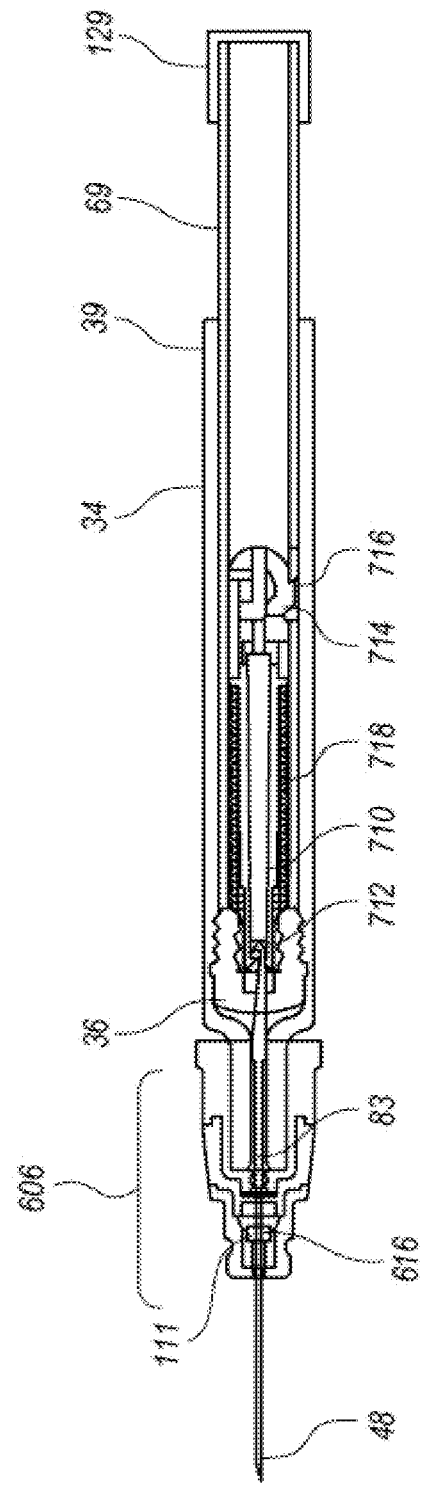

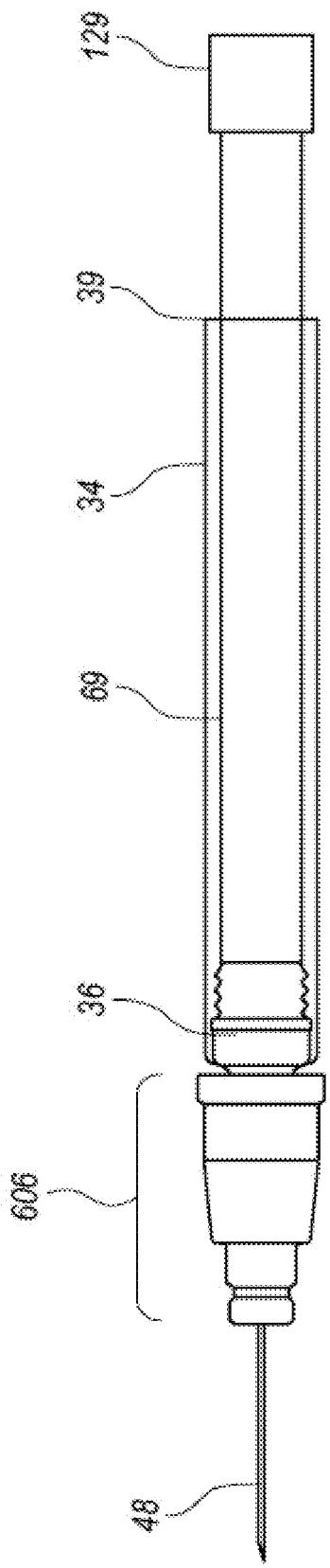
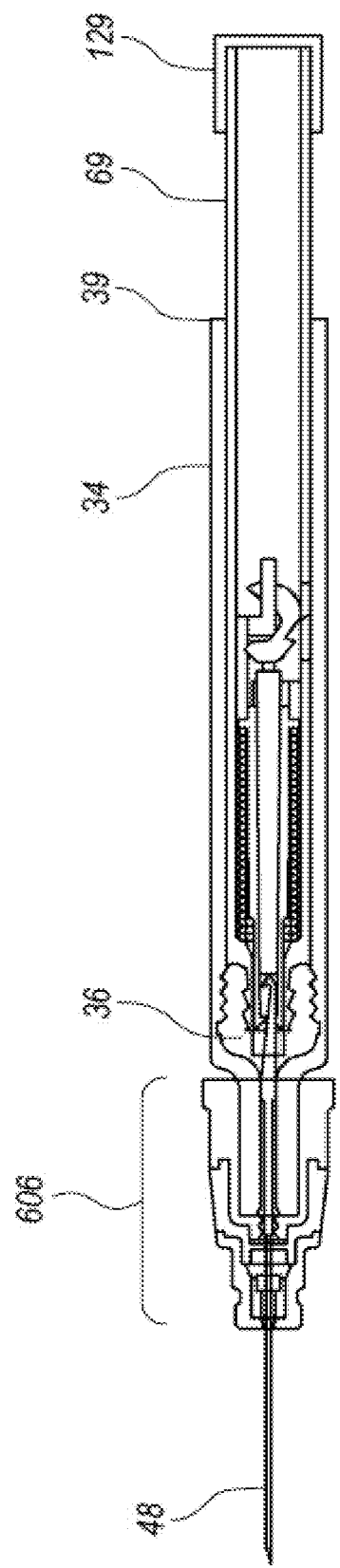
FIG. 8K
FIG. 8L

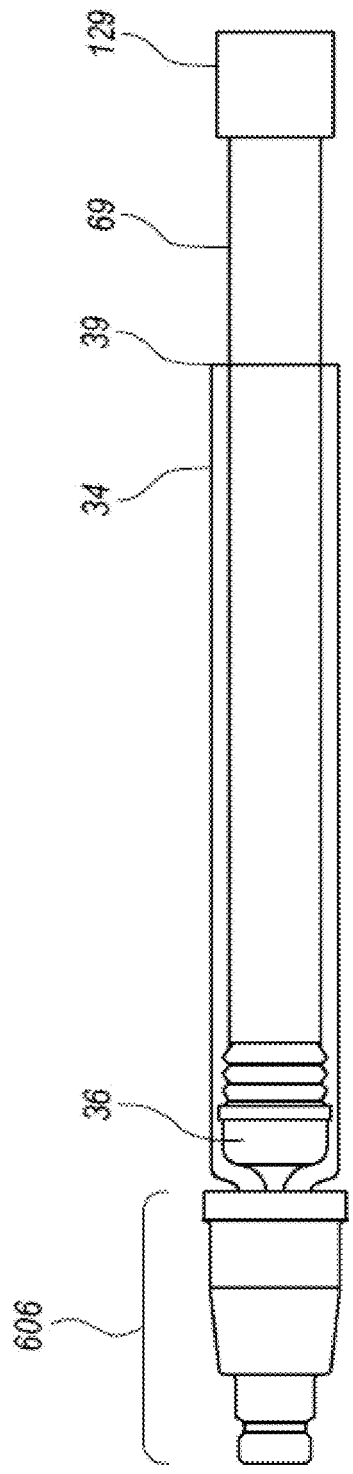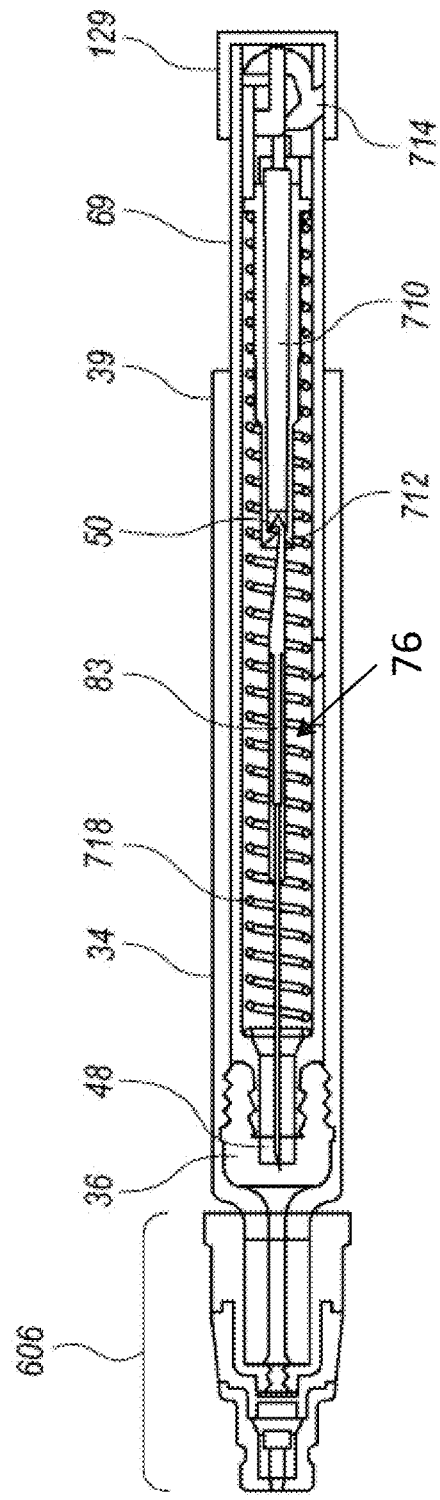

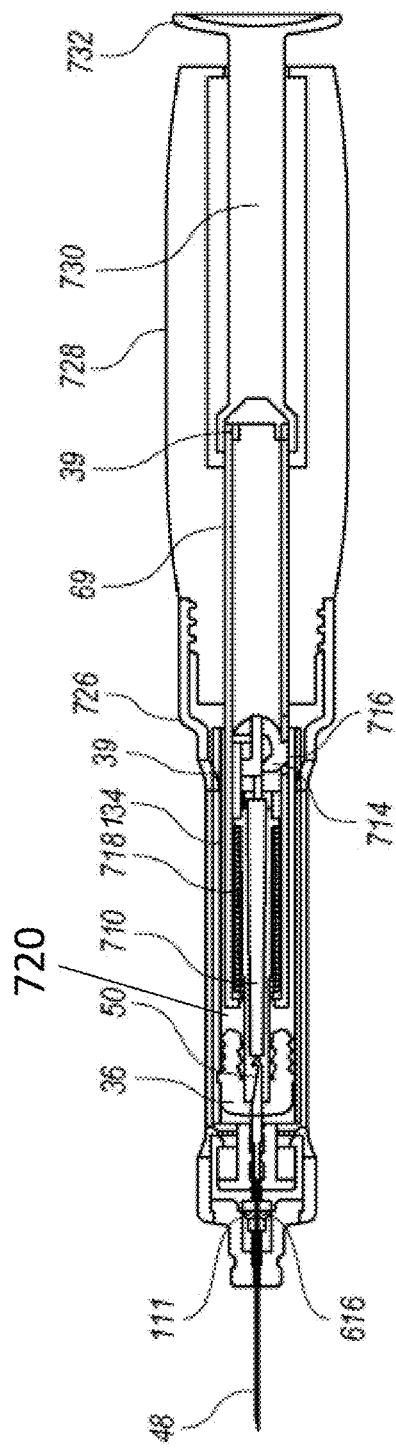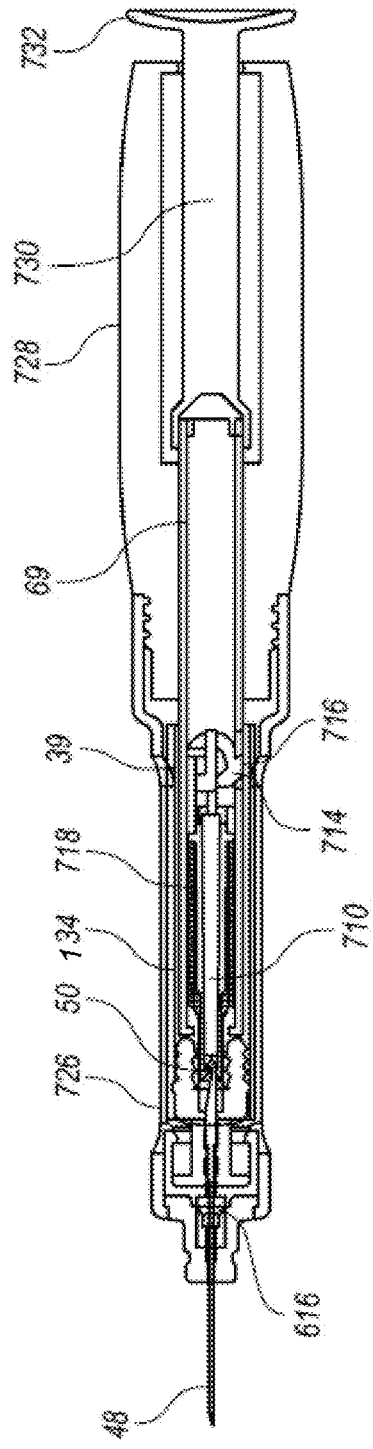

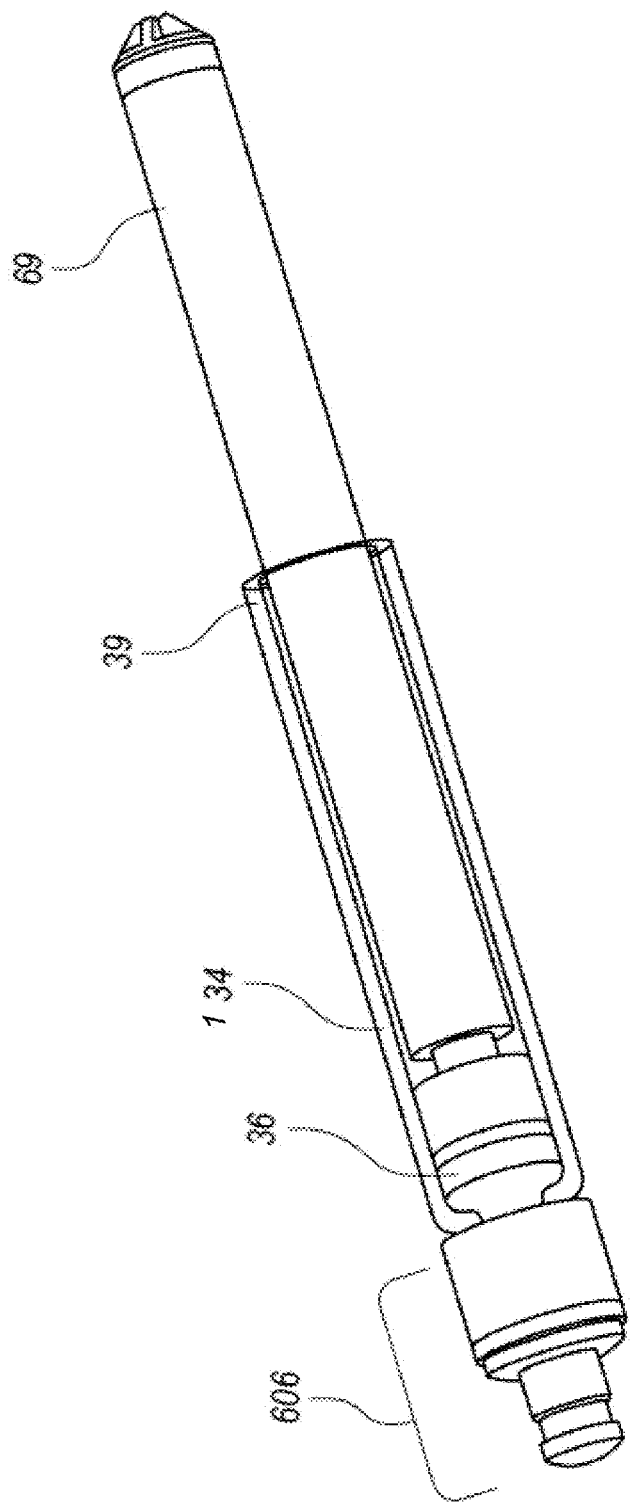

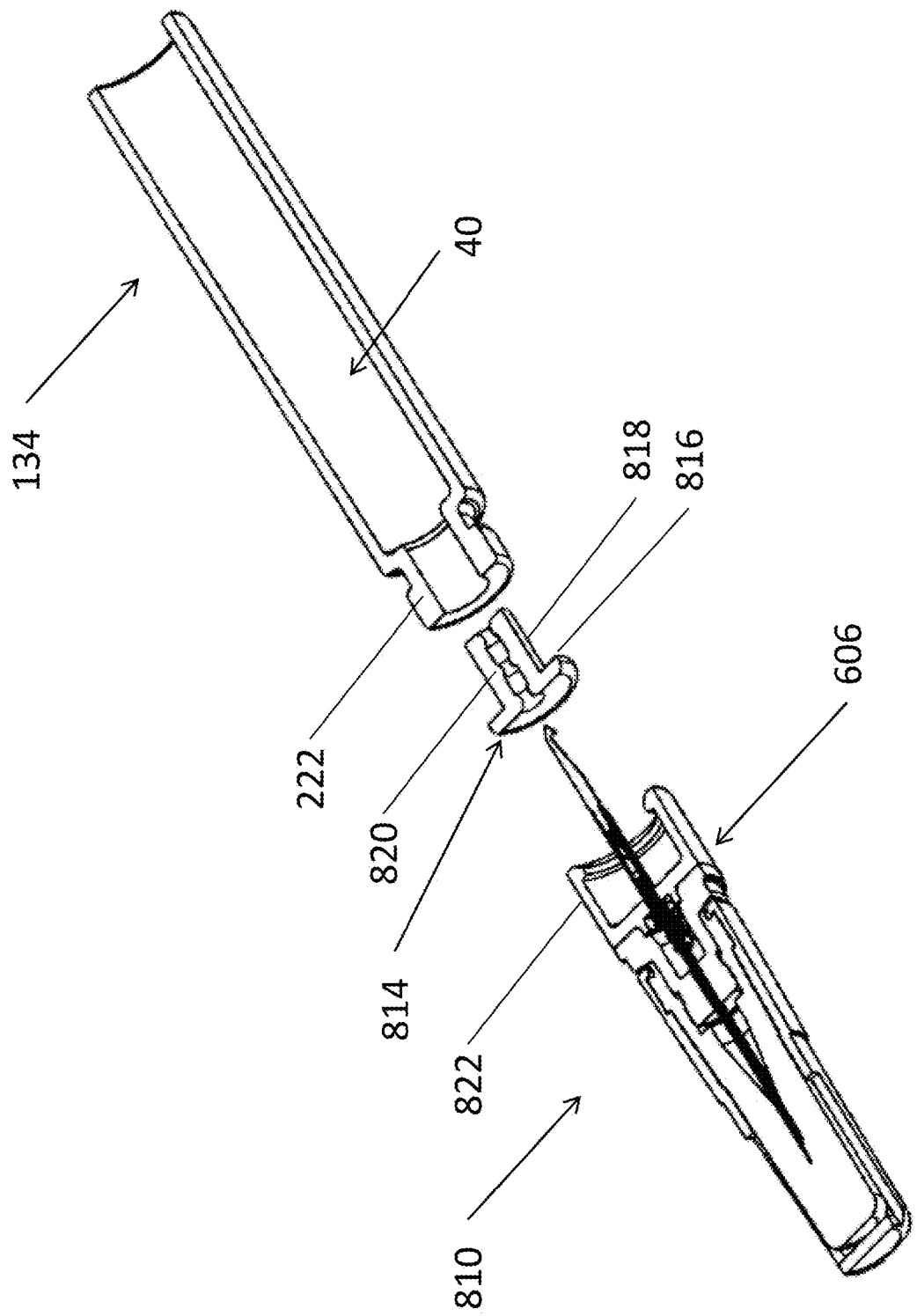

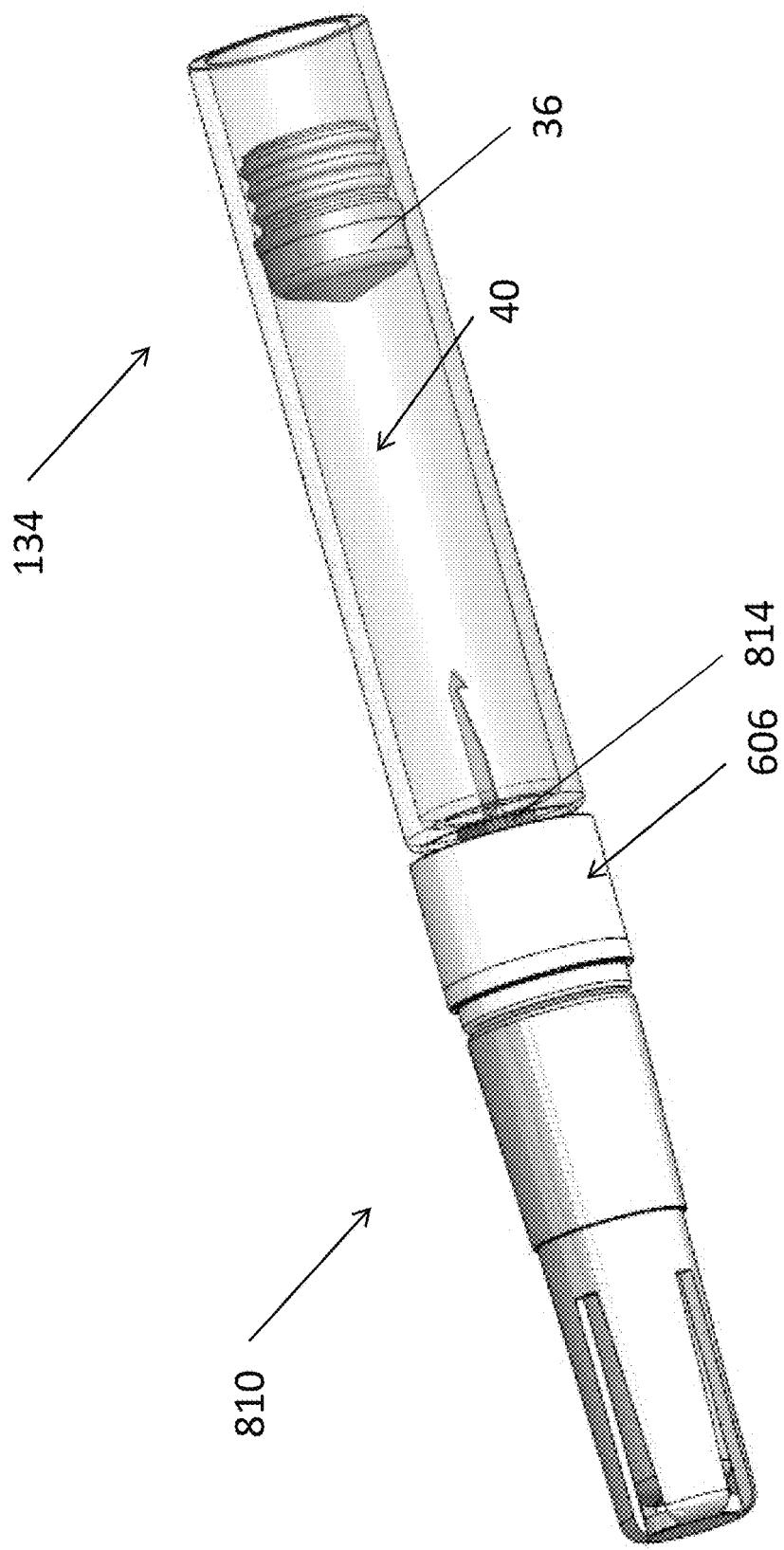

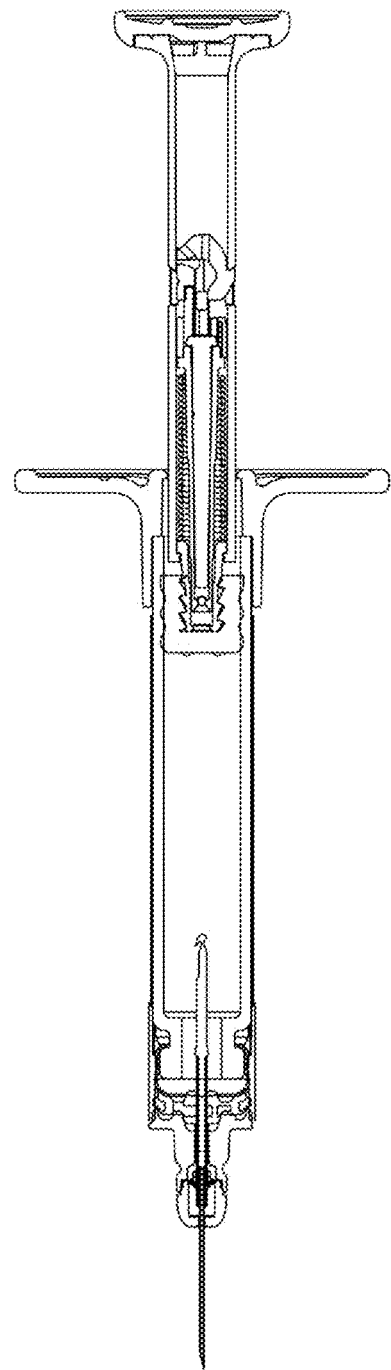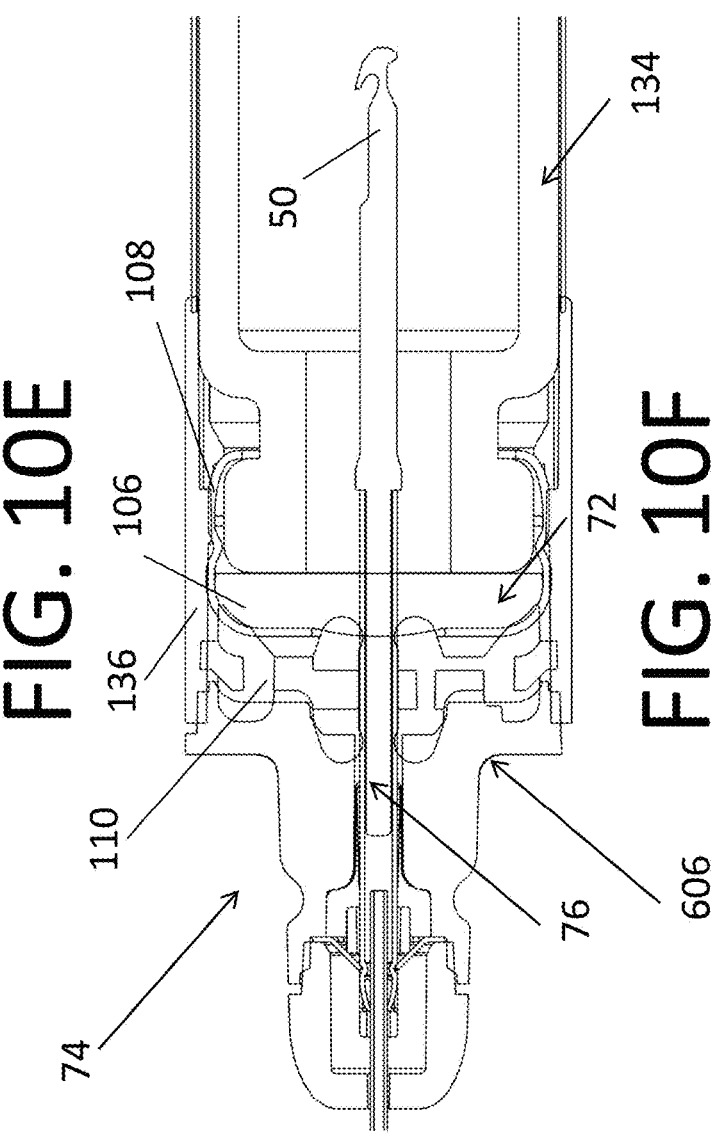
FIG. 10E
FIG. 10F

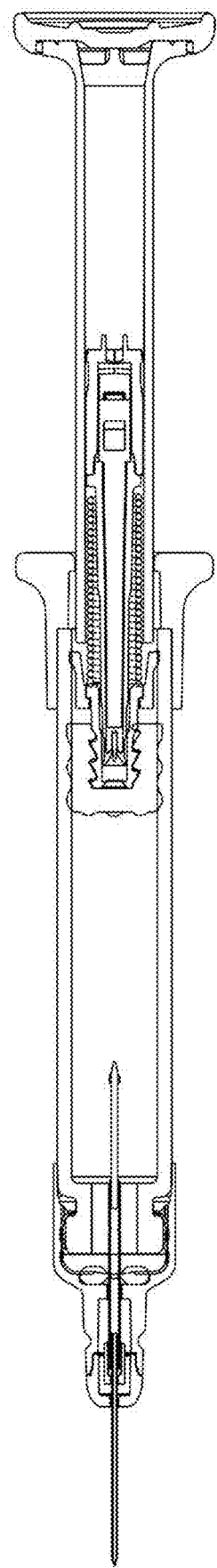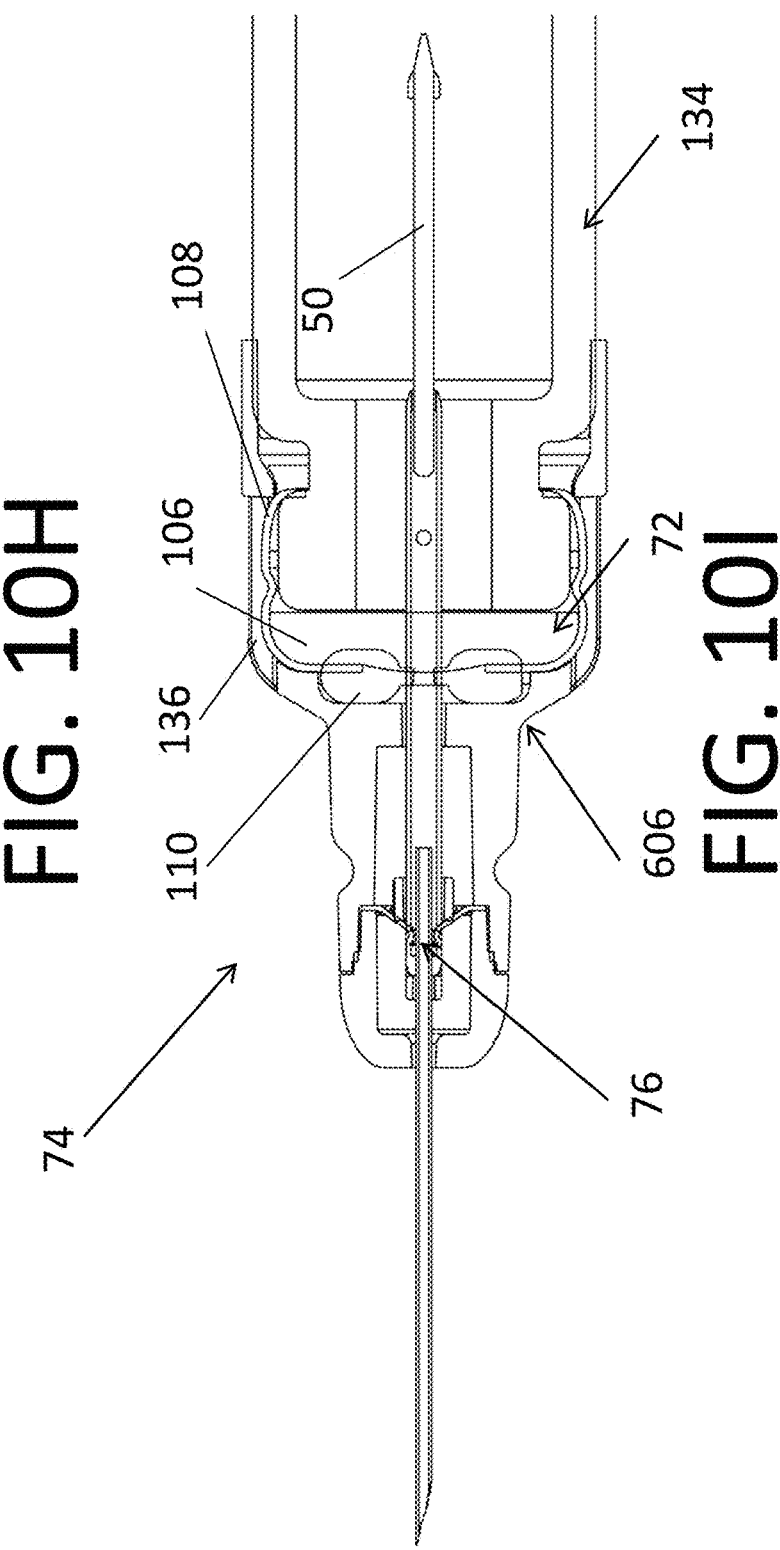
FIG. 10H
FIG. 10I

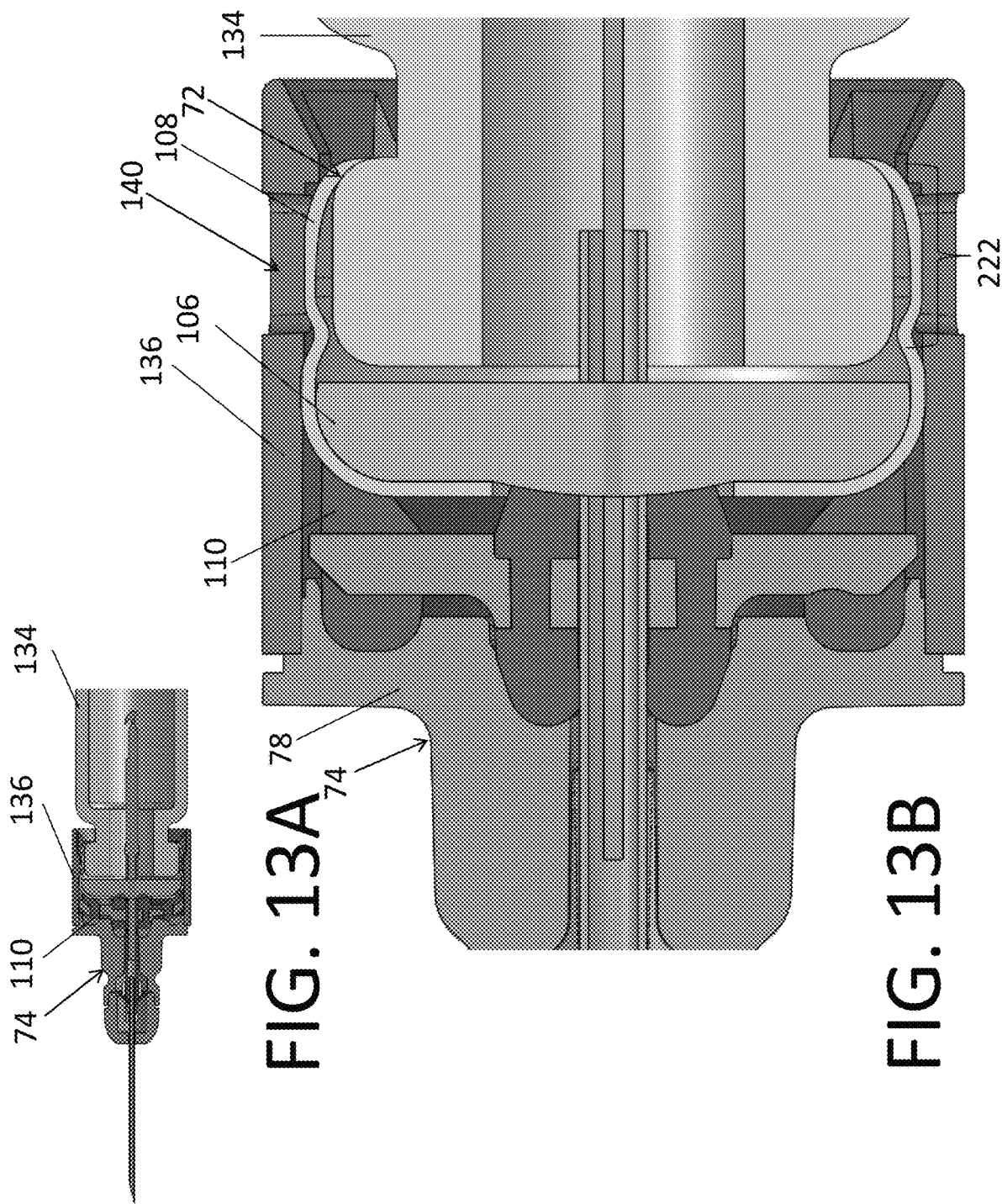

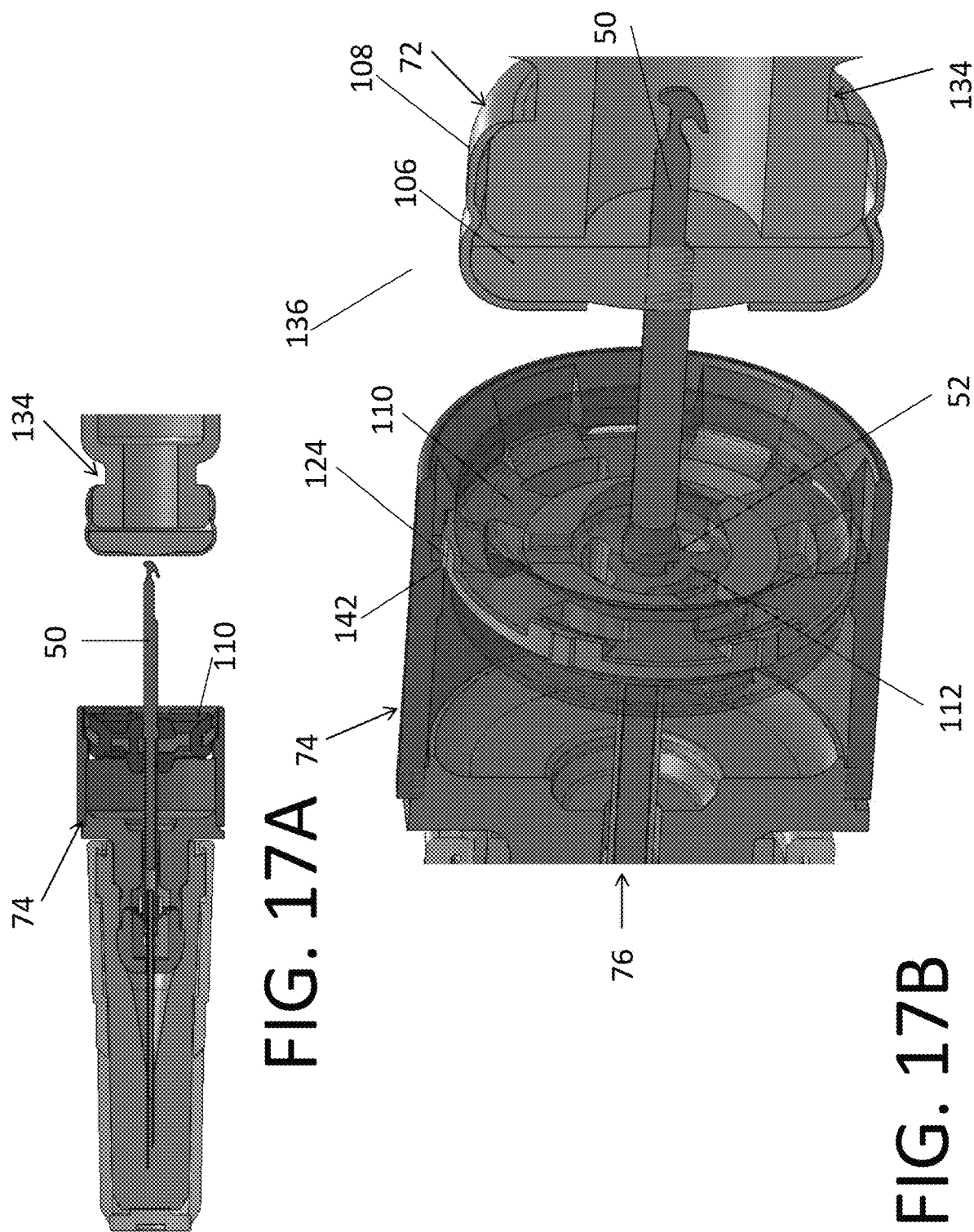

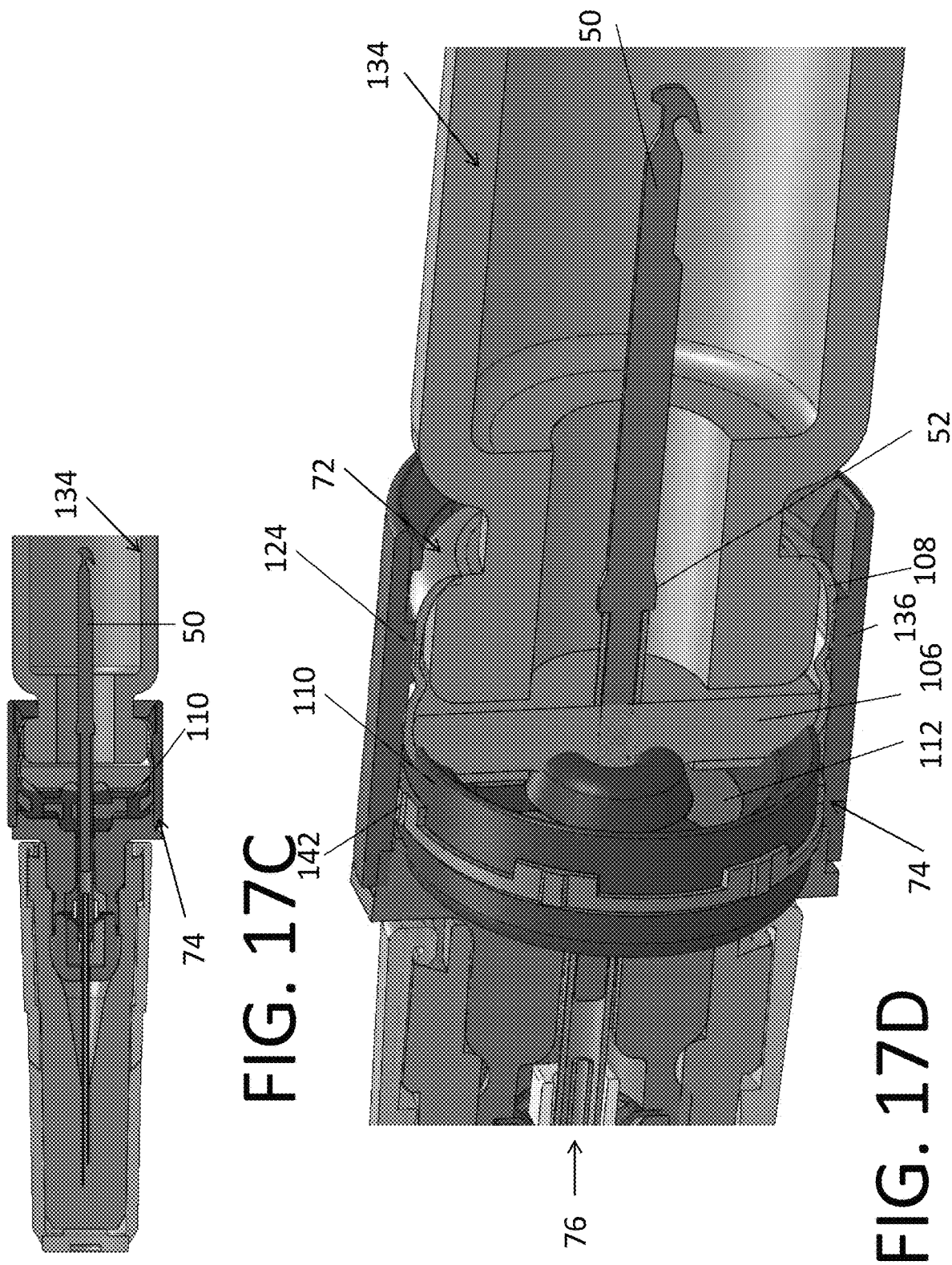

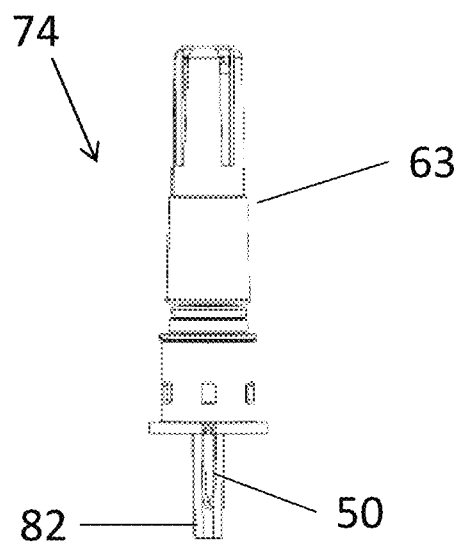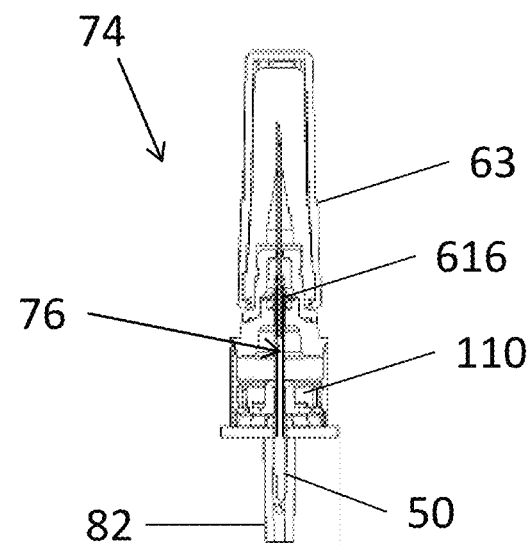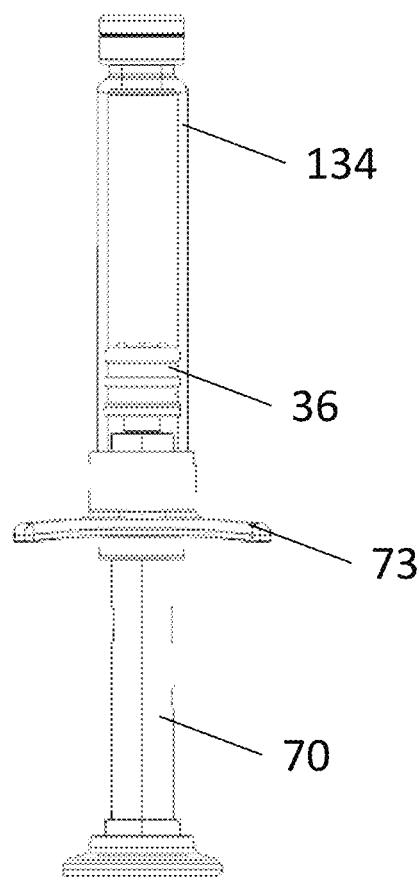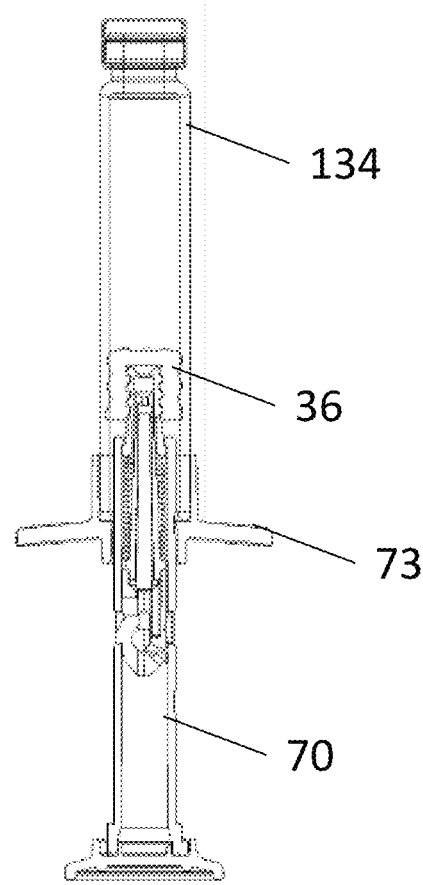
FIG. 25A  FIG. 25B

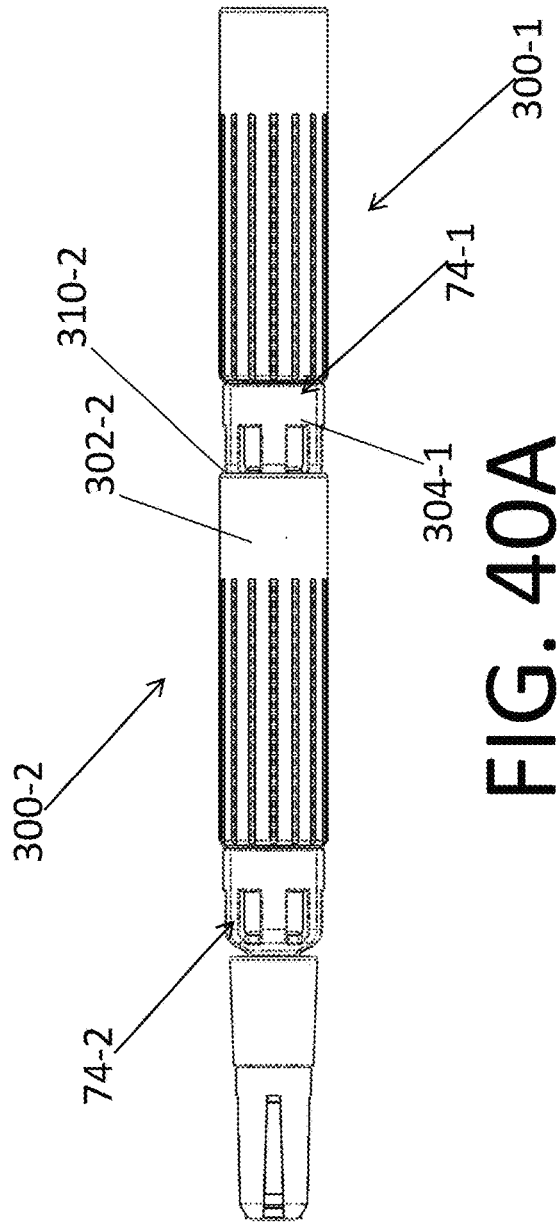
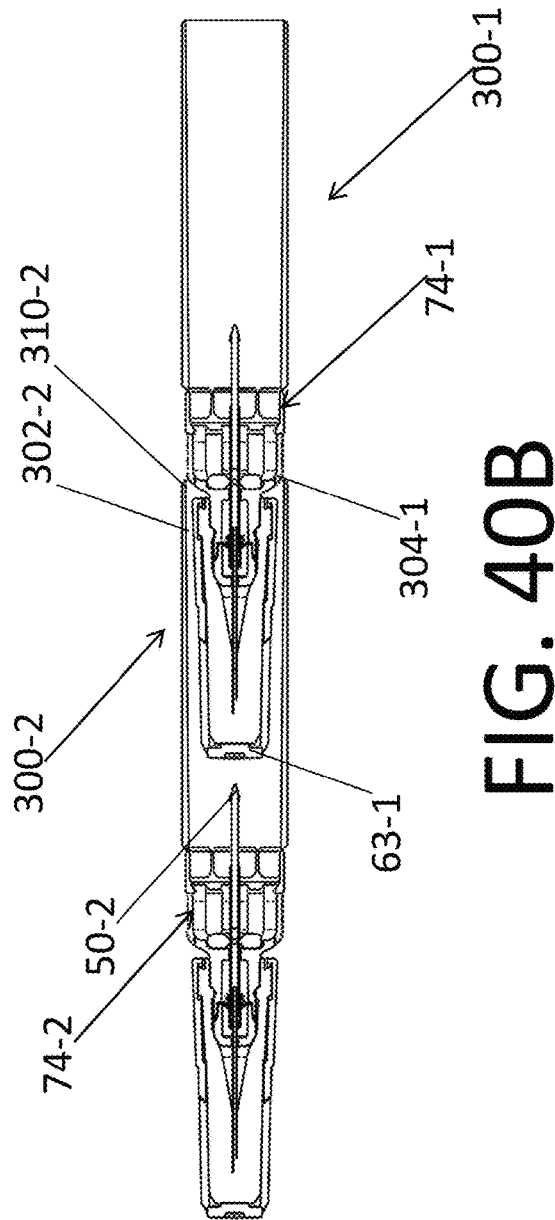
FIG. 40A
FIG. 40B

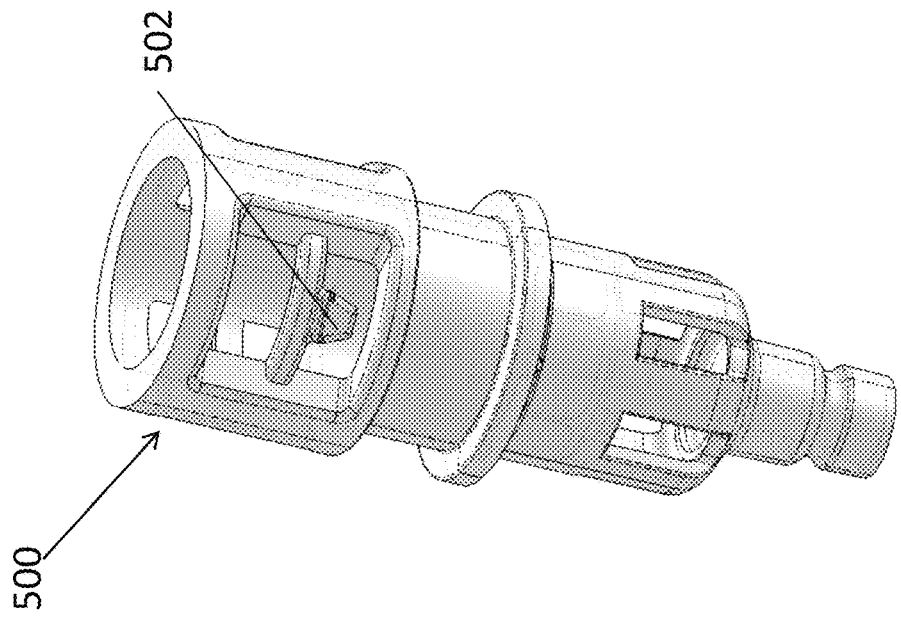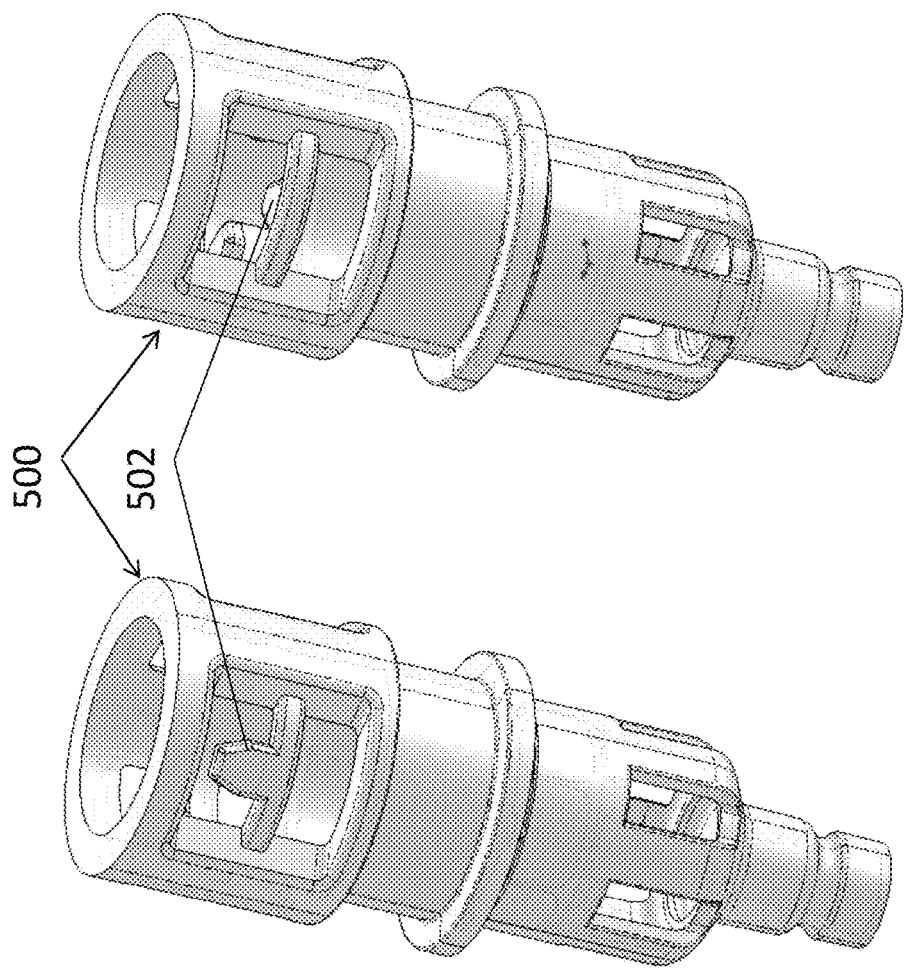
FIG. 45A  FIG. 45B  FIG. 45C

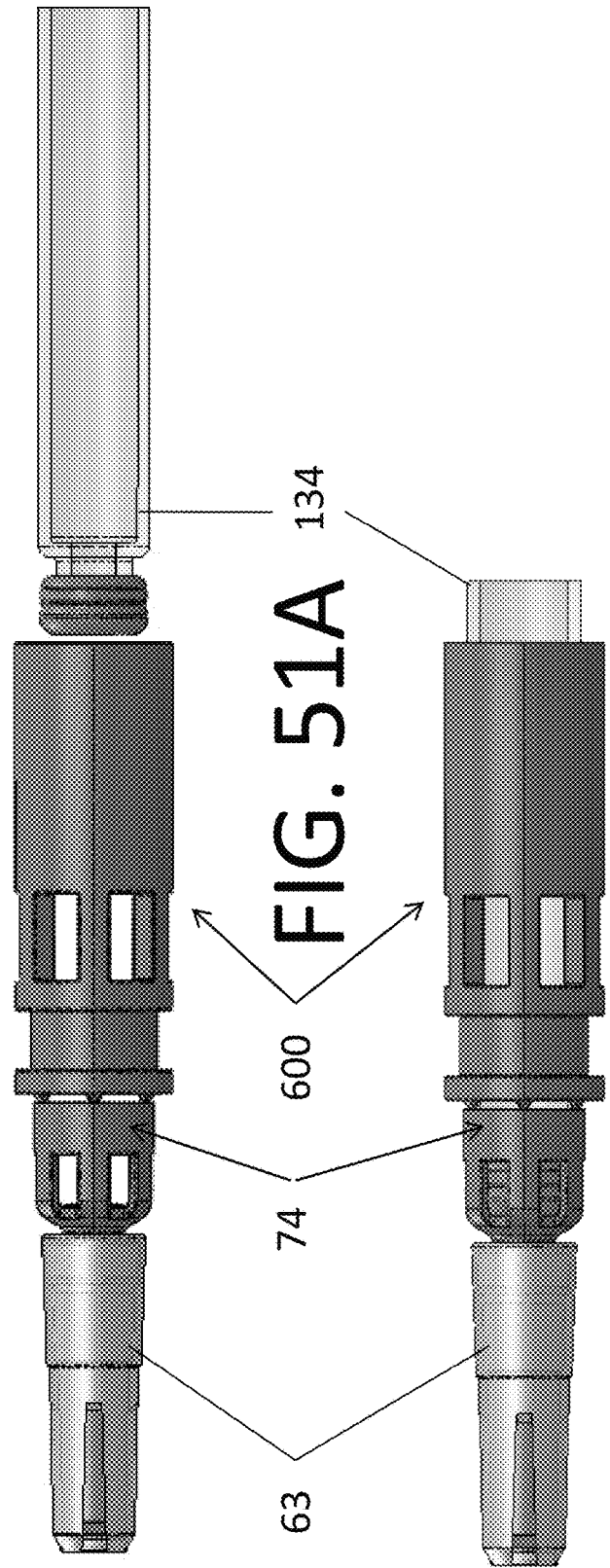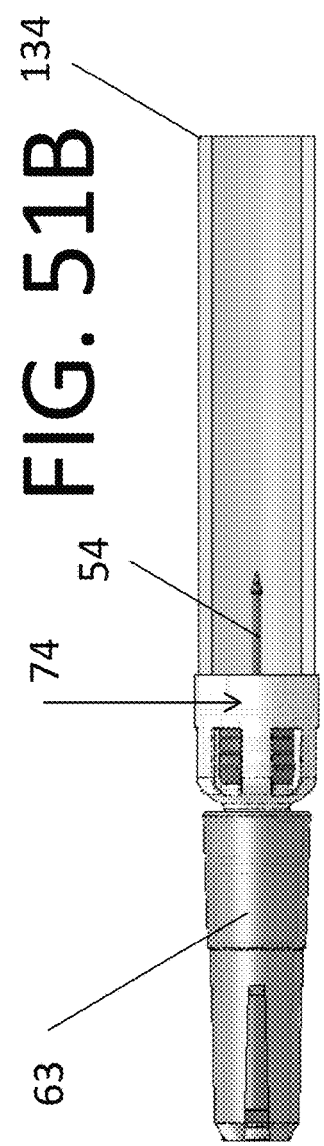
FIG. 51A  FIG. 51B  FIG. 51C

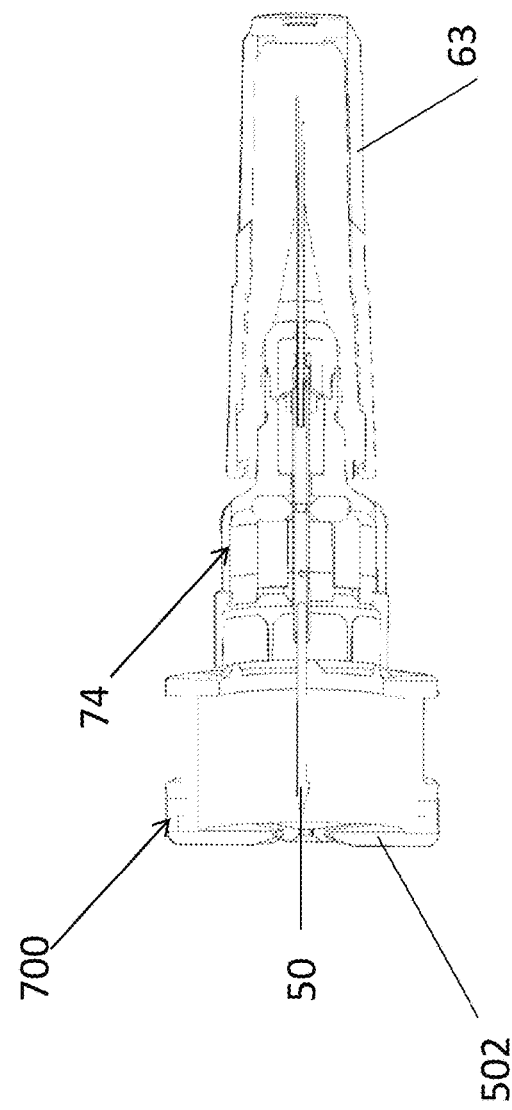
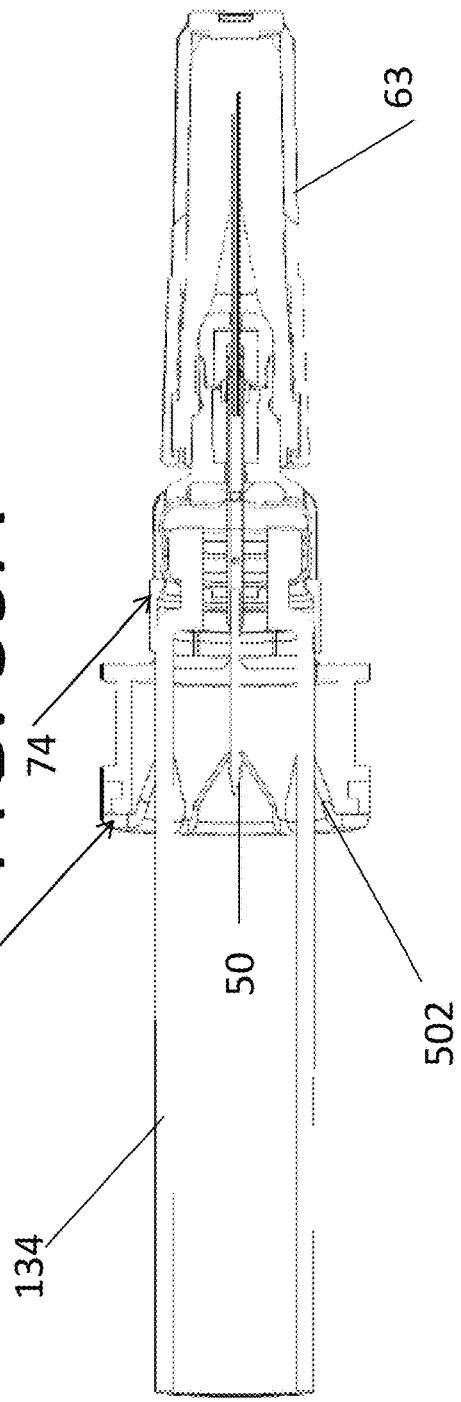

CARTRIDGE SAFETY INJECTION SYSTEM AND METHODS

CROSS-REFERENCE TO RELATED APPLICATION(S)

The present application claims priority to (1) U.S. Provisional Patent Application Ser. No. 62/416,102, filed on Nov. 1, 2016 entitled "SYSTEM AND METHOD FOR SAFETY SYRINGE"; (2) U.S. Provisional Patent Application Ser. No. 62/431,382, filed on Dec. 7, 2016 entitled "SYSTEM AND METHOD FOR SAFETY SYRINGE"; (3) U.S. Provisional Patent Application Ser. No. 62/480,276, filed Mar. 31, 2017 entitled "SYSTEM AND METHOD FOR SAFETY SYRINGE"; (4) U.S. Provisional Patent Application Ser. No. 62/542,230, filed Aug. 7, 2017 entitled "CARTRIDGE SAFETY INJECTION SYSTEM AND METHODS." This application includes subject matter similar to the subject matter described in the following co-owned U.S. patent applications: (1) U.S. Utility patent application Ser. No. 14/696,342, filed Apr. 24, 2015, entitled "SYSTEM AND METHOD FOR SAFETY SYRINGE"; (2) U.S. Utility patent application Ser. No. 14/543,787, filed Nov. 17, 2014, entitled "SYSTEM AND METHOD FOR DRUG DELIVERY WITH A SAFETY SYRINGE"; (3) U.S. Utility patent application Ser. No. 14/321,706, filed Jul. 1, 2014, entitled "SAFETY SYRINGE"; (4) U.S. Utility Patent Application filed on Nov. 1, 2017 entitled "SYSTEM AND METHOD FOR SAFETY SYRINGE"; (5) U.S. Utility Patent Application filed on Nov. 1, 2017 entitled "SYSTEM AND METHOD FOR SAFETY SYRINGE"; and (6) U.S. Utility Patent Application filed on Nov. 1, 2017 entitled "SYSTEM AND METHOD FOR SAFETY SYRINGE." The contents of the above-mentioned applications are fully incorporated herein by reference as though set forth in full.

FIELD OF THE INVENTION

The present invention relates generally to injection systems, devices, and processes for facilitating various levels of control over fluid infusion, and more particularly to systems and methods related to safety syringes for use with cartridges in healthcare environments.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs. Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer manifold assembly of FIG. 2B may be used to administer liquid drugs to the patient intravenously with or without the use of an intravenous infusion bag. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting (14) which are configured to engage a flange on the female fitting (18) and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during assembly of a Luer coupling. The use of needle injection configurations, on the other hand, carries with it the risk of a sharp needle contacting or stabbing a person or structure that is not desired. For this reason, so called "safety syringes" have been developed.

One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28, 26) back to a safe position within the tubular body (4), as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity control which may be associated with pain and patient anxiety.

Further complicating the syringe marketplace is an increasing demand for pre-filled syringe assemblies such as those depicted in FIGS. 5A and 5B, which generally comprise a syringe body, or "drug enclosure containment delivery system", (34), a plunger tip, plug, or stopper (36), and a distal seal or cap (35) which may be fitted over a Luer type interface (FIG. 5A shows the cap 35 in place; FIG. 5B has the cap removed to illustrate the Luer interface (14). Liquid medicine may reside in the volume, or medicine reservoir, (40) between the distal seal (35) and the distal end (37) of the stopper member (36). The stopper member (36) may comprise a standard butyl rubber material and may be coated, such as with a biocompatible lubricious coating (e.g., polytetrafluoroethylene ("PTFE")), to facilitate preferred sealing and relative motion characteristics against the associated syringe body (34) structure and material. The proximal end of the syringe body (34) in FIG. 5B comprises a conventional integral syringe flange (38), which is formed integral to the material of the syringe body (34). The flange (38) is configured to extend radially from the syringe body (34) and may be configured to be a full circumference, or a partial circumference around the syringe body (34). A partial flange is known as a "clipped flange" while the other is known as a "full flange." The flange is used to grasp the syringe with the fingers to provide support for pushing on the plunger to give the injection. The syringe body (34) preferably comprises a translucent material such as a glass or polymer. To form a contained volume within the medicine chamber or reservoir (40), and to assist with expulsion of the associated fluid through the needle, a stopper member (36) may be positioned within the syringe body (34). The syringe body (34) may define a substantially cylindrical shape (i.e., so that a plunger tip 36 having a circular cross sectional shape may establish a seal against the syringe body (34)), or be configured to have other cross sectional shapes, such as an ellipse.

Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as that (41) featured in FIG. 5C, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

Moreover, many pre-filled syringe assemblies include pre-filled cartridges that are used in injection systems. Assembling pre-filled cartridges with needle hub assemblies presents challenges for meeting safety, auto-disabling, and anti-needle-stick standards. For instance, some safe needle retraction systems require more precise positioning of components during assembly, which may not be compatible with various tolerances of existing pre-filled cartridges.

There is a need for injection systems which address the shortcomings of currently-available configurations. In particular, there is a need for safety syringe assemblies including pre-filled cartridges that meet various injection system standards, such as safety, auto-disabling, and anti-needle-stick. It is also desirable that such syringe assemblies may utilize the existing and relatively well-controlled supply chain of conventionally delivered pre-filled cartridges.

SUMMARY

Embodiments are directed to injection systems. In particular, the embodiments are directed to.

In one embodiment, a system for injecting includes a cartridge body having proximal and distal openings, and a distal cartridge body interface. The system also includes a stopper member disposed in a cartridge interior of the cartridge body. The system further includes a plunger member having a plunger interior and configured to be manually manipulated to insert the stopper member relative to the cartridge body. In addition, the system includes a needle hub assembly coupled to the distal cartridge body interface of the cartridge body. The plunger member includes a needle retention feature disposed in the plunger interior. The plunger member also includes an energy-storage member disposed in the plunger interior. The plunger member further includes an energy-storage member latching member disposed in the plunger interior. The needle assembly includes a needle having a needle proximal end feature. The needle assembly also includes a hub. The needle assembly further includes a needle latching member configured to selectively prevent the needle from moving proximally relative to the hub. Manipulating the plunger member relative to the cartridge body to transform the energy-storage member latching member from a latched state to an unlatched state retracts the needle proximal end feature proximally through the stopper member.

The aforementioned and other embodiments of the invention are described in the Detailed Description which follows.

BRIEF DESCRIPTION OF THE DRAWINGS

The foregoing and other aspects of embodiments are described in further detail with reference to the accompanying drawings, in which the same elements in different figures are referred to by common reference numerals, wherein:

FIGS. 6A-6D depict cartridges for use with safe injection systems according to various embodiments.

FIGS. 9A and 9B depict a cartridge and needle hub assembly for use with a safe injection system according to one embodiment.

FIGS. 10E and 10H depict cartridge safe injection systems according to two embodiments.

FIGS. 10F and 10I depict the needle hub assembly/ cartridge seal interface of the two embodiments depicted in FIGS. 10E and 10H.

FIGS. 12A-20 depict cartridge safe injection systems having secondary/backup seals according to various embodiments.

FIGS. 25A-25H depict a method of assembling a cartridge safe injection system and performing an injection using same according to another embodiment.

FIGS. 27-41 depict cartridge safe injection systems and components thereof having a proximally-extending protective sleeve according to various embodiments.

FIGS. 43-48B depict needle proximal end protector according to another embodiment.

FIGS. 49-51C depict needle proximal end protector according to still another embodiment.

FIGS. 52A-60 depict needle proximal end protector according to yet another embodiment.

Figure 1A:
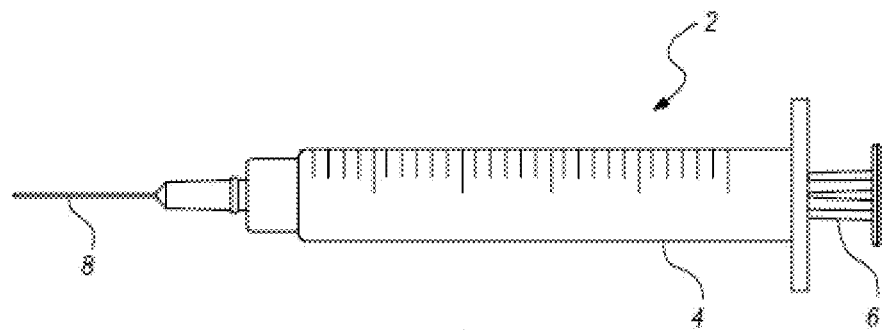
FIGS. 1A-5C illustrate various aspects of conventional injection syringe configurations.
Figure 1B:
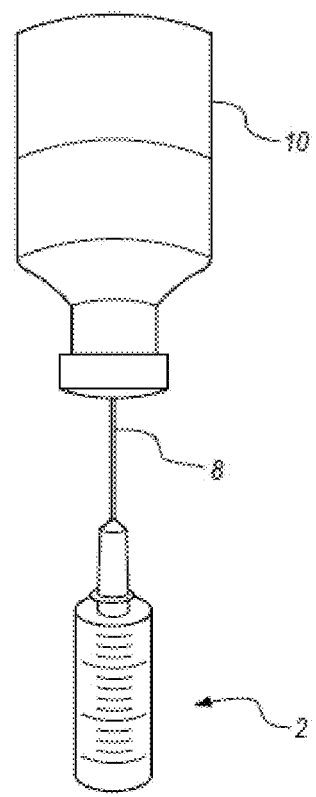
Figure 2A:
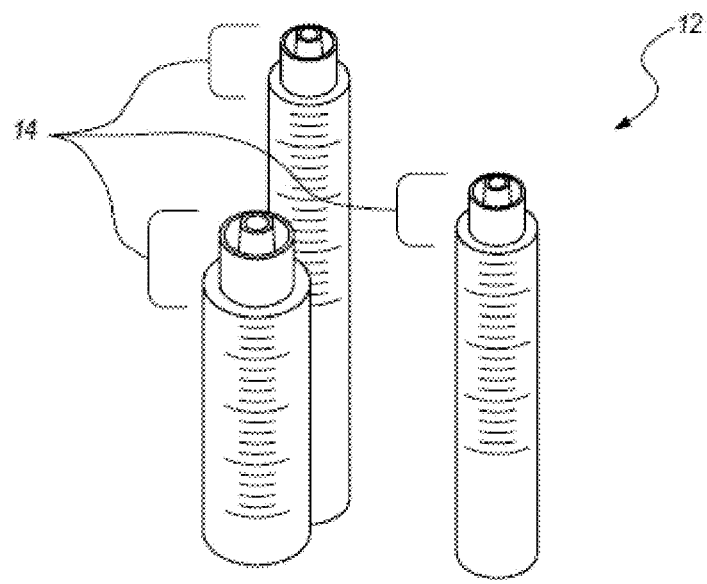
Figure 2B:
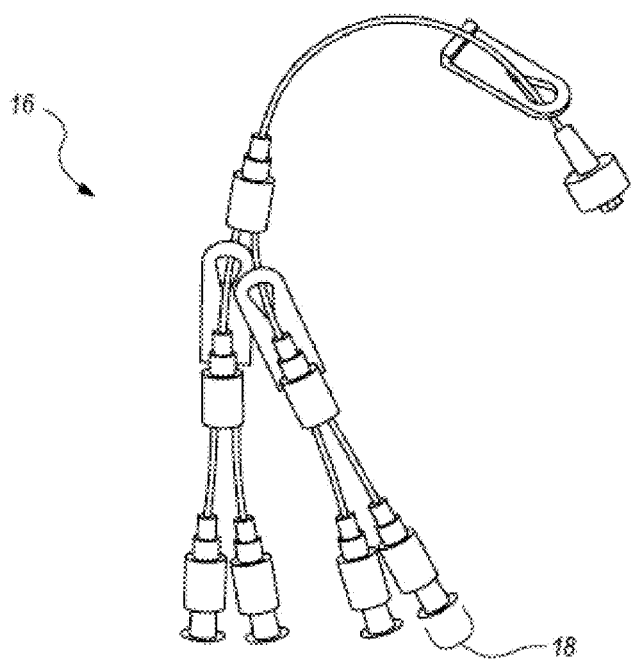
Figure 3:
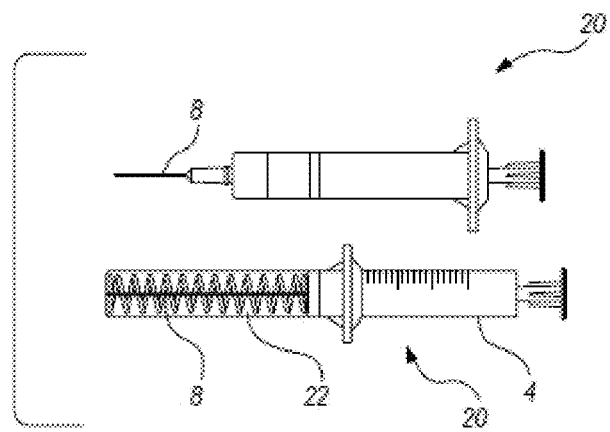
Figure 4A:
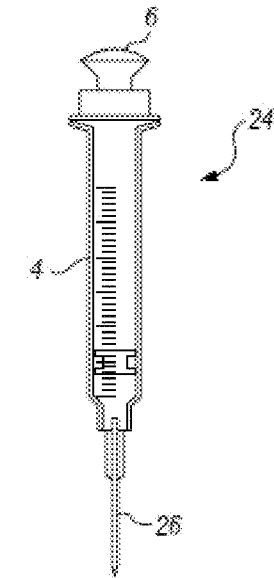
Figure 4B:
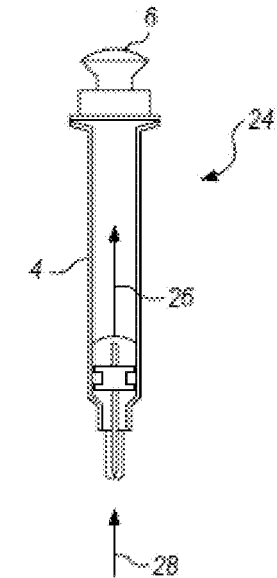
Figure 5A:
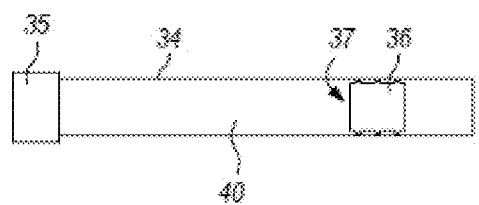
Figure 5B:
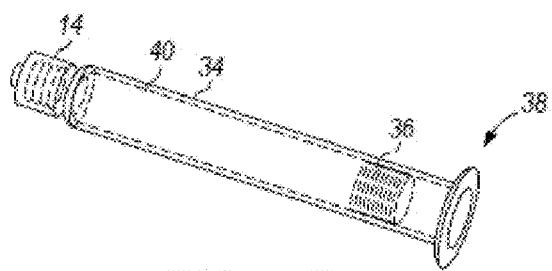
Figure 5C:
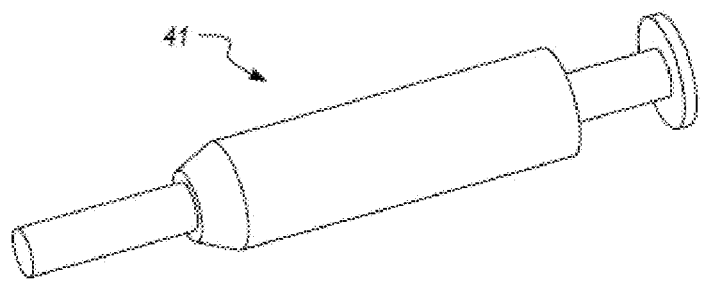

In order to better appreciate how to obtain the above-recited and other advantages and objects of various embodiments, a more detailed description of embodiments is provided with reference to the accompanying drawings. It should be noted that the drawings are not drawn to scale and that elements of similar structures or functions are represented by like reference numerals throughout. It will be understood that these drawings depict only certain illustrated embodiments and are not therefore to be considered limiting of scope of embodiments.

DETAILED DESCRIPTION OF ILLUSTRATED EMBODIMENTS

Exemplary Cartridges for Safe Injection Systems

FIGS. 6A-6D depict two cartridges with which the safety syringe embodiments described herein may be used. The cartridge (134) in FIGS. 6A-6B has open proximal and distal ends (214, 212) that communicate with an interior (40) of the cartridge (134). The distal end of the cartridge (134) has a reduced diameter neck portion (218) that connects a body portion (220) to a flange portion (222). The open distal end (212) is covered by a sealing member (106), which is held in place by a crimp (108) over the flange portion (222). The crimp (108) is a ring with an opening (224) in the middle thereof for access to the sealing member (106) and the open distal end (212) of the cartridge (134). The sealing member (106) may be made of an elastically deformable material (e.g., rubber). The crimp (108) may be made of a plastically deformable material (e.g., metal). The sealing member (106) and the crimp (108) may be configured to be pierced by a needle of access to the interior (40) of the cartridge (134) through the open distal end (212). The elastic sealing member (106) may be configured to seal around an opening formed by a needle to maintain a fluid and contamination seal at the distal end (212). Together, the sealing member (106) and the crimp (108) form a cartridge cap (72) ("8-I seal"). The open proximal end (214) may be fluidly sealed by a stopper member inserted therein (see below) to fluidly seal (along with the sealing member (106) at the distal end) the interior (40g) of the cartridge (134). A sealed cartridge can contain an injectable substance (e.g., a medication) be transported and stored for usage.

Figure 6A:
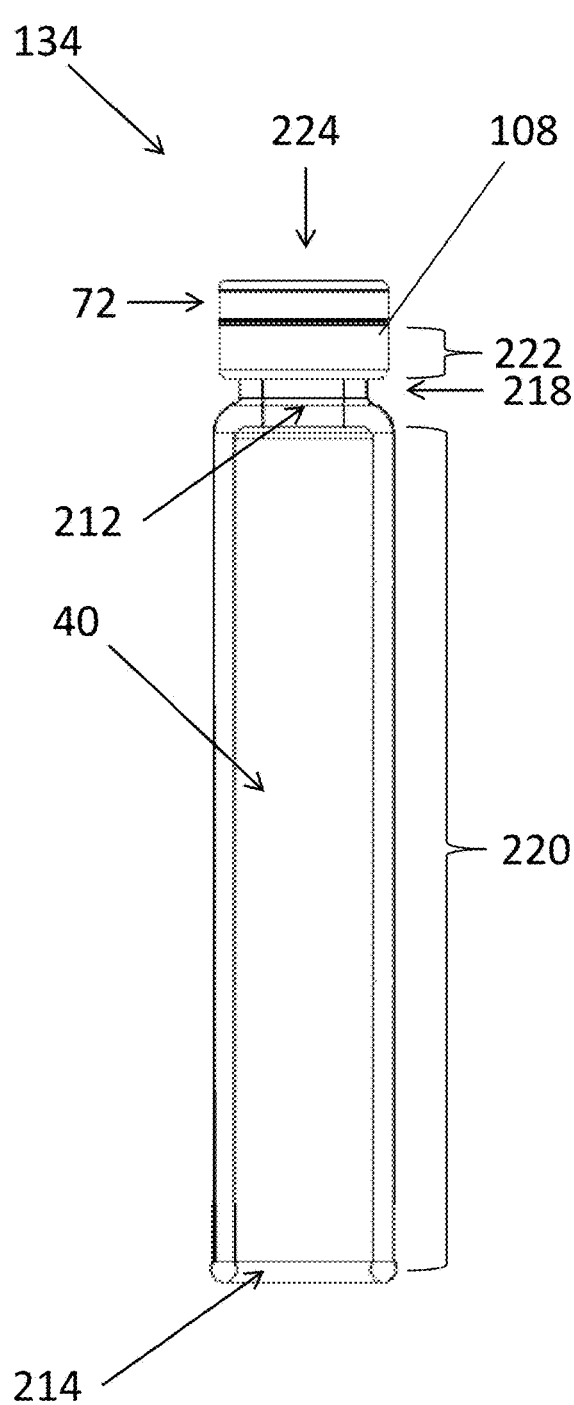
Figure 6B:
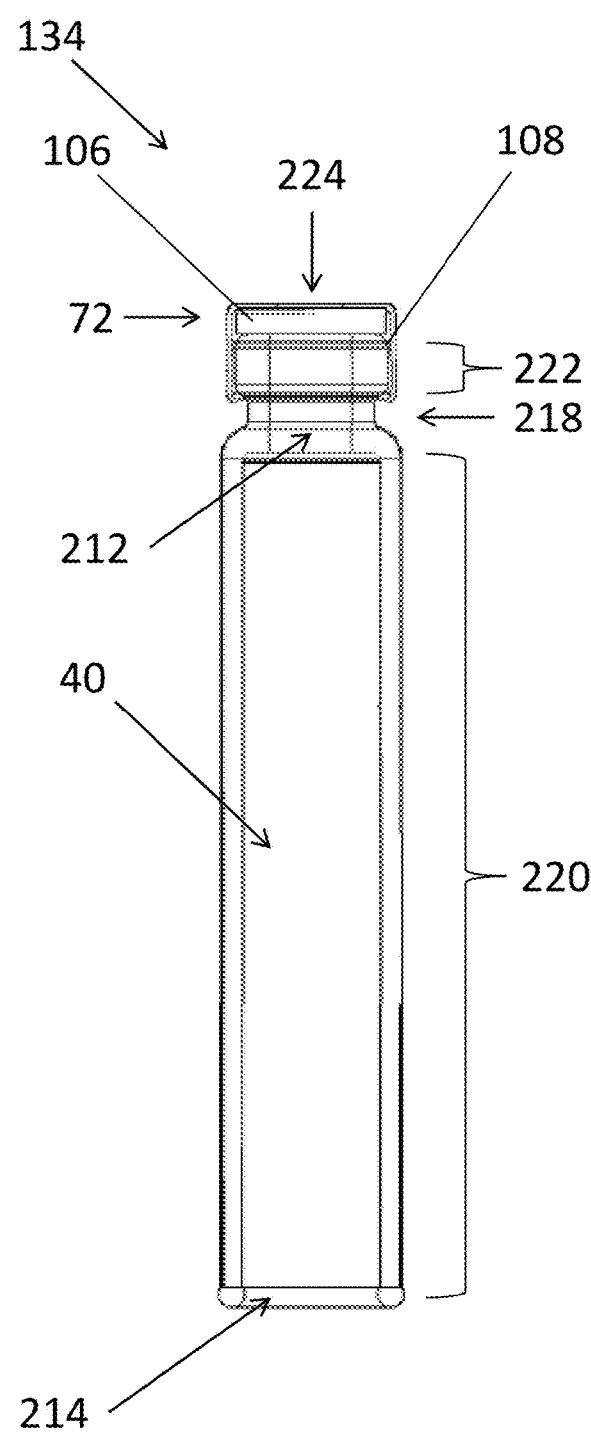

The cartridge (134') in FIGS. 6C and 6D is almost identical to the cartridge (134) in FIGS. 6A and 6B. The one difference is that the cartridge (134') in FIGS. 6C and 6D also has a flange (226) formed at the proximal end of the cartridge (134'). The flange (226) is configured to facilitate injection by providing a distally facing surface against which proximally directed force may be applied (e.g., to move the cartridge (134') proximally relative to a stopper member). For instance, the flange (226) may be manipulated by or interfaced between the index and middle fingers of an operator, for example, while a thumb of the operator is interfaced with a proximal end of a plunger assembly. In other embodiments, the flange (226) may be operatively coupled actuating surfaces of "pens" or "autoinjectors."

Exemplary Cartridge and Exemplary Syringe

Figure 7A:
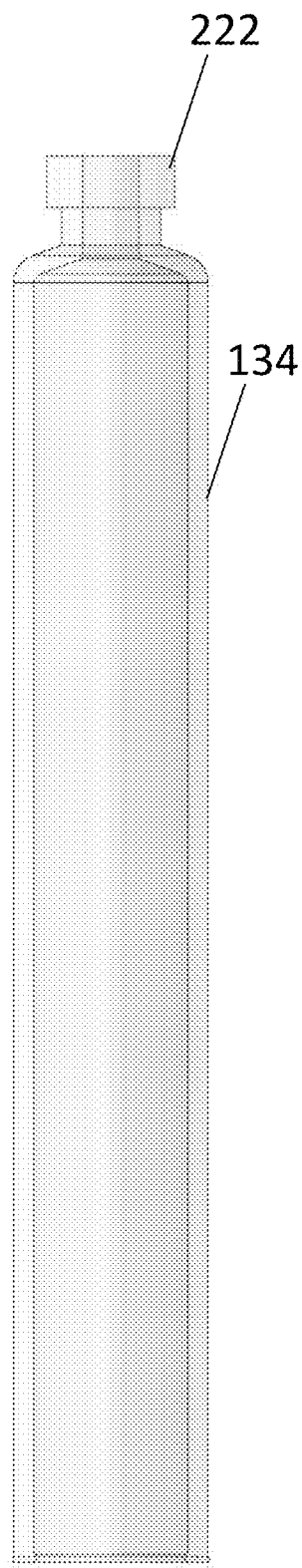
FIGS. 7A and 7B depict a cartridge and a syringe body according to two embodiments.
Figure 7B:
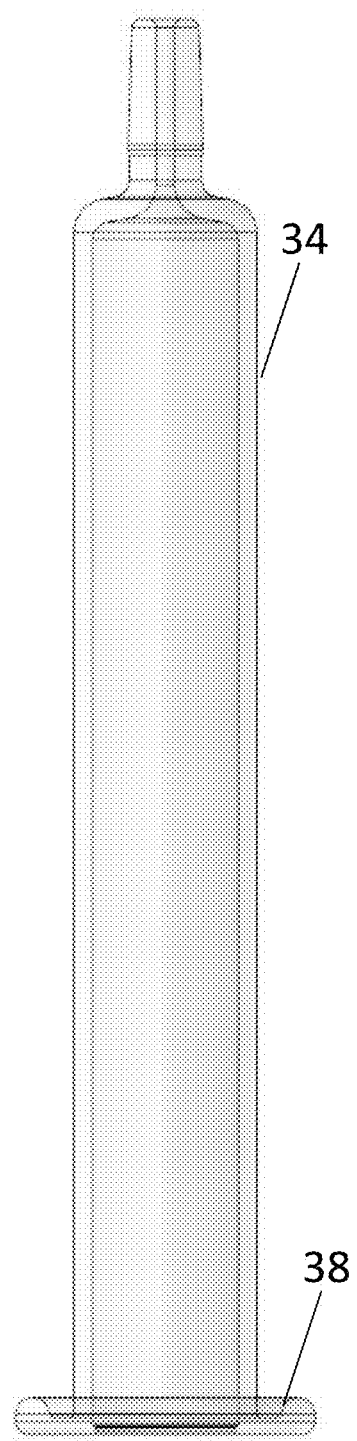

FIGS. 7A and 7B respectively depict similar sized cartridge (134) and syringe body (34) according to two embodiments. Both the cartridge (134) and the syringe body (34) may be made from glass. While the syringe body (34) is configured for use in an injection system, the cartridge (134) is configured for both use in an injection system and storage of substances (e.g., medications). This results in several differences between cartridges (134) and syringe bodies (34). For instance, while the proximal end of the syringe body (34) includes a conventional integral syringe flange (38), the proximal end of the cartridge (134) does not include an integral flange. Further, while the distal end of the syringe body (34) includes a Luer taper configured to allow snapping engagement of a needle coupling assembly (not shown), the distal end of the cartridge (134) includes a flange (222) configured for securing a conventional cartridge seal (not shown). Conventional cartridge seals include an elastically compressible sealing member at least partially surrounded by an elastically deformable closure (e.g., an aluminum ring) (see FIGS. 6A-6D). As shown in FIGS. 7A and 7B, the distal opening of the cartridge (134) is significantly larger than the corresponding distal opening of the syringe body (34). This provides more opening area for liquid filling or for airflow in the case where lyophilization of the drug into a dried state is desired, but renders accurate attachment of the needle coupling assembly more difficult.

Exemplary Safe Injection System

Figure 8A:
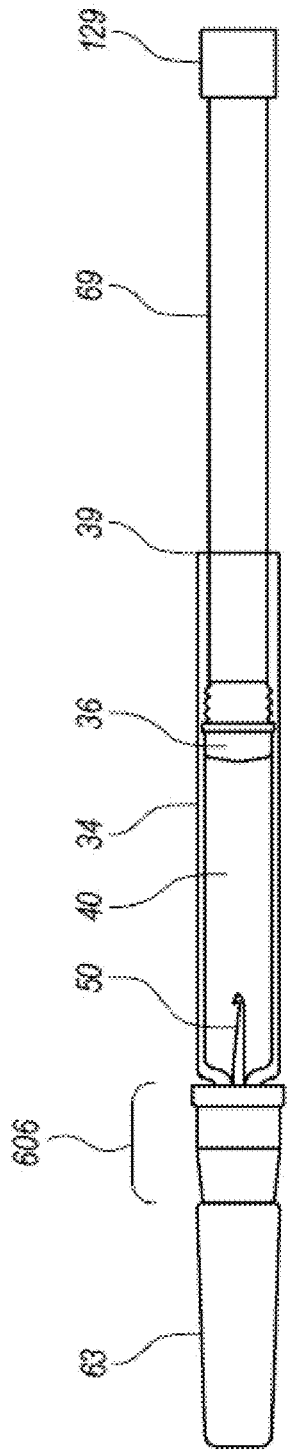
FIGS. 8A-8S depicted a safe injection system including a cartridge according to various embodiments.

Referring to FIGS. 8A-8N, one embodiment of an injection system may be utilized with pens, autoinjectors, or other "reusable" or "disposable" housing interfaces, such as those depicted in FIGS. 8C, 8F, and 8O-8R.

Figure 8B:
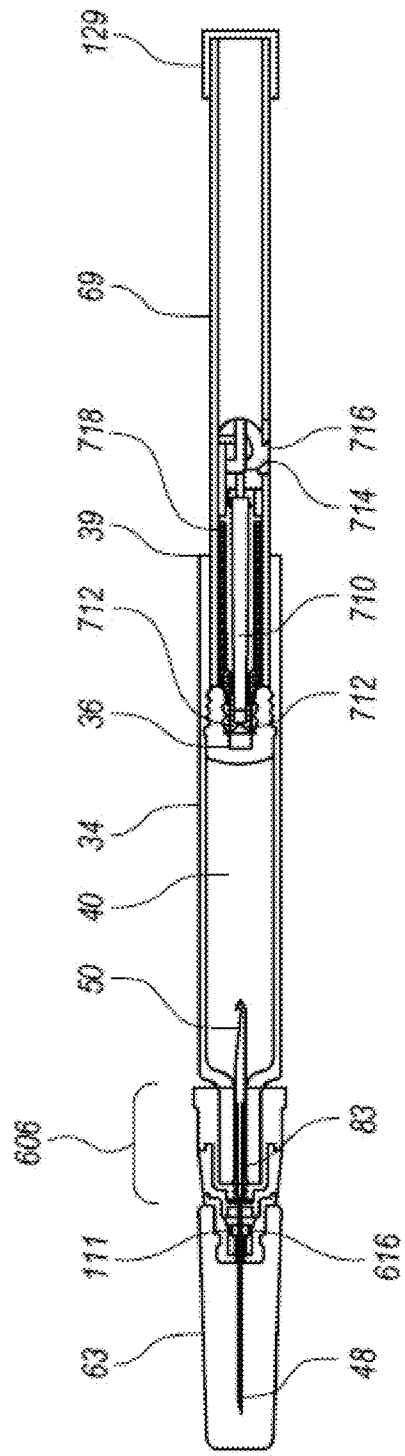
FIGS. 8C, 8F, and 8O-8R depict the safe injection system as used in an autoinjector according to various embodiments.
Figure 8Q:
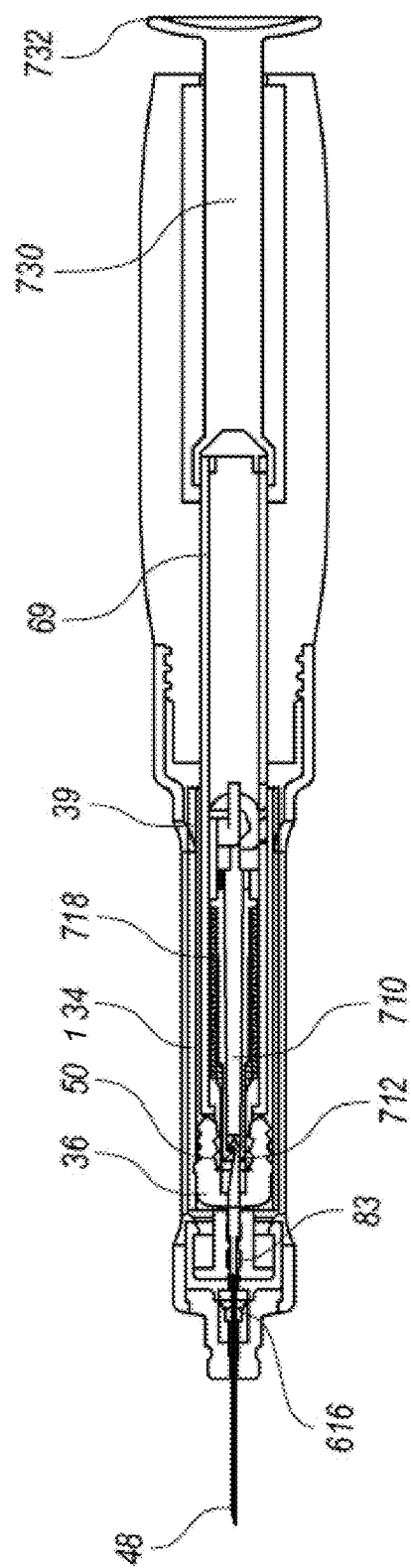

Referring to FIGS. 8A-8B, a side and a cross sectional view of a safe injection system are shown, with a conventional off-the-shelf pre-filled syringe body (34) defining a medicine chamber (40), a stopper member (36) occluding the proximal end of the medicine chamber (40), and a needle coupling assembly (606) disposed at the distal end of the medicine chamber (40) with a needle cover member (63) installed for storage. The safe injection system controls exit of medicine from the chamber (40) distally subject to insertion of a plunger assembly relative to the syringe body (34) by a user. The plunger assembly includes the stopper member (36), a plunger housing member (69) and a proximal end (129) configured to be interfaced with a plunger coupling member (730) distal end of a pen or autoinjector housing configuration (see below). The proximal end (129) of the plunger assembly may be configured to interface with an operator's thumb with a flange (732, see FIG. 8C) and with the distal end of a pen or autoinjector (730) to allow one cartridge or syringe to be administered by either a pen, an autoinjector, or an operators thumb.

As shown in the assembly view of FIG. 8C, the configuration of FIG. 8A may be at least temporarily housed within the pen, or autoinjector housing assembly; the depicted pen or autoinjector housing assembly comprises a distal housing portion (726) defining a window (724) therethrough to visualize the injection components therein; a proximal housing portion (728) is movably coupled to a plunger coupling member (730), the distal portion of which is removably coupleable to the plunger housing (69) proximal end (129); a plunger manipulation interface (732) is coupled to the proximal end of the plunger coupling member (730). FIGS. 8D, 8E, and 8F illustrate similar configurations as those of FIGS. 8A, 8B, and 8C, respectively, with the protective needle cap (63) removed, and the needle distal tip (48) ready for injection.

Returning to FIGS. 8A-8B, for example, a safe injection system comprises a conventional syringe body (34), fitted with a stopper member/stopper member (36) configured to be pierced by needle proximal end (50) at an appropriate time to assist with needle retraction; this stopper member (36) is coupled to a proximal end (129) by a plunger housing member (69) defining an inner volume occupied by various other portions of the assembly, as described below, which are configured to retract the needle at an appropriate time in the sequence of use. The syringe body (34) does not include a flange which may facilitate optional usage with in pens, autoinjectors, or other "reusable" or "disposable" housing interfaces. The safe injection system includes a needle coupling assembly (606), having a needle joining member (83), a distal needle tip (48), a needle latch (616), and a necked-down or radially-reduced portion (111) (i.e., "groove") of the needle joining member (83), which are described in U.S. provisional patent application Ser. No. 62/416,102, which was previously incorporated by reference herein. Other embodiments may comprise Luer type needle assembly coupling to the syringe body (34). FIGS. 8A and 8B illustrate pre-utilization assemblies with a needle cover (63) in place to mechanically isolate the distal needle tip (48). Referring to FIGS. 8D and 8E, the needle cover (63) has been removed and the assembly is readied for injection into a patient.

Although not shown, after the distal needle end (48) has been inserted or stabbed into a tissue structure of a patient, the plunger assembly proximal end (129) may be briefly pulled away from the syringe body (34) to "aspirate" or check to confirm that the needle distal tip (48) has not come to rest within an unwanted tissue structure portion, such as a vessel. For example, if the distal needle tip (48) has come to rest within a vessel, upon slightly pulling out the stopper member (36), a small marking of blood of the patient is likely to appear within the medicine chamber (40), and the operator can see this and reposition the distal needle tip (48).

Referring to FIGS. 8G and 8H, with the desired distal needle tip position optionally confirmed, the plunger assembly proximal end (129) is inserted relative to the syringe body (34) and the medicine is expelled out of the medicine chamber (40), through the needle tip (48), and into the patient (not shown). FIG. 8H illustrates a cross sectional view of the configuration of FIG. 8G.

Referring to FIGS. 8I and 8J, with complete seating of the stopper member (36) into the syringe body (34), the needle proximal end (50) is stabbed through the stopper member (36). Elastic deformation of the material comprising the stopper member (36) allows the stopper member (36) to reach the bottom of the syringe body (34) to expel all of the medicine, and trigger an energy-storing member (718) to retract the needle while accounting for geometric variation of syringe body (34) and other components due to manufacturing and assembly tolerances. In other embodiments, a spring member provides the elastic deformation required to ensure the stopper member (36) reaches the bottom. For instance, the embodiment depicted in FIGS. 8O and 8P include a space (720) which is eliminated by a spring in an auto injector in order to allow the stopper member (36) to reach the bottom. Returning to FIG. 8J, a needle retention feature (712) is configured to prevent pull-out of the needle proximal end (50) once it has been stabbed into and captured by the needle retention feature (712). The capturing interaction between the needle retention feature (712) and a proximal end harpoon of the needle proximal end (50) is configured to allow relatively easy motion (using less force) in the compressive/coupling direction (i.e., during the stabbing-in motion with the proximal end harpoon of the needle proximal end (50)), and relatively difficult motion (withstanding more force) in the axial tension/decoupling motion (i.e., with a needle retracting load from the plunger assembly to pull the needle distal tip (48) into a safe configuration).

With complete insertion of the stopper member (36), the needle latch (616) is configured to become unseated from its previous latched position in the groove (111) on the needle joining member (83), as shown in FIG. 8J, to allow for retraction of the needle. Concomitantly, as is shown in the progression from FIGS. 8I/8J to FIGS. 8K/8L, the needle proximal end (50) is configured to directly abut or compress against an unlatching member (710) or rod that is configured to allow a rotatable latching member (714) to be positioned or configured into either of two states.

The first configuration of the rotatable latching member (714), shown in FIG. 8I and associated cross section FIG. 8J, is the "latched" condition, where the rotatable latching member (714) is retained in the position shown in FIG. 8J by a proximal feature comprising the proximal aspect of the unlatching member (710). In this latched condition, a load generated by a compressed energy-storing member (718), such as a spring, is reacted/opposed by the geometric state of the latching member (714), maintaining the compressed state of the energy-storing member (718).

The second configuration of the rotatable latching member (714), shown in FIG. 8K and associated cross section FIG. 8L, may be termed the "unlatched" condition wherein the unlatching member (710) has been moved more proximally with loading from the needle proximal end (50) to cause the rotatable latching member (714) to be free to rotate. In this second configuration, with rotation of the rotatable latching member (714) out of the lock interface window (716) as shown in FIG. 8L, the load generated by the compressed energy-storing member (718) is not reacted by the rotatable latching member (714), and the energy-storing member (718) is free to expand longitudinally, as shown in FIG. 8M and associated cross section FIG. 8N, thereby pulling the needle retention feature (712) and inter-coupled needle spine assembly (76) proximally, which retracts the needle spine assembly (i.e., the needle proximal end (50), the needle joining member (83), and the needle distal end (48)) at least partially through the stopper member (36) where the needle distal tip (48) is safely encapsulated in at least a portion of the plunger housing member (69) and/or inside at least a portion of the needle coupling assembly (606). As such, the rotatable latching member (714) is a "living hinge."

Thus referring again to FIG. 8L, in the unlatched configuration, the unlatching member (710) is moved proximally and the rotatable latching member (714) is configured to rotate from a latched position, wherein the rotatable latching member (714) is seated within a lock interface window (716), and wherein this interfacing of the latch position maintains the energy storage member (718), which may comprise a spring, in a stored configuration, to an unlatched position, wherein the rotatable latching member (714) is rotated slightly out of the lock interface window, as shown in FIG. 8K, and the cross sectional view of FIG. 8L, to free the energy storage member (718) to accelerate and move the stopper member (36) to the right as the potential energy stored in the energy storage member (718) is released, thereby pulling the intercoupled needle proximal end (50) along with it, as shown in FIG. 8M and the cross sectional view of FIG. 8N, such that the needle distal tip (48) becomes safely encapsulated within the stopper member (36) and/or the plunger housing member (69) (i.e., into a protected configuration). Once in this configuration, the needle coupling assembly (606) preferably is configured to prevent any further re-insertion of the distal needle tip (48) relative to the syringe body (34); in other words, needle tip re-exposure is prevented with such a safety configuration.

In one embodiment the stopper member (36) may be solid, not having any pre-formed through-holes to facilitate transection of the needle proximal end (50). As shown, for example, in FIG. 8N, complete retraction of the needle through the stopper member (36) requires the needle to penetrate the stopper member (36). To pull the needle through the stopper member (36) without losing "grip" on the needle proximal end (50), the penetration force of the needle through the stopper member (36) generally must be low enough so as not to exceed the "gripping load" provided by the interface that has been formed between the needle proximal end (50) and the needle retention features (712) with stabbing of the needle proximal end (50) through the stopper member (36). With one embodiment, experimentation has shown that the penetration force between the needle spine assembly and the stopper member (36), or the needle joining member (83) and the stopper member (36), is between about 1 lb. and about 4 lbs., depending upon the rubber or elastomeric material used to manufacture the stopper member (36), or the plastic or metal used to manufacture the needle joining member (83). To further minimize resistance as the needle spine assembly (76) is pulled through the elastomeric stopper member (36), in one embodiment it is desirable to create a chamfered geometry on the proximal geometric aspects of the needle joining member (83).

As was discussed above in reference to FIGS. 8I and 8J, in the embodiment of FIGS. 8A-8N, the elastomeric material comprising the stopper member (36) is utilized to assist in dealing with slight geometric tolerances which may be present due to manufacturing, assembly, temperature, or other factors. In use, the operator feels the full insertion position of the stopper member (36) relative to the syringe body (34) coming by an increased insertion load required to continue inserting the stopper member (36). The operator may be trained to continue such insertion against such increasing insertion resistance load until a "click" sound is heard, which signifies that the needle latching mechanism (616) has been triggered, thereby releasing the needle longitudinally relative to the syringe body (34) so that it may be retracted. In one embodiment, the "click" sound is caused by rotation of the rotatable latching member (714), which is driven by the energy storage member (718). While the embodiment depicted in FIGS. 8G to 8N include only a syringe, the syringe may be used with pens, autoinjectors, or other "reusable" or "disposable" housing interfaces as depicted in FIGS. 8C and 8F.

Exemplary Cartridge Safe Injection Systems

The syringe body (34) in the embodiment depicted in FIGS. 8A-8N may be constructed from a glass material, and may comprise a Luer taper on its distal end for attachment of the staked needle coupling assembly (606). In other embodiments, such as the one depicted in FIGS. 8O-8S, a cartridge (134) may be utilized, which has a glass flange configuration, similar to that on a medicine vial. Such a glass cartridge (134) is shown in FIGS. 9A-9B and 10A-10D, described below. The glass cartridge (134) includes a rubber seal (see e.g., 106 in FIG. 6B) and an aluminum crimp (108, FIG. 10A) to seal the medicine inside the glass cartridge (134). With such an embodiment, a pen, autoinjector, or reusable or disposable injection assembly similar to that shown in FIGS. 8O-8R may be snapped over the glass flange to seal the medicine in the cartridge (134). In other embodiments, the aluminum crimp (108) may be replaced with a plastic needle housing.

Figure 8R:
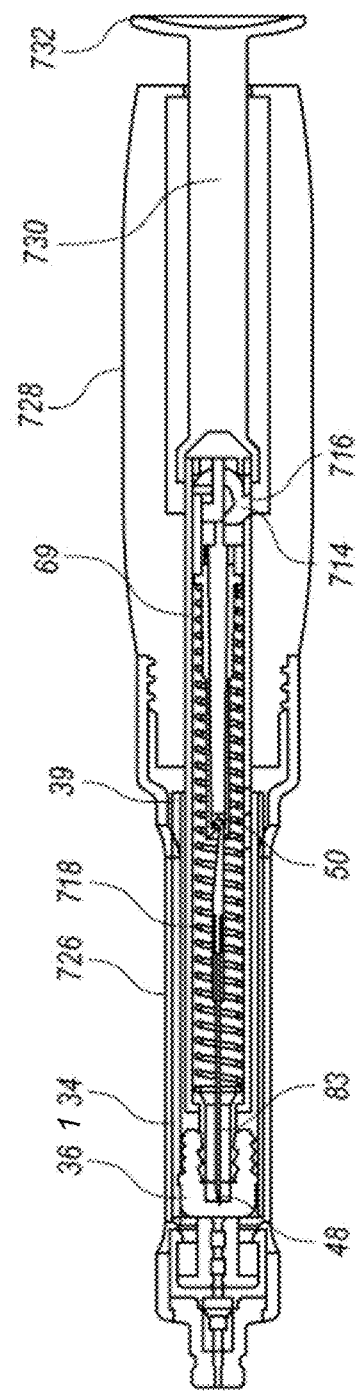

Referring to FIGS. 8O-8R, a pen, autoinjector, or reusable or disposable injection assembly including a cartridge body (134) is operated as described in relation to FIGS. 8G-8N, with the exception that the manual manipulation by the user is not directed to the injection assembly, but is rather directed to the pen or autoinjector housing, which is at least temporarily coupled to the cartridge body (134). Upon full insertion of the stopper member (36), the needle becomes unlatched and is captured proximally by the needle retention feature (712, FIG. 8Q), and release of the proximal rotatable latch member (714) causes retraction of the needle into a protected configuration (by a load from the energy-storing member (718)), as shown in FIG. 8R, leaving a safely used and disposable cartridge body (134), as shown in FIG. 8S. In the case of an auto injector, a drug may be expelled by a compressed spring acting on the plunger housing member (69).

An exemplary pen injector is shown in FIG. 8O or 8R for reference. The pen injector shown is for illustrative purposes and includes the manual application of force to the plunger rod to expel the medicine from the medicine chamber into the patient. Alternatively, the injector assembly could also incorporate automatic mechanisms such as a coiled spring, motor, ball screw, or linear actuator for the automatic delivery of the drug into the patient once commanded by the patient or caregiver. These autoinjectors function similarly to the syringe or the pen injectors to deliver the medicine to the patient, with the exception of the patient is not tasked with continuous application of force to the plunger rod. A motor or mechanism applies the force for the patient. The autoinjector may be configured to be disposable, reusable, or a combination thereof. The force application mechanisms may be configured to be driven by a battery, spring, or other energy storage mechanism. The automatic needle retraction technologies described herein may be configured to be actuated by the auto injector plunger mechanisms.

Referring to FIGS. 9A-9B, a method of assembling a medicine cartridge (134) with a retractable safety needle (810) is shown. As shown in FIG. 9A, the medicine cartridge (134) includes a flange portion (222) on its distal end. This flange portion (222) is configured to couple to a distal seal (814). The distal seal (814) has a proximal facing cartridge sealing surface (816) and a proximally projecting cartridge sealing surface (818). The interior of the distal seal (814) also includes at least one sealing gland (820) for sealing against the external surfaces of the needle. The needle coupling assembly (606) of the retractable safety needle (810) also includes a snap over interface (822) for coupling the needle coupling assembly (606) to the flange portion (222) of the cartridge (134).

Referring to FIG. 9B, the assembled medicine cartridge (134)/retractable safety needle (810) is shown in a configuration for delivery to the end user. The needle coupling assembly (606) and intercoupled distal seal (814) is assembled onto the glass cartridge 800. The medicine is loaded inside the medicine chamber (40). And the stopper (36) is placed holding the medicine in the medicine chamber (40) for storage and shipping to the customer. The plunger rod including the retraction mechanism may be added before or after delivery to the end user, prior to assembly inside the injector housing.

Figure 10A:
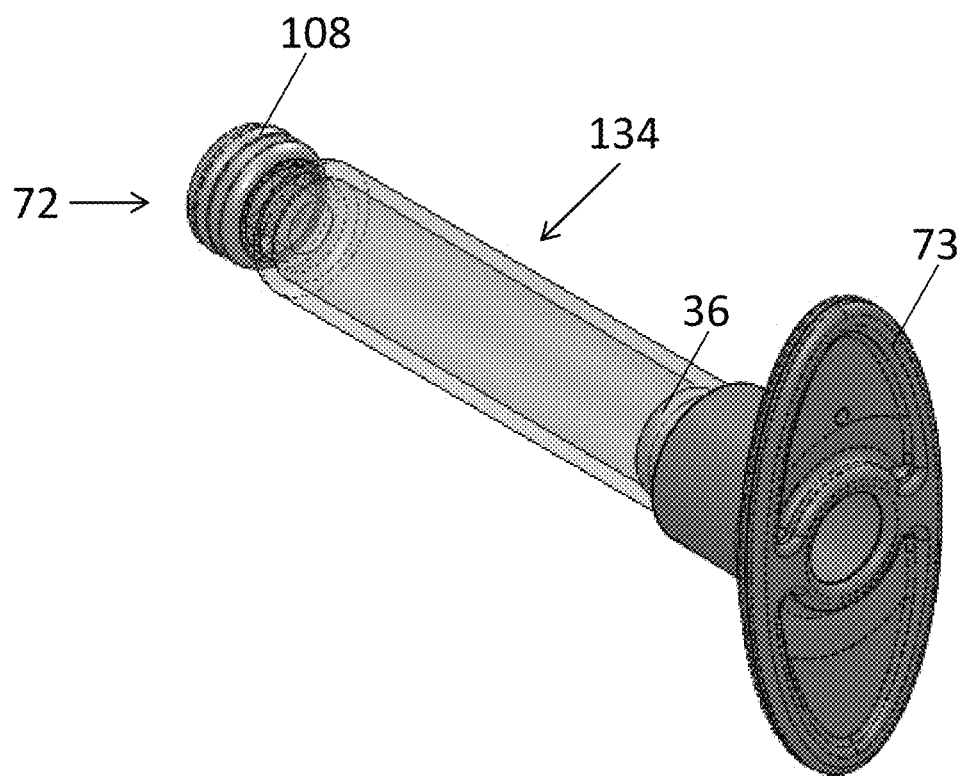
FIG. 10A depicts a cartridge for use with a safe injection system according to one embodiment.
Figure 10B:
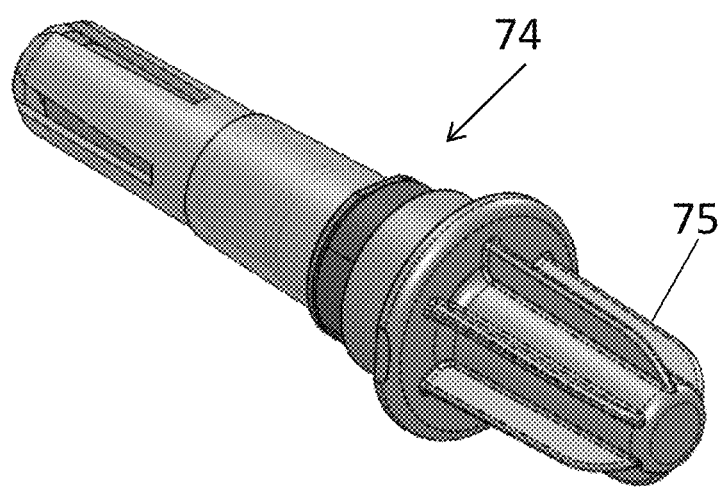
FIG. 10B depicts a needle hub assembly for use with a safe injection system according to one embodiment.
Figure 10C:
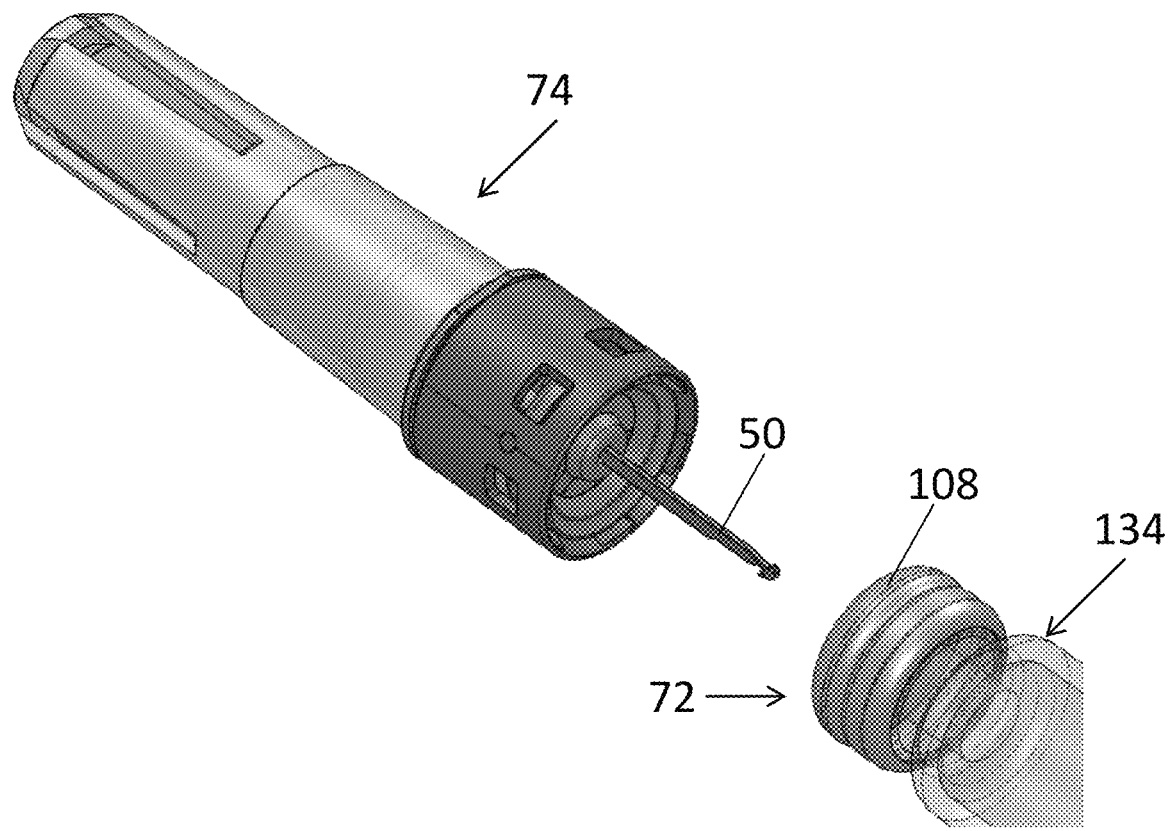
FIG. 10C depicts a needle hub assembly and a cartridge for use with a safe injection system according to one embodiment, with the needle hub assembly and the cartridge positioned for coupling.
Figure 10D:
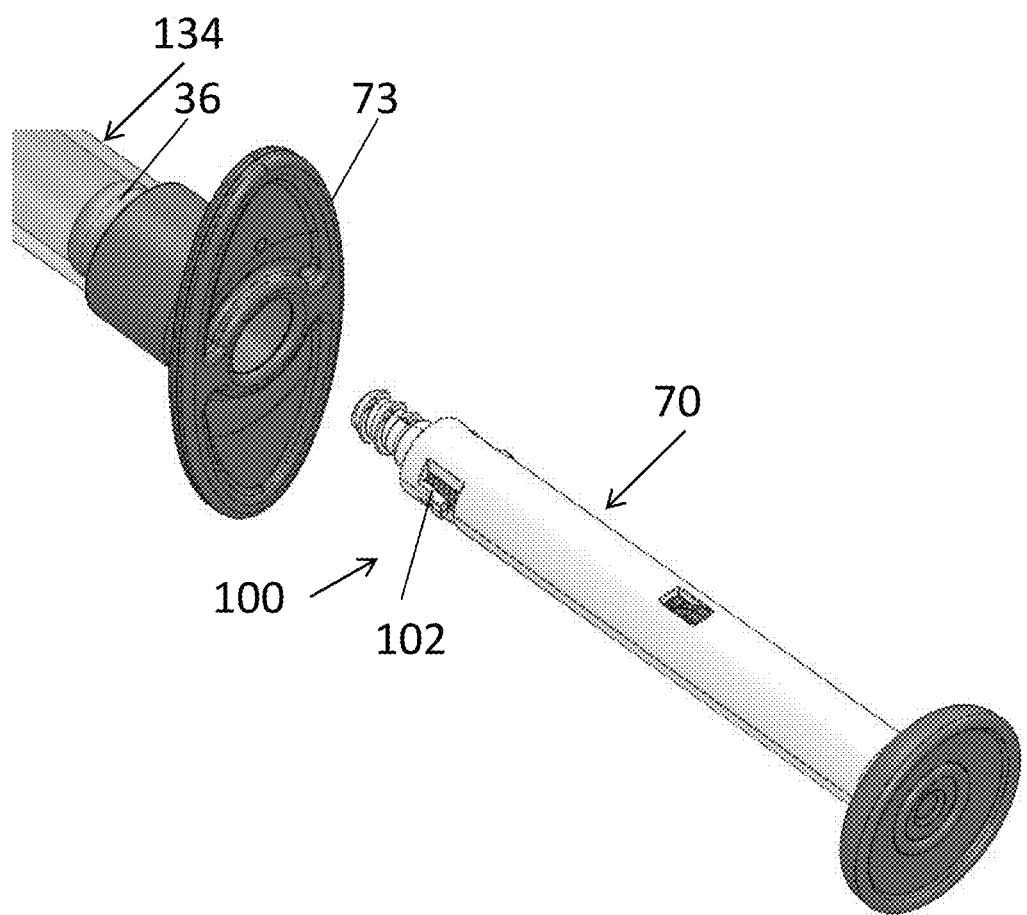
FIG. 10D depicts a cartridge and a plunger rod for use with a safe injection system according to one embodiment, with the cartridge and the plunger rod positioned for coupling.

Referring to FIGS. 10A-10D, various aspects of another embodiment of a cartridge safe injection system are illustrated. FIG. 10A depicts a cartridge (134) that is assembled with a cartridge cap (72), a drug and a stopper (36) inside of the cartridge (134), and a finger flange (73). FIG. 10B depicts a needle hub assembly (74) including a proximal cap (75) covering the needle assembly proximal end (50, see FIG. 10O). FIG. 10O depicts the needle hub assembly (74) with the proximal (75) removed. In this configuration, the needle proximal end (50) can be inserted through the cartridge cap (72) and into the cartridge (134). FIG. 10D depicts a plunger rod (70) in a position relative to the cartridge (134) to be inserted into the finger flange (73) and screwed into the stopper (36).

Further depicted in FIG. 10D is a plunger rod removal brake (100) which is constructed of at least one externally projecting surface (102) that interlocks with a distally facing surface on the finger flange (73) to prevent removal of the plunger rod (70) after the injection has been performed. To minimize the length of the plunger rod (70), it may be desirable to retract the needle only behind the distal most end of the needle hub assembly (74). In this case, the sharpened needle tip (48) is not retracted into the plunger rod (70) as the plunger rod (70) is too short to accommodate the whole needle length. The plunger rod (70) must be prevented from being removed from the syringe body (34) or cartridge (134) after the injection has been performed (e.g., using the plunger rod removal break (100)) to prevent exposure of the needle tip (48). The externally projecting surfaces (102) may be configured to elastically deform radially when the externally projecting surfaces (102) is retracted from the glass barrel of the cartridge (134) to engage the distally facing surface of the finger flange (73) and prevent removal of the plunger rod (70) from the finger flange (73). Alternatively, the externally projecting surfaces (102) may be configured to engage the distally facing surface of the finger flange (73) without requiring elastic deformation. In this case, the externally projecting surfaces (102) are configured to be "self-energizing", whereby the proximal movement of the plunger rod (70) causes the surfaces (102) to become engaged with the finger flange (73). Further pulling of the plunger in a proximal direction causes the surfaces (102) to deform such that more engagement occurs between the externally projecting surfaces (102) and the finger flange (73), strengthening the grip between the two components, preventing removal of the plunger rod (70) from the finger flange (73).

Figure 10G:
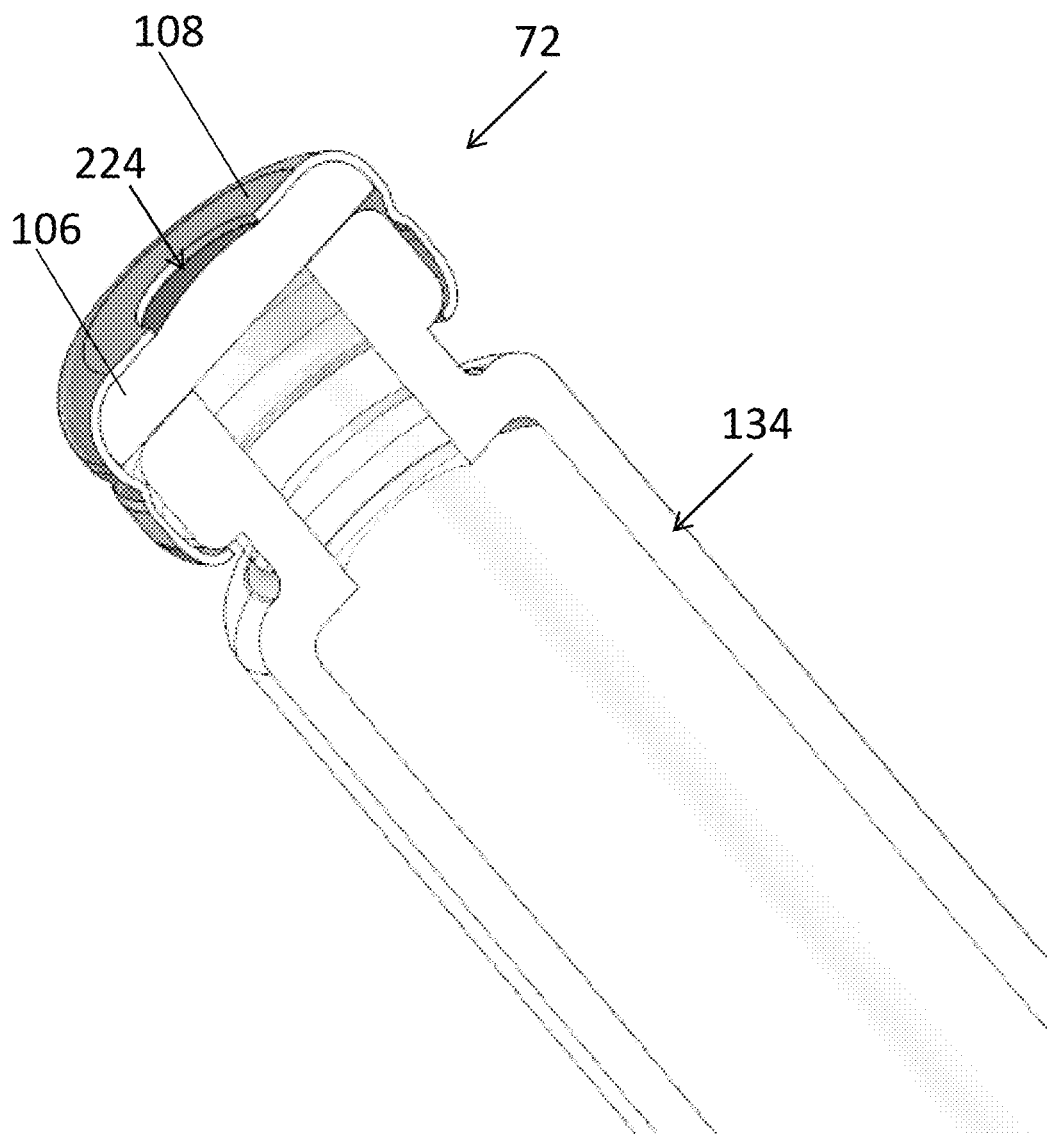
FIG. 10G depicts a cartridge for use with a safe injection system according to one embodiment.

Referring to FIGS. 10E-10I, cross sectional views of cartridge safe injection systems are depicted. This embodiment of the cartridge based system includes a cap (72) which is constructed of a rubber cartridge seal (106) which is enclosed within a metal crimp (108). The cap (72) seals the medicine within the cartridge (134). During assembly, a needle hub assembly (74) may be placed over the cap (72), and the needle proximal end (50) of the needle hub assembly (76) may be inserted through the cartridge seal (106). The penetration of the cartridge seal (106) may be performed at the factory prior to being shipped to the user, or may be performed at the point of use. A backup seal (110) may be disposed between the cartridge seal (106) and the needle coupling assembly (606) to take up assembly tolerances between the needle coupling assembly (606) and the cap (72). Alternatively, the backup seal (110) provides a sterility barrier preventing contamination from entering the interior of the needle hub assembly (74) when installed on the cartridge (134). The backup seal (110) may be constructed of a plurality of rubber annular gaskets (as is shown in FIG. 10F), alternatively, the backup seal (110') may be constructed of a single gasket, similar to an O-ring (see FIGS. 10H, 10I, 11E, and 11F). The backup seal (110) shown has a rigid plastic internal support structure. Alternatively, the backup seal (110') may be constructed of a single O-ring type structure with no internal support. A skirt (136) couples the needle coupling assembly (606) onto the cartridge (134), as described below. FIG. 10G depicts a cross sectional view of the cartridge (134) and cap (72) assembly, including the cartridge seal (106), the metal crimp (108), and opening (224), prior to needle penetration during assembly. The embodiment of the cartridge safe injection system depicted in FIGS. 10A-10F is similar to the pen, autoinjector, or reusable or disposable injection system depicted in FIGS. 8O-8S and described above. Examples of such cartridge safe injection systems are described in U.S. patent application Ser. No. 14/696,342, the contents of which have been incorporated herein by reference.

Exemplary Secondary/Backup Seal

Figure 11A:
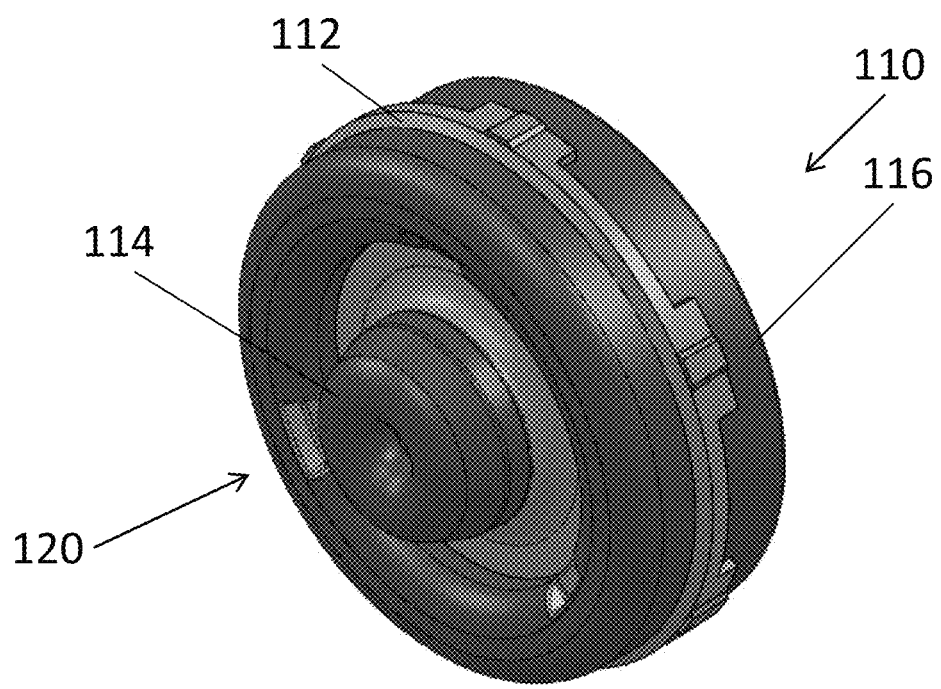
FIGS. 11A-11F depict secondary/backup seals for use with cartridge safe injection system according to various embodiments.
Figure 11B:
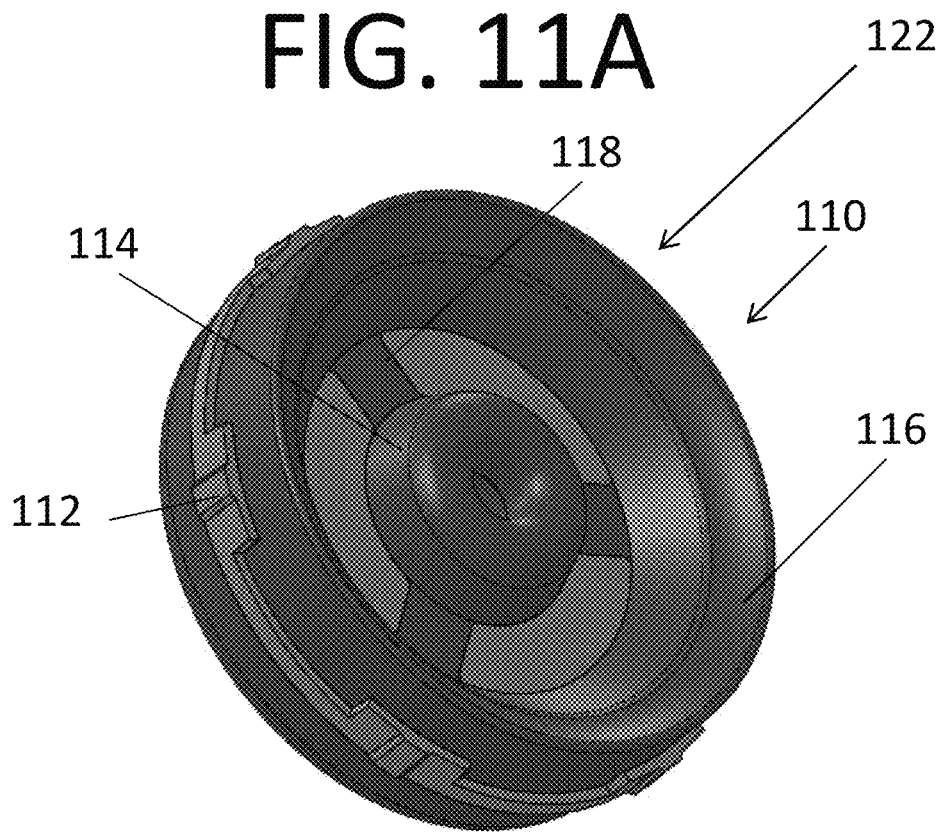

FIGS. 11A-11B illustrate a secondary/backup seal (110) according to one embodiment. The secondary/backup seal (110) may be made of a polycarbonate substrate/disk (112) over-molded with a pair of concentric thermoplastic elastomeric (e.g., Versaflex) gaskets (114, 116). The gaskets include an inner gasket (114) and an outer gasket (116), which are coupled to each other by three pieces of webbing (118). The inner and outer gaskets (114, 116) are mechanically interlocked onto the substrate/disc (112), without the need for chemical adhesives. FIG. 11A shows a distally facing surface (120) of the secondary/backup seal (110). FIG. 11B shows a proximally facing surface (122) of the secondary/backup seal (110).

Figure 11C:
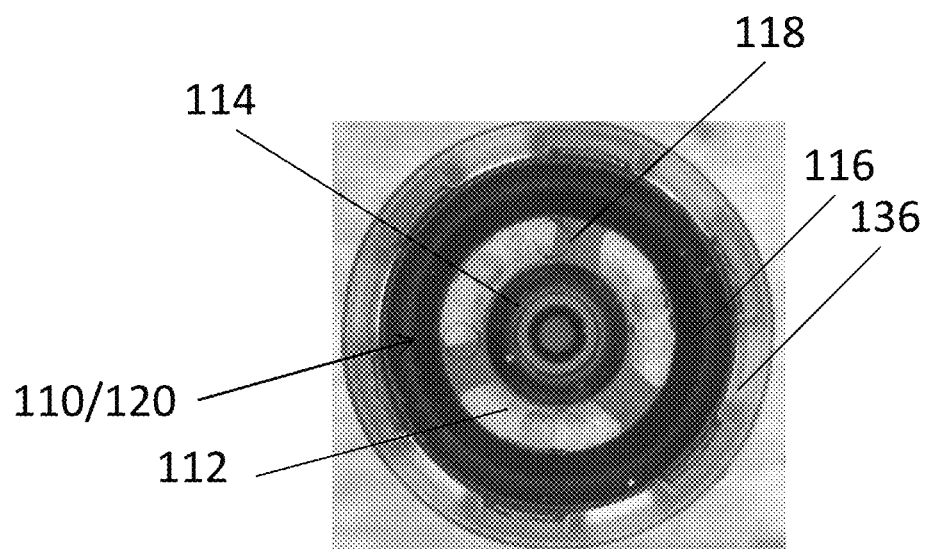
Figure 11D:
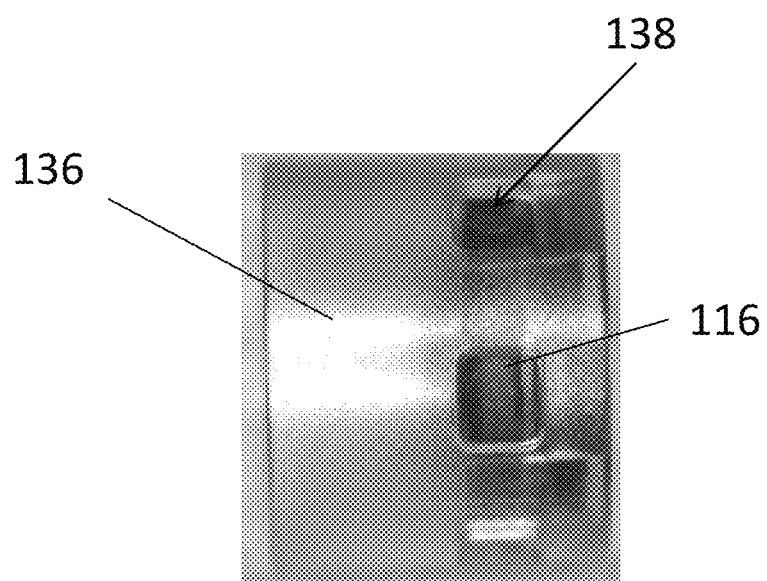
Figure 11E:
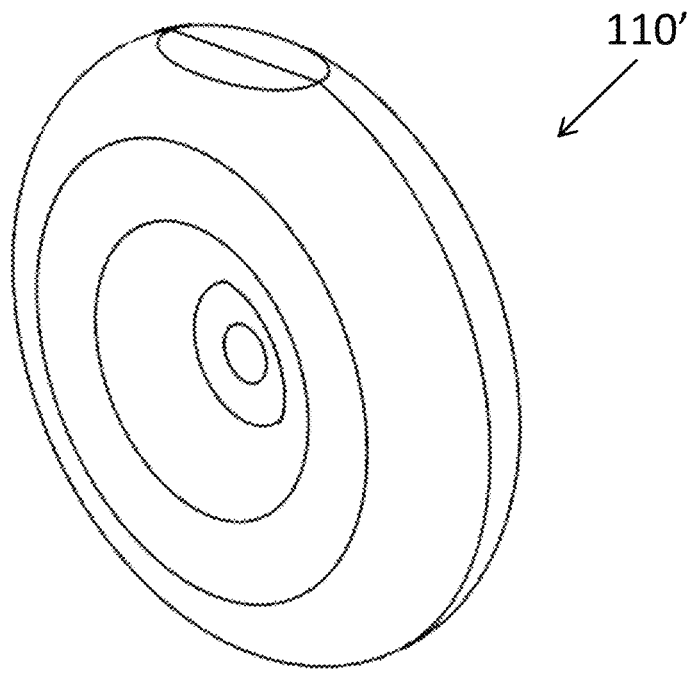
Figure 11F:
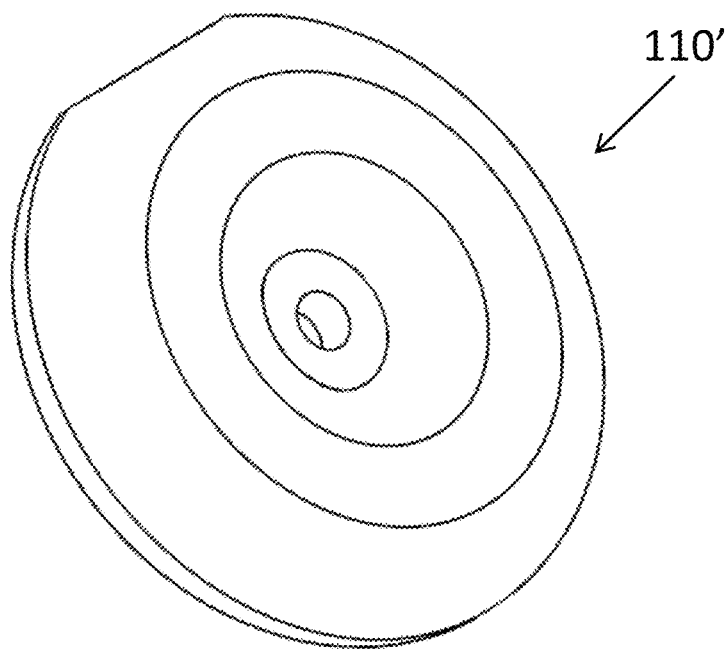

FIGS. 11C-11D depict a secondary/backup seal (110) according to another embodiment. The secondary/backup seal (110) in FIGS. 11C-11D is disposed in a skirt (136) configured to be coupled to the flange of a cartridge. The secondary/backup seal (110) in FIGS. 11C-11D is disposed in a skirt (136) in a distal position (described below). FIG. 11C depicts the distally facing surface (120) of the secondary/backup seal (110). FIG. 11D depicts a side view of the secondary/backup seal (110). Like the secondary/backup seal (110) depicted in FIGS. 11A-11B, the secondary/backup seal (110) depicted in FIGS. 11C-11D includes a polycarbonate substrate/disk (112) over-molded with a pair of concentric thermoplastic elastomeric (e.g., Versaflex) gaskets (114, 116) coupled to each other by three pieces of webbing (118). As shown in FIG. 11D, the skirt (136) includes a plurality of spaces (138). These spaces (138) facilitate insertion of the flange portion (222; see FIG. 9A) of a cartridge (134) into the skirt (136) and movement of the secondary/backup seal (110) therein by facilitating deformation of the skirt (136).

Exemplary Cartridge Safe Injection Systems

Figure 12A:
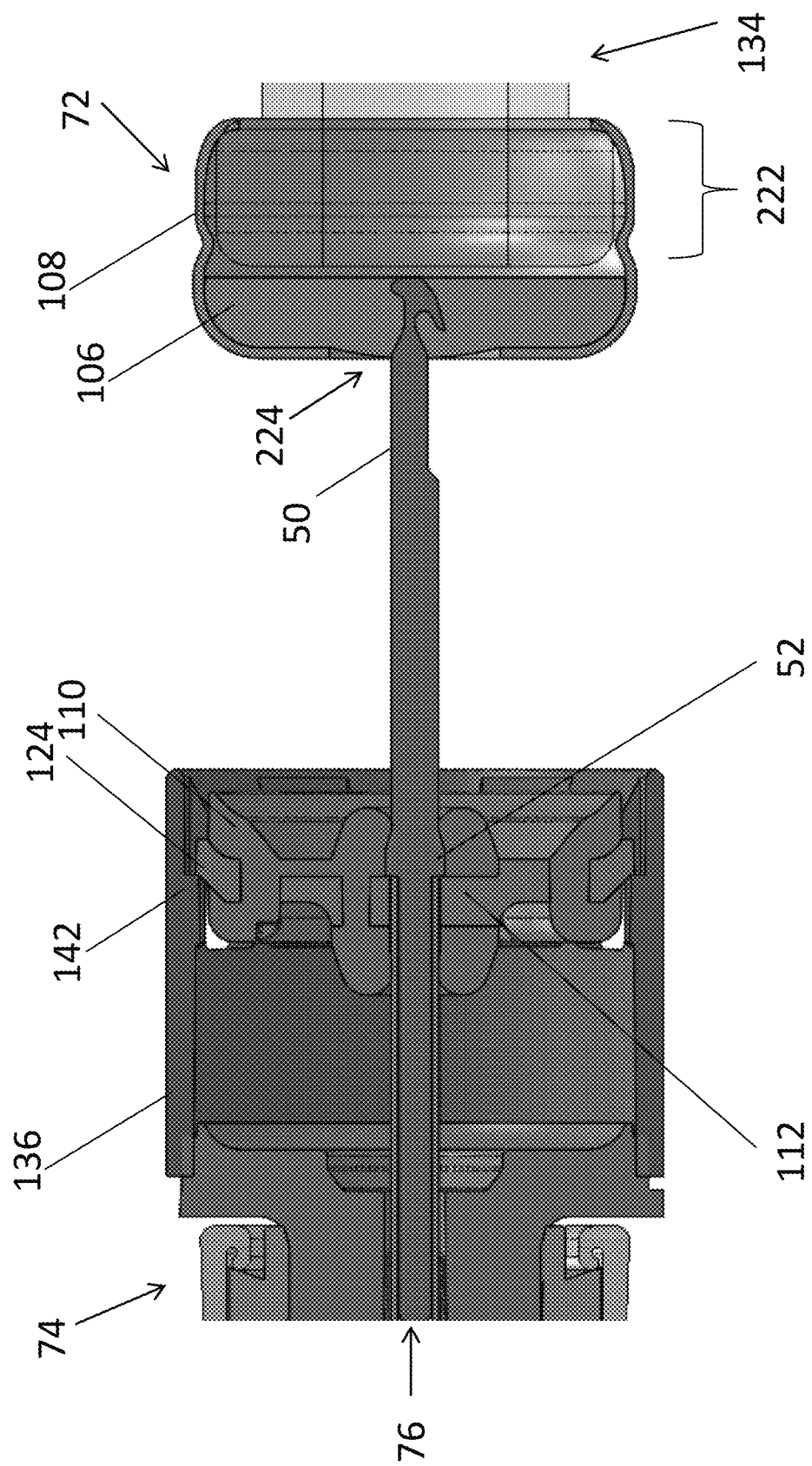

FIGS. 12A to 23E depict partial assembly of a cartridge safe injection system according to one embodiment. The assembly process may be manual with a user inserting a cartridge (134) into a needle hub assembly (74). Alternatively, the assembly process may be automatic with a machine inserting a cartridge (34) into a needle hub assembly (74). FIG. 12A depicts insertion of a needle hub assembly (74) including a secondary/backup seal (110) and a needle proximal end (50) through a cartridge cap (72) and into an interior (40) of a cartridge (134). More particularly, to assemble the cartridge safe injection system, the needle proximal end (50) is inserted through the opening (224) in the crimp (108) and the elastic sealing member (106) into the interior (40) of the cartridge (134).

As the needle proximal end (50) is inserted through the cartridge cap (72), a distally directed force is exerted on the needle spine assembly (76; i.e., the needle proximal end (50), the needle joining member (83), and the needle distal end (48)) through the needle proximal end (50). The distally directed force may push the needle spine assembly (76) in a distal direction and thereby cause the needle latch (616) to become unseated from its previous latched position in the groove (111) on the needle joining member (83), before complete insertion of the stopper member (36), as shown in FIG. 8J. This would cause the needle latch (616) to prematurely disengage and allow for retraction of the needle spine assembly (76). The risk of premature needle latch (616) disengagement during safe injection system assembly is particularly acute with cartridge systems because the needle proximal end (50) must penetrate the crimp (108) and the sealing member (106).

Figure 49:
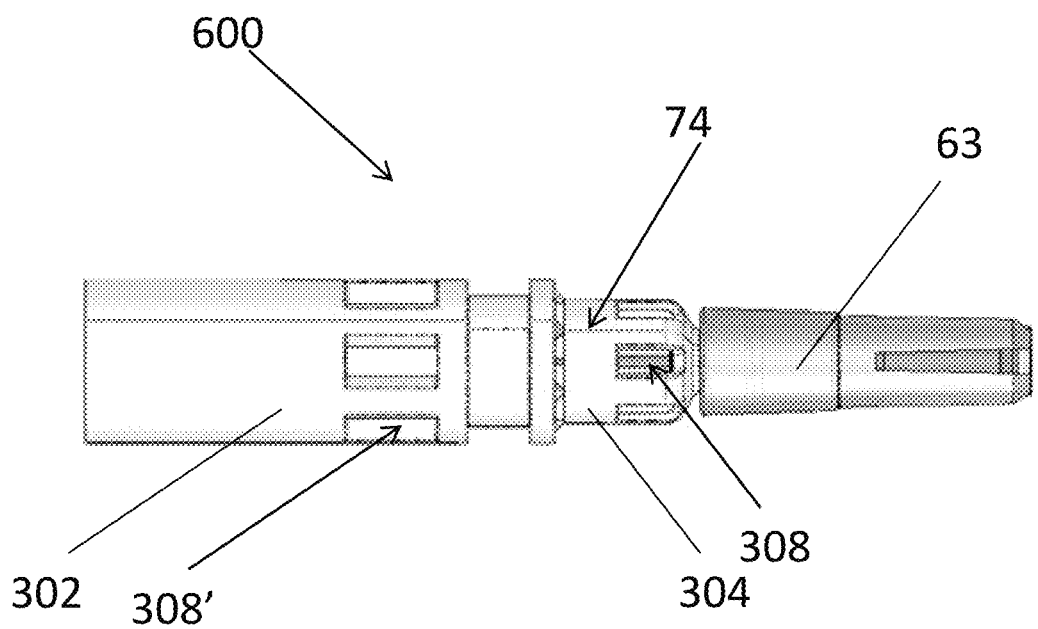
Figure 50:
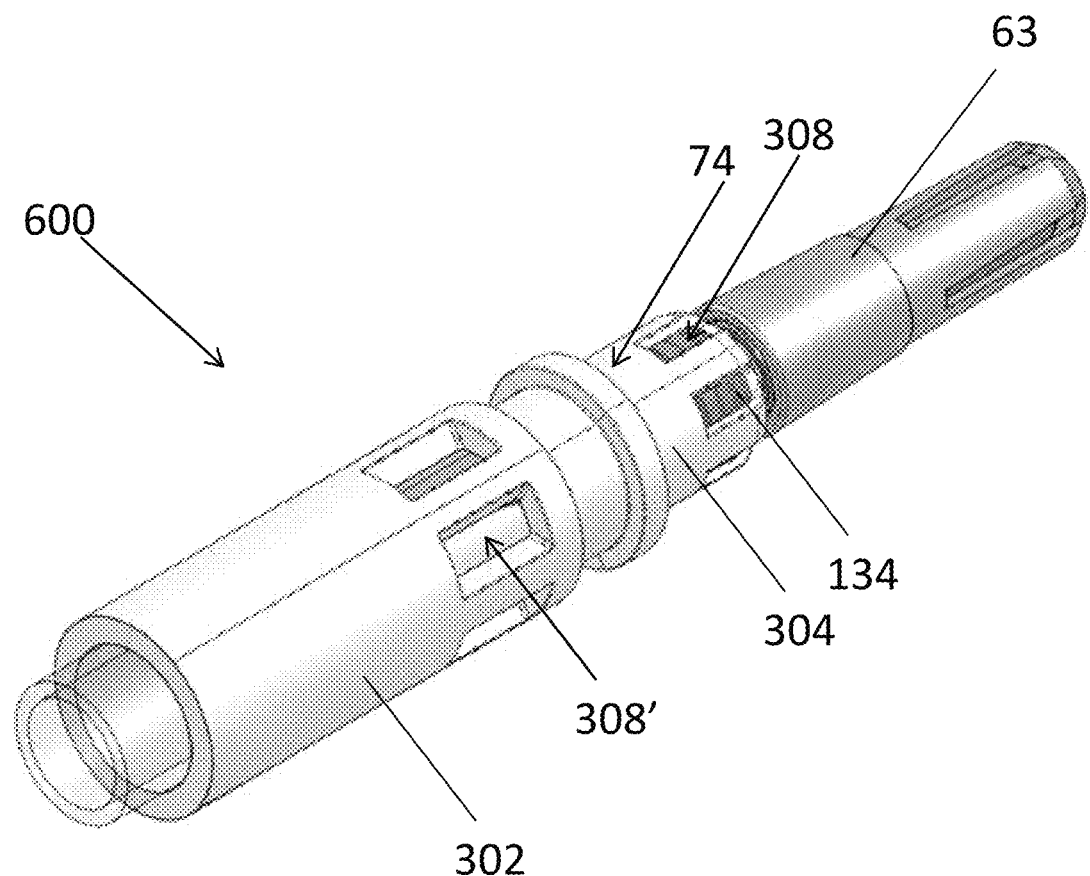
Figure 52A:
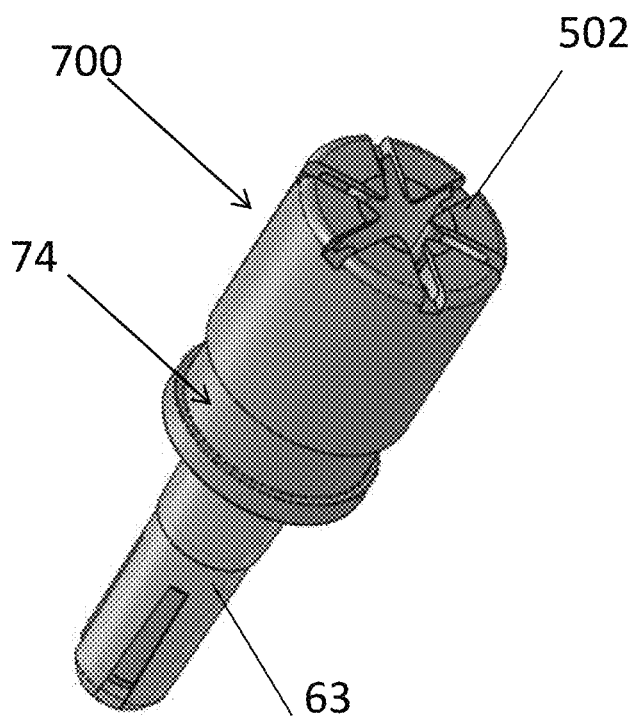
Figure 52B:
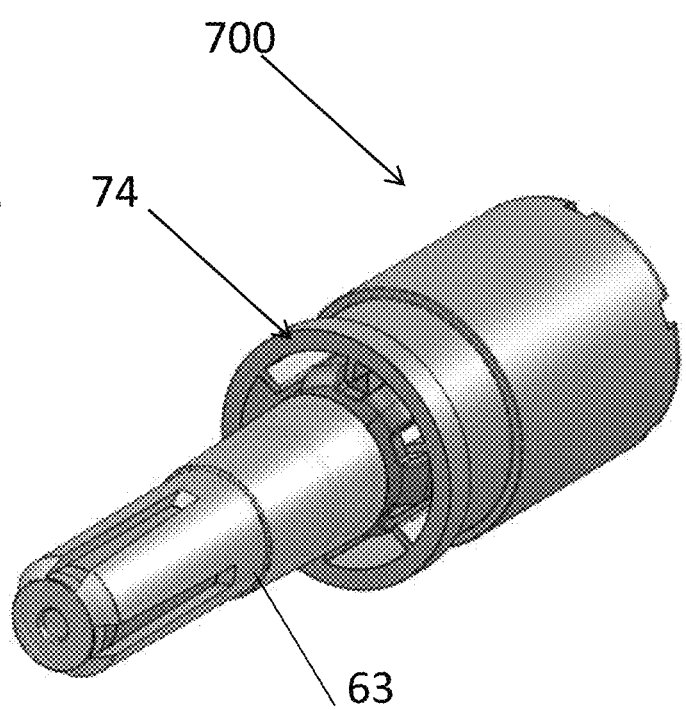

In order to mitigate this risk, the secondary/backup seal (110) is disposed in a proximal position during a first part of the assembly process, as shown in FIG. 12A. The needle proximal end (50) includes a needle shoulder (52). When the secondary/backup seal (110) is in the proximal position, the needle shoulder (52) abuts the proximal surface of the substrate/disc (112) of the secondary/backup seal (110) during assembly, preventing distal movement of the needle spine assembly (76) relative to the secondary/backup seal (110). The secondary/backup seal (110) includes a seal shoulder (124). When the secondary/backup seal (110) is in the proximal position, the seal shoulder (124) abuts a skirt shoulder (142) of the skirt (136) during assembly, preventing distal movement of the secondary/backup seal (110) relative to the skirt (136). The interference fits between (A) the needle shoulder (52) and the substrate/disc (112) and (B) the seal shoulder (124) and the skirt shoulder (142) prevent distal movement of the needle spine assembly (76) relative to the skirt (136) resulting from the force required for the needle proximal end (50) to penetrate the cartridge cap (72) during assembly. This, in turn, prevents premature needle latch (616) disengagement during assembly. An alternative embodiment for preventing premature unlatching of the needle spine assembly (76) includes grasping the needle spine assembly (76) with a fixture placed through openings in the skirt (136) (see, e.g., 308 in FIGS. 27 and 308' in FIGS. 49 and 50).

Figure 12B:
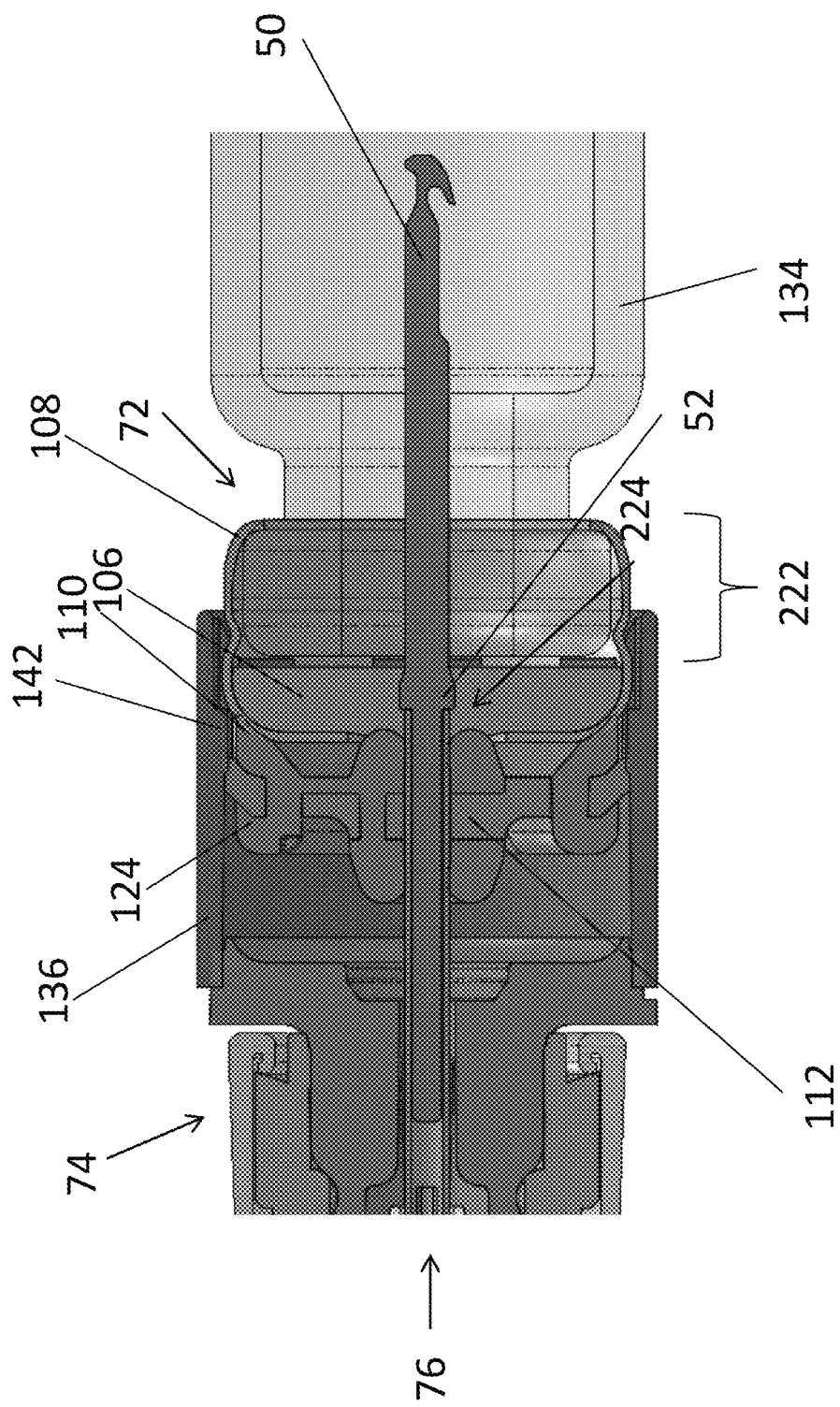

During a second part of the assembly process, as shown in FIG. 12B, the cartridge cap (72) enters the skirt (136) and pushes (with continued insertion of the cartridge (34) into the needle hub assembly (74)) the secondary/backup seal (110) into a distal position. As the cartridge cap (72) enters the skirt (136), the distal force exerted on the secondary/backup seal (110) plastically deforms (i.e., collapses) the skirt (136), thereby allowing the secondary/backup seal (110) to be pushed from the proximal position (FIG. 12A) past the shirt shoulder (142) to the distal position (FIG. 12B). The material from which the skirt (136) collapses as forces greater than about 2.0 lbs. Because of minimal force transfer from the secondary/backup seal (110) to the needle spine assembly (76) in a distal direction, when the secondary/backup seal (110) moves to the distal position, the needle spine assembly (76) remains in substantially the same position as when the secondary/backup seal (110) is in the proximal position. Consequently, with the secondary/backup seal (110) in the distal position, the needle spine assembly (76) is movable in the distal direction when the secondary/backup seal (110) is in the distal position, thereby allowing needle latch (616) disengagement after assembly.

Figure 12C:
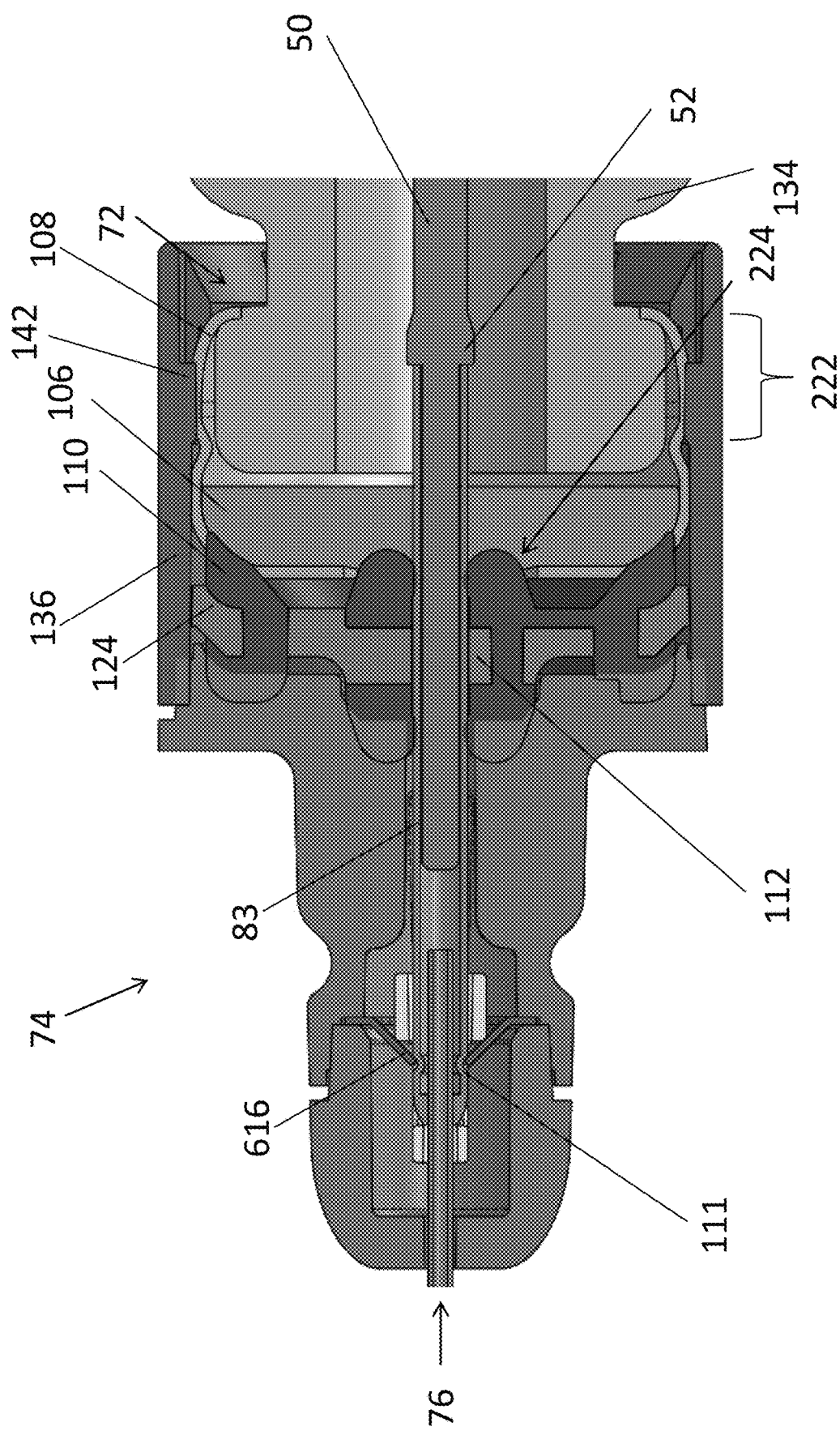

FIG. 12C depicts a more distal portion of the needle hub assembly (74) with the secondary/backup seal (110) in the distal position, as shown in FIG. 12B. FIG. 12C shows that the two arms of the needle latch (616) are seated in an latched position in the groove (111) on the needle joining member (83). The angle of the arms of the needle latch (616) in the latched position prevents proximal movement of the needle spine assembly (76) while the needle latch (616) is engaged with the groove (111) in the needle joining member (83). With complete insertion of the stopper member (36), the needle latch (616) becomes unseated from its previous latched position in the groove (111) on the needle joining member (83) to allow for proximal retraction of the needle spine assembly (76). The secondary/backup seal (110) also minimizes leakage should the medicine from inside of the cartridge (134) leak pass the cartridge cap (72). Further the secondary/backup seal (110) functions as a sterility barrier to minimize biological and particulate contamination of the needle distal end (48) (e.g., from the proximal surface 122 of the secondary/backup seal (110) or a distal surface of the cartridge cap (72)).

FIGS. 13A and 13B depict a secondary/backup seal (110) in a cartridge safe injection system according to another embodiment. In the depicted system, a skirt (136) snaps over a cartridge seal (72; i.e., a sealing member (106) and a crimp (108)) and compresses the secondary/backup seal (110) between the flange portion (222) of the cartridge (134) and a proximal base portion (78) of a needle hub assembly (74). The crimp (106) may be made of aluminum. The dimensions of the needle hub assembly (74) are such that snapping the skirt (136) over the crimp (108) compresses the secondary/backup seal (110) against the proximal base portion (78) of the needle hub assembly (74). Further, the skirt (136) includes a plurality of openings (140) configured to receive the flange portion (222) of the cartridge (134), thereby allowing the skirt (136) to return (i.e., via elasticity of the skirt material) to a close configuration.

Figure 14:
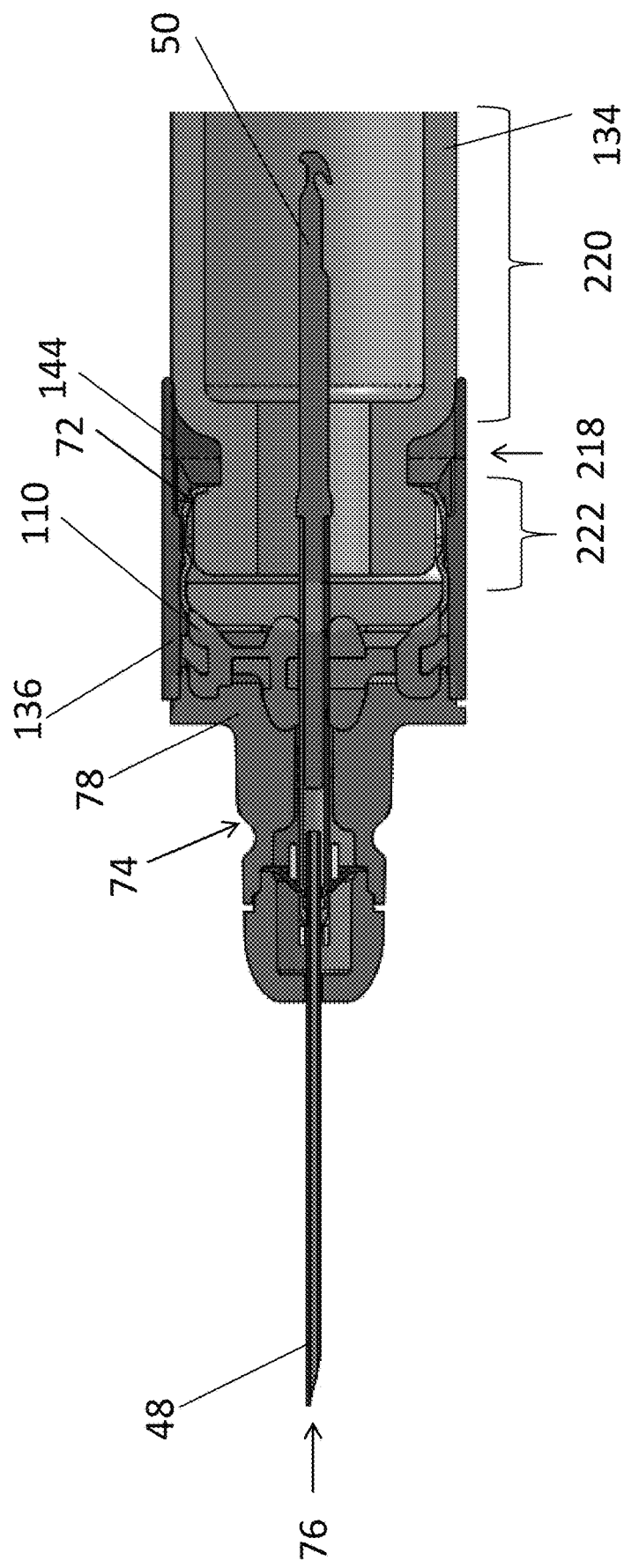

FIG. 14 depicts a cartridge safe injection system according to still another embodiment. As in the system depicted in FIGS. 13A and 13B, a skirt (136) snaps over a cartridge cap (72) and compresses the secondary/backup seal (110) between the flange portion (222) of the cartridge (134) and a proximal base portion (78) of a needle hub assembly (74). In addition, the skirt (136) includes a proximal extension (144) that extends proximally of the reduced diameter neck portion (218) and onto the body portion (220) of the cartridge (134). The interference between the proximal extension (144) of the skirt (136) and the body portion (220) of the cartridge (134) minimizes rotation (e.g., bending moment) of the needle hub assembly (74) about the flange portion (222) of the cartridge (134). Without the proximal extension (144), the needle hub assembly (74) may rotate about the flange portion (222) in a ball and socket fashion due to the sponginess of the elastically deformable sealing member (106), reducing stability, especially at the proximal end of the proximal needle portion (50) and the distal end of the needle distal end (48). Because these portions of the needle spine assembly (76) interact with the needle retention feature (712) and the patient, respectively, adding the proximal extension (144) to the skirt (136) increases stability of the needle hub assembly (74) on the flange portion (222) of the cartridge (134), and efficacy of the cartridge safe injection system.

Figure 15:
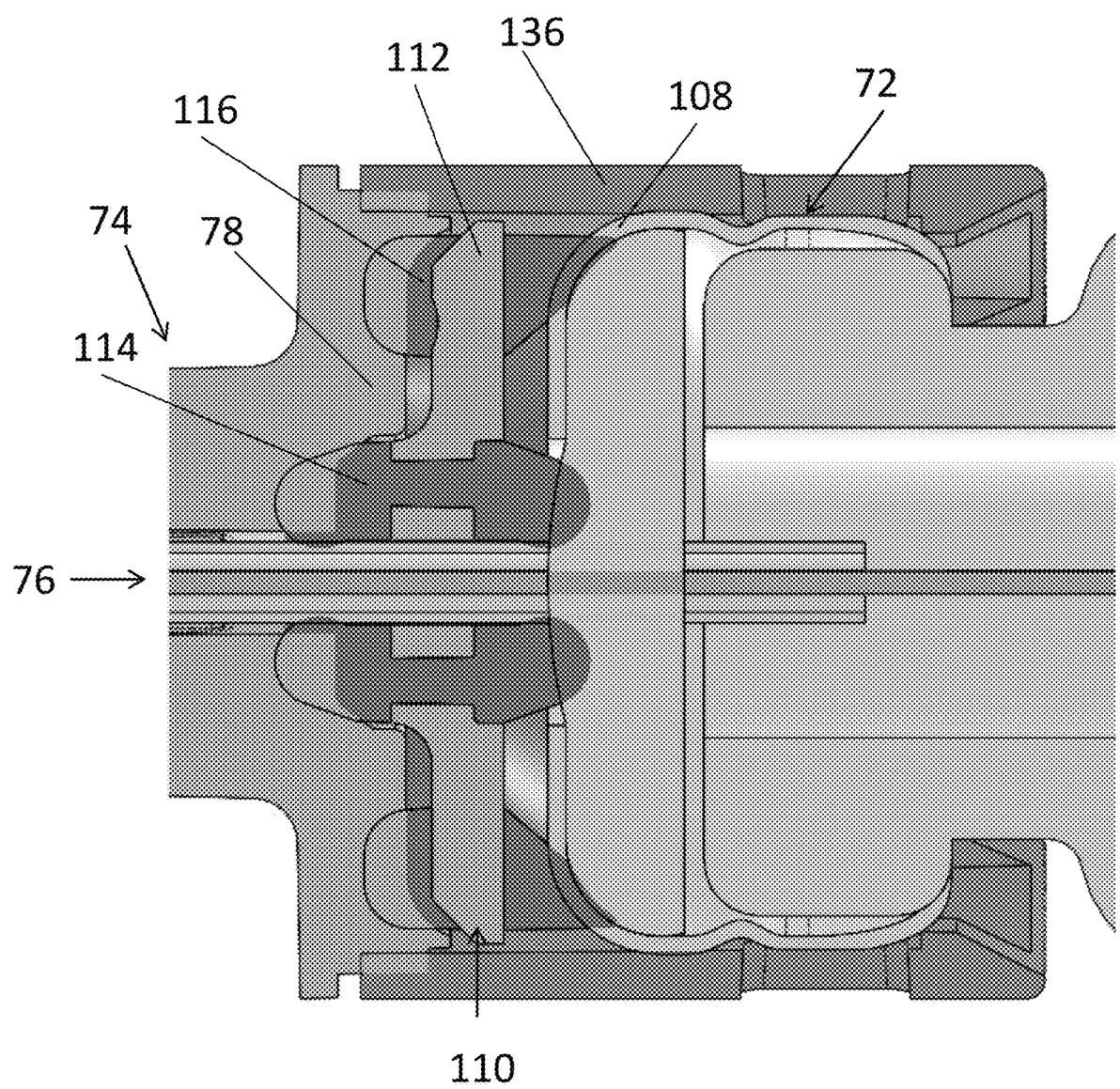

FIG. 15 depicts a secondary/backup seal (110) in a cartridge safe injection system according to yet another embodiment. FIG. 15 illustrates various fluid seals and sterility barriers forms by the secondary/backup seal (110), as mentioned above. The inner gasket (114) of the secondary/backup seal (110) seals around/against the needle spine assembly (76), the cartridge cap (72), and the proximal base portion (78) of the needle hub assembly (74). As such, the injectable substance (e.g., medicine) only contacts the needle spine assembly (76), which is stainless steel, the substrate/disc (112), which is polycarbonate, and the inner gasket (114), which is Versaflex. This prevents contact between the medicine and the crimp (108), which is aluminum and could be reactive with some medicines. The outer gasket (116) of the secondary/backup seal (110) seals against is the crimp (108) and the proximal base portion (78) of the needle hub assembly (74). These outer gasket (116) seals are mostly against external contaminants. The outer gasket (116) performs similar sealing functions as an interference fit between a Luer needle hub assembly and a crimp rolled groove (not shown). The sealing function of the outer gasket (116) also eliminates the need for an undercut in the skirt (136). Interference of the outer gasket (116) against the crimp (108) also increases stability of the needle hub assembly (74) on the flange portion (222) of the cartridge (134) (e.g., against the bending moment of the needle hub assembly (74) on the flange portion (222)).

The inner and outer gaskets (114, 116) elastically compress when forming the various seals described above. The shape and material (e.g., polycarbonate) of the inner and outer gaskets (114, 116) facilitates their elastic compression up to 40-60% against the various portions of the injection system (e.g., the needle spine assembly (76), the cartridge cap (72), the proximal base portion (78) of the needle hub assembly (74), and the crimp (108)). This range of compression facilitates seal formation with cartridges (134) having variable cartridge cap (72) (e.g., crimp (108)) thickness.

Figure 16:
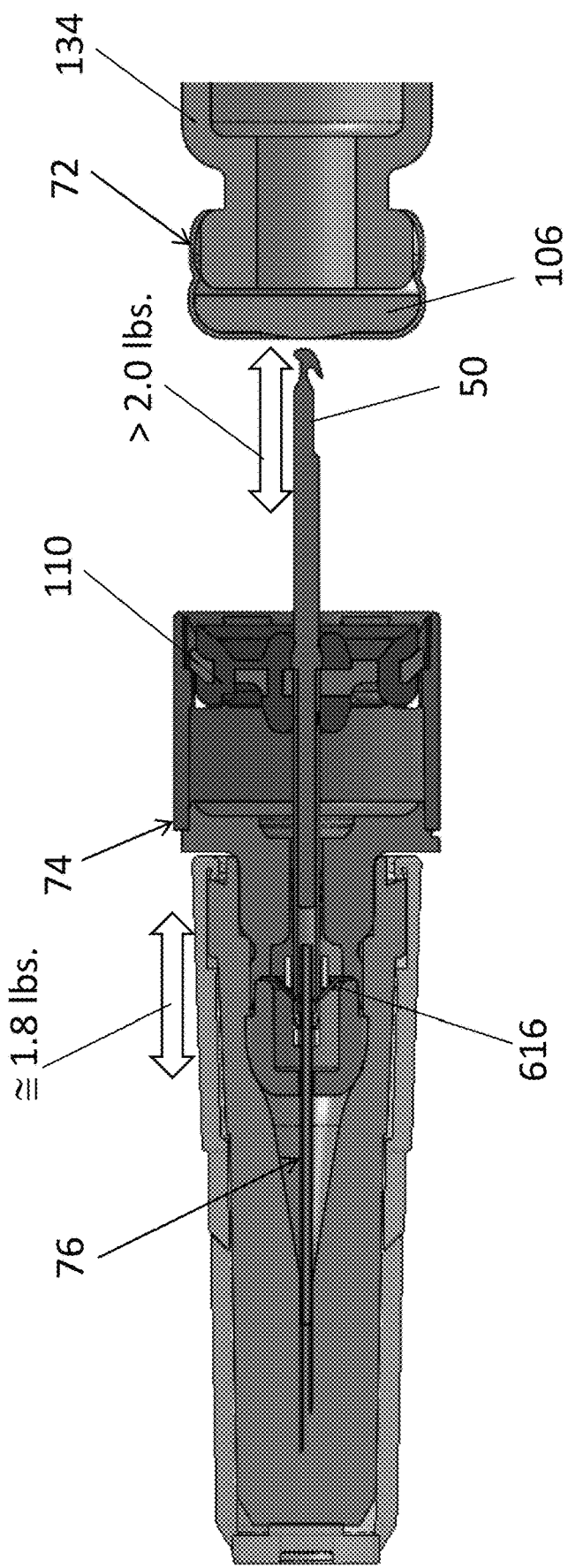

FIG. 16 illustrates several related/opposing forces during partial assembly of a cartridge safe injection system according to another embodiment. This embodiment is similar to one previously shown in FIGS. 12A to 12C. The force required for the needle proximal end (50) to pierce the sealing member (106) in the cartridge cap (72) may be greater than around 2.0 lbs. The force required to release a needle latch (616), as described above, may be about 1.8 lbs. Accordingly, during assembly of the needle hub assembly (74) onto the cartridge (134), the opposing force from piercing the sealing member (106) may cause the needle spine assembly (76) to move distally, thereby releasing the needle latch (616). An unlatched needle spine assembly (76) is free to move proximally relative to the needle hub assembly (74). This can result in an insertion error during injection that could inflict unnecessary pain on a patient. Further, the needle spine assembly (76) includes several openings through which injectable substance (e.g., medicine) flow. Unexpected proximal movement of the needle spine assembly (76) can cause misalignment of these openings and lead to flow problems (e.g., blockages). As described above, the secondary/backup seal (110), in its proximal position, opposes distal movement of the needle spine assembly (76).

FIGS. 17A-17D depict the secondary/backup seal (110) in proximal (FIGS. 17A and 17B) and distal (FIGS. 17C and 17D) positions in a cartridge safe injection system according to still another embodiment. This embodiment is similar to one previously shown in FIGS. 12A to 12C. In the proximal position, the secondary/backup seal (110) prevents distal movement of the needle spine assembly (76) relative to the skirt (136) resulting from the force required for the needle proximal end (50) to penetrate the cartridge cap (72) during assembly. This, in turn, prevents premature needle latch (616) disengagement during assembly. In the distal position, the secondary/backup seal (110) allows distal movement of the needle spine assembly (76) relative to the skirt (136), thereby allowing the needle latch (616) to disengage after assembly of the needle hub assembly (74) and the cartridge (134).

In order to mitigate the risk of premature needle latch (616) disengagement during assembly, the secondary/backup seal (110) is disposed in the proximal position (FIGS. 17A and 17B) during a first part of the assembly process. During the first part of the assembly process, the needle proximal end (50) is pierced through the sealing member (106) in the cartridge cap (72), as shown in FIG. 17B. As described above, the force required to pierce the sealing member may be greater than around 2.0 lbs. In order to resist this force, the needle proximal end (50) includes a needle shoulder (52). When the secondary/backup seal (110) is in the proximal position, the needle shoulder (52) abuts the proximal surface of the substrate/disc (112) of the secondary/backup seal (110) during assembly, preventing distal movement of the needle spine assembly (76) relative to the secondary/backup seal (110). The secondary/backup seal (110) also includes a seal shoulder (124). When the secondary/backup seal (110) is in the proximal position, the seal shoulder (124) abuts a skirt shoulder (142) of the skirt (136) during assembly, preventing distal movement of the secondary/backup seal (110) relative to the skirt (136). The interference fits between (A) the needle shoulder (52) and the substrate/disc (112) and (B) the seal shoulder (124) and the skirt shoulder (142) prevent distal movement of the needle spine assembly (76) relative to the skirt (136) resulting from the force required for the needle proximal end (50) to penetrate the cartridge cap (72) during assembly. This, in turn, prevents premature needle latch (616) disengagement during assembly.

During a second part of the assembly process, as shown in FIGS. 17C and 17D, the cartridge cap (72) enters the skirt (136) and pushes (with continued insertion of the cartridge (134) into the needle hub assembly (74)) the secondary/backup seal (110) into a distal position. As the cartridge cap (72) enters the skirt (136), the distal force exerted on the secondary/backup seal (110) plastically deforms (i.e., collapses) the skirt (136), thereby allowing the secondary/backup seal (110) to be pushed from the proximal position (FIGS. 17A and 17B) past the shirt shoulder (142) to the distal position (FIGS. 17C and 17D). The material from which the skirt (136) collapses as forces greater than about 2.0 lbs. Because of minimal force transfer from the secondary/backup seal (110) to the needle spine assembly (76) in a distal direction, when the secondary/backup seal (110) moves to the distal position, the needle spine assembly (76) remains in substantially the same position as when the secondary/backup seal (110) is in the proximal position. Consequently, with the secondary/backup seal (110) in the distal position, the needle spine assembly (76) is movable in the distal direction when the secondary/backup seal (110) is in the distal position, thereby allowing needle latch (616) disengagement after assembly.

FIGS. 17A-17D also show that the secondary/backup seal (110) centers the needle spine assembly (76) during both the first and second part of the assembly process. Centering the needle spine assembly (76) facilitates on-target capture of the needle proximal end (50) by a needle retention feature (712) by reducing alignment deviation. This is especially beneficial in select cartridge safe injection systems with a dual-chamber construction, such as those described in U.S. provisional patent application Ser. No. 62/431,382, which was previously incorporated by reference herein. As described in U.S. provisional patent application Ser. No. 62/431,382, some dual-chamber cartridge safe injection systems may have a longer needle proximal end (50), which magnifies any alignment deviation.

Figure 18A:
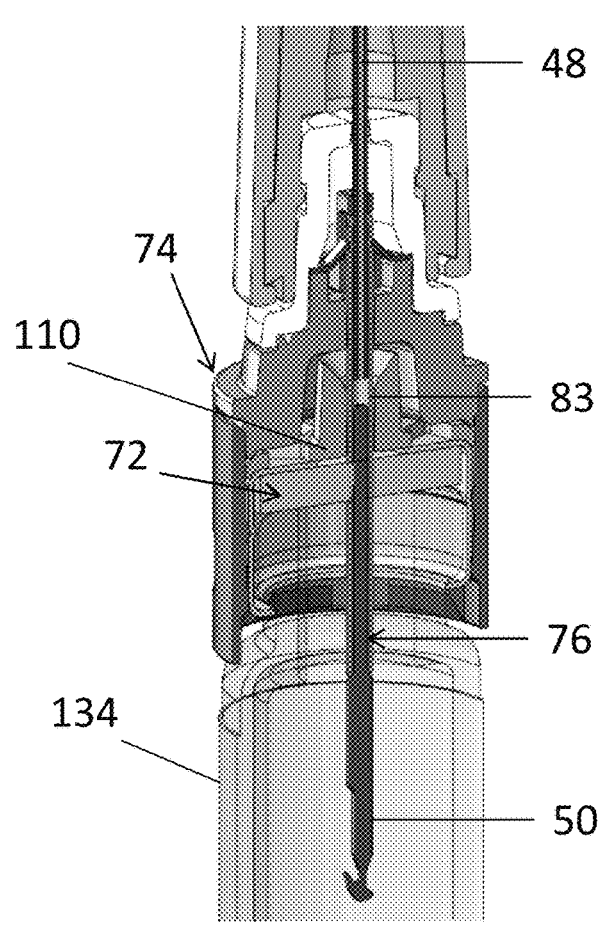
Figure 18B:
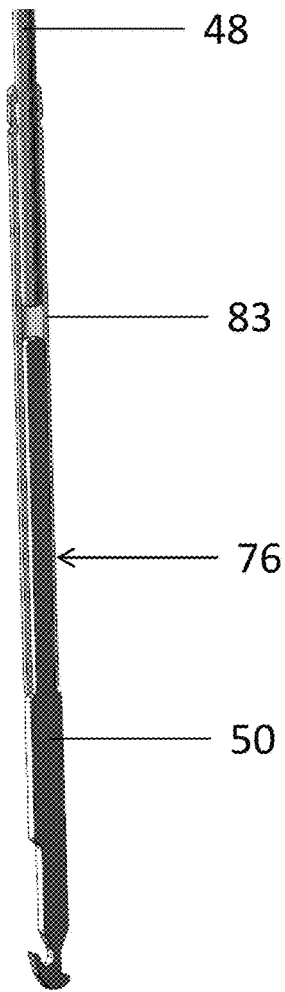
Figure 18C:
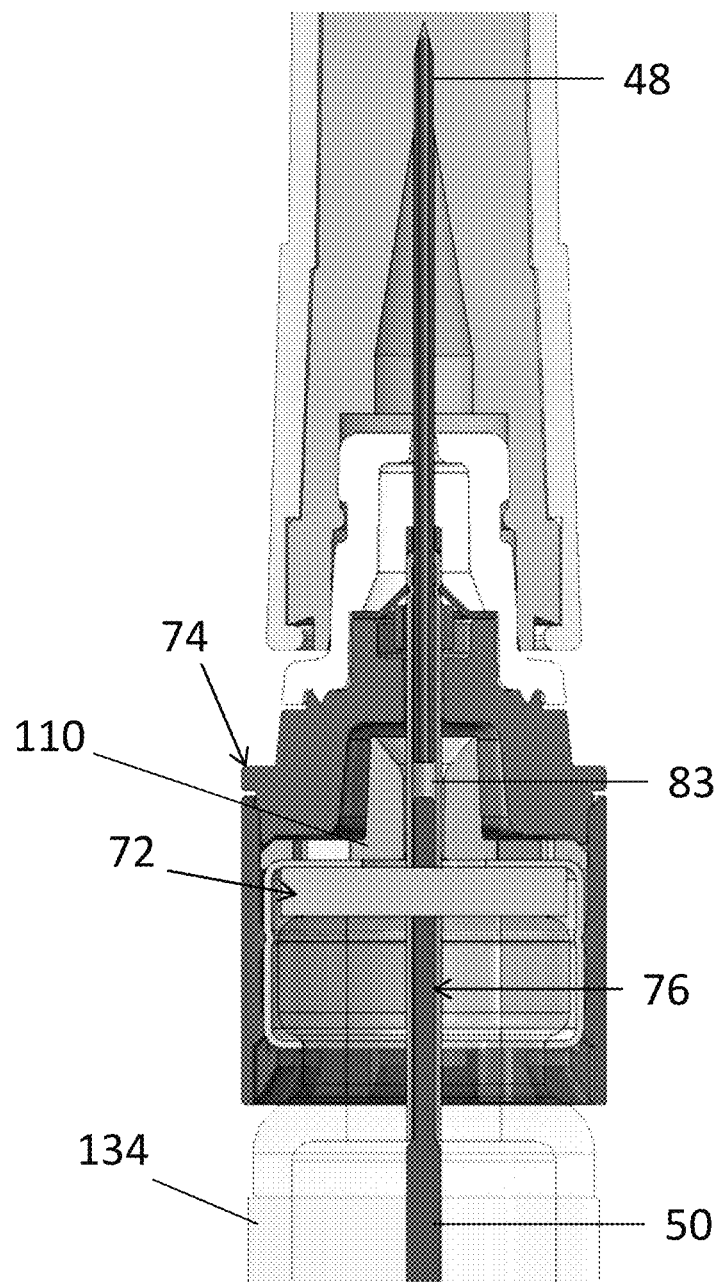

FIGS. 18A and 18C depict a cartridge safe injection system including a secondary/backup seal (110) according to yet another embodiment. The cartridge safe injection system includes a needle hub assembly (74) coupled to a cartridge (134), which includes a cartridge cap (72). The needle hub assembly (74) includes a needle spine assembly (76), which includes a needle proximal portion (50) coupled to a needle joining member (83), which is in turn coupled to a distal needle tip (48), as shown in FIG. 18B. The secondary/backup seal (110) depicted in FIGS. 18A and 18C forms a fluid and sterility seal against the cartridge cap (72) as a supplement thereto.

Figure 19:
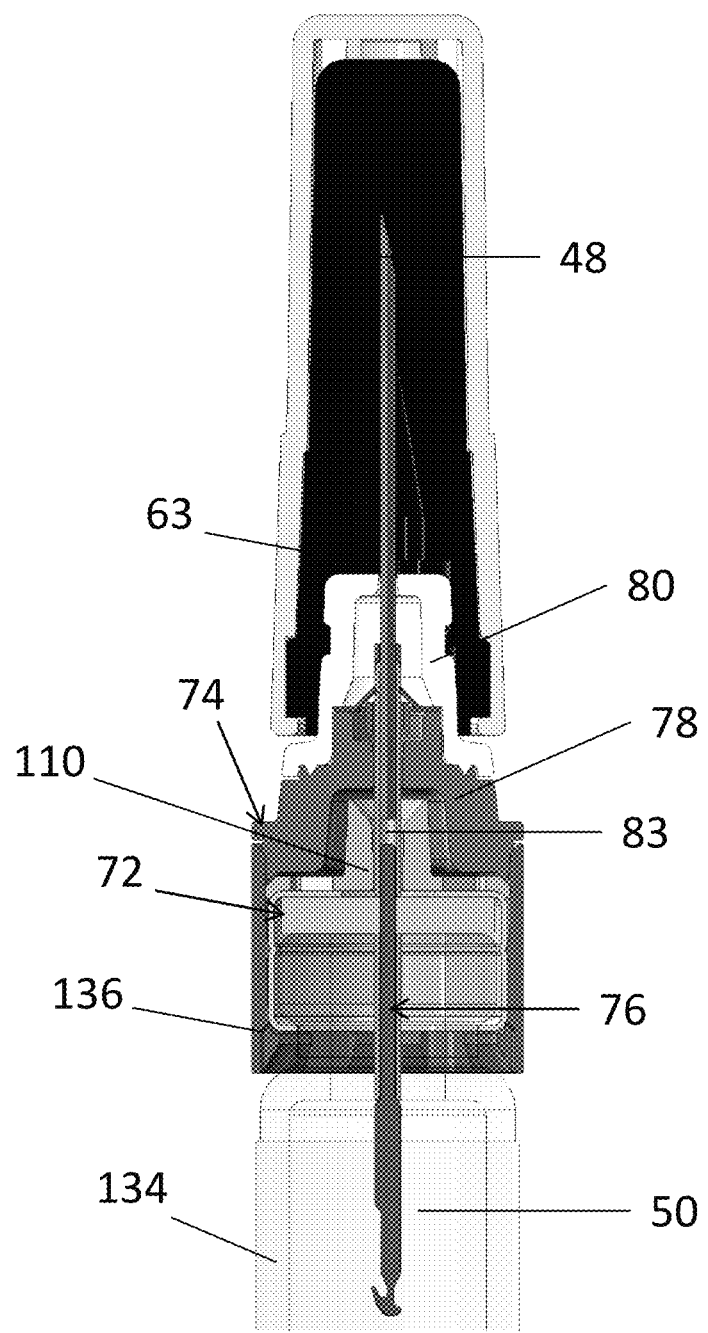

FIG. 19 depicts various sterility barriers in the cartridge safe injection system depicted in FIGS. 18A and 18C. Sterility barriers are formed between the following portions of the cartridge safe injection system: (A) the elastomeric the rigid needle shield/needle cover member (63) and the distal nose cone (80) of the needle hub assembly (74); (B) the distal nose cone (80) and the proximal base portion (78) of the needle hub assembly (74); (C) the proximal base portion (78) of the needle hub assembly (74) and the skirt (136); and (D) the skirt (136) and the cartridge cap (72). The secondary/backup seal (110) forms a supplemental sterility barrier against the cartridge cap (72).

Figure 20:
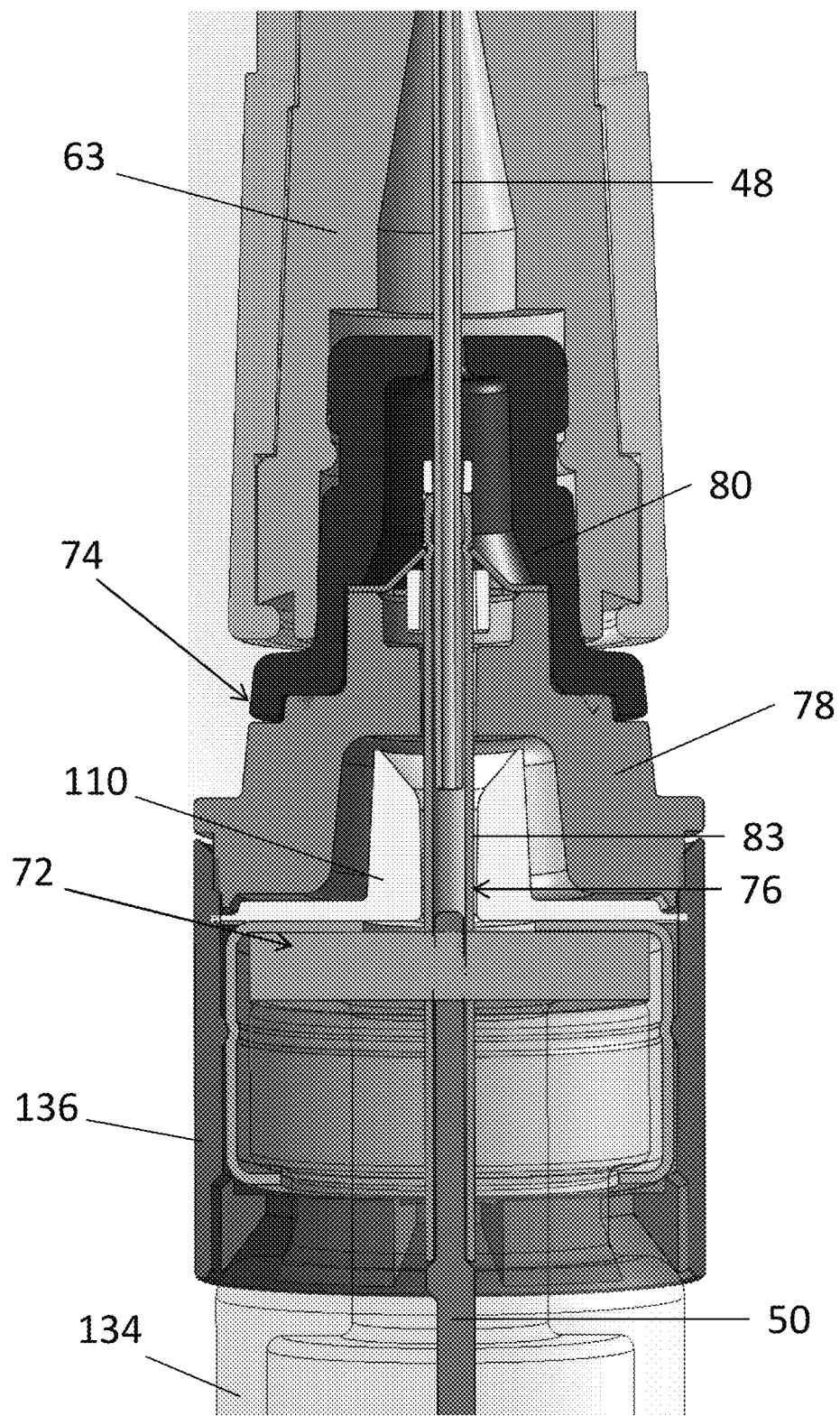
Figure 21:
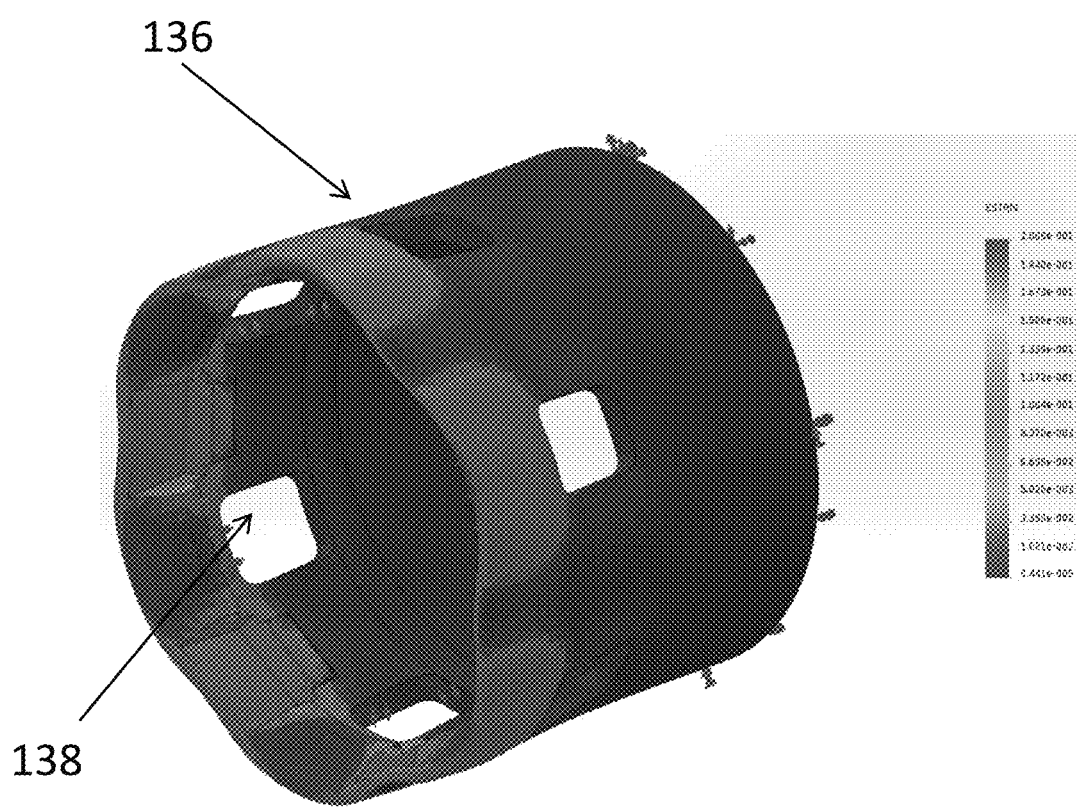
FIG. 21 depicts a skirt of a cartridge safe injection system according to one embodiment.

FIG. 20 depicts in greater detail the cartridge safe injection system depicted in FIGS. 18A, 18C, and 19. The skirt (136) may be made from polymers, such as Nylon 12 (GRILAMID), polycarbonate, and/or polypropylene. The material may be selected depending on the dimensions and tolerances of the cartridge cap (72) (e.g., outer diameter and/or length). In one embodiment depicted in FIG. 21, the skirt (136) snap fits over the underside of the cartridge (72) at about 6-10% elastic strain. The skirt (136) includes a plurality of spaces (138). FIG. 20 also depicts various welds coupling portions of the needle hub assembly (74). For instance, the skirt (136) may be coupled to the proximal base portion (78) of the needle hub assembly (74) by an ultrasonic welded lap joint. Similarly, the distal nose cone (80) and the proximal base portion (78) of the needle hub assembly (74) may be coupled to each other with an ultrasonic butt joint by a triangular energy director. In an alternative embodiment, the proximal base portion (78) and the skirt (136) may be integrally formed as one piece.

Figure 22A:
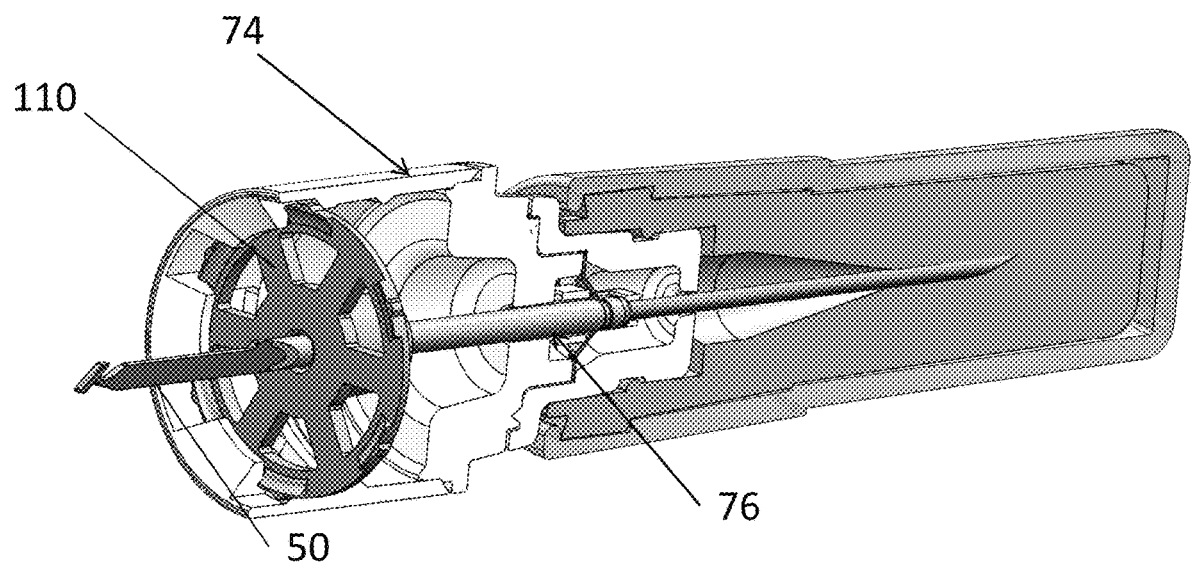
FIGS. 22A-22B depict a cartridge safe injection system having a secondary/backup seal according to one embodiment.
Figure 22B:
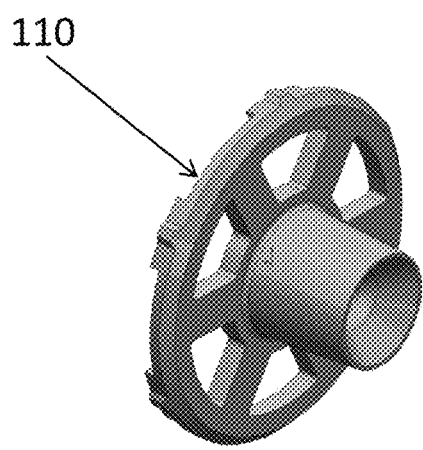

FIG. 22A depicts a secondary/backup seal (110) in a needle hub assembly (74) according to another embodiment. FIG. 22B depicts the secondary/backup seal (110) by itself. As shown in FIG. 22A, the secondary/backup seal (110) maintains the alignment of the needle spine assembly (76) to minimize the deviation of the needle proximal portion (50). As described above, minimizing this deviation reduces errors during assembly of the needle hub assembly (74) and a cartridge (134). FIG. 22A depicts the secondary/backup seal (110) in a proximal position similar to those depicted in FIGS. 12A, 17A, and 17B. During assembly of the needle hub assembly (74) and the cartridge (134), the cartridge (134) pushes the secondary/backup seal (110) into a distal position similar to those depicted in FIGS. 12C, 17C, and 17D.

Figure 23A:
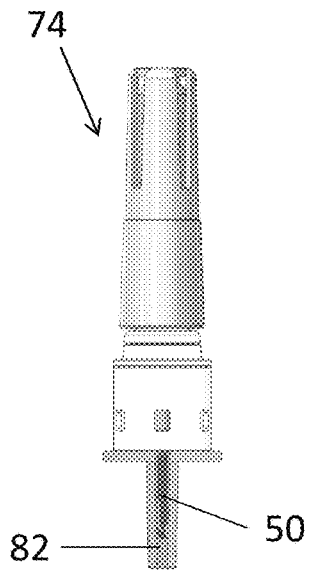
FIGS. 23A-23E depict assembly of a needle hub assembly and a cartridge according to one embodiment.
Figure 23B:
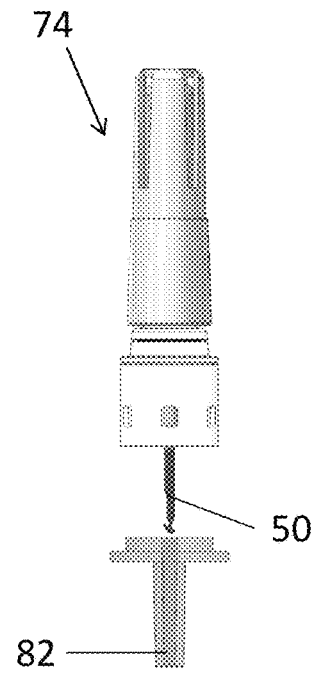
Figure 23C:
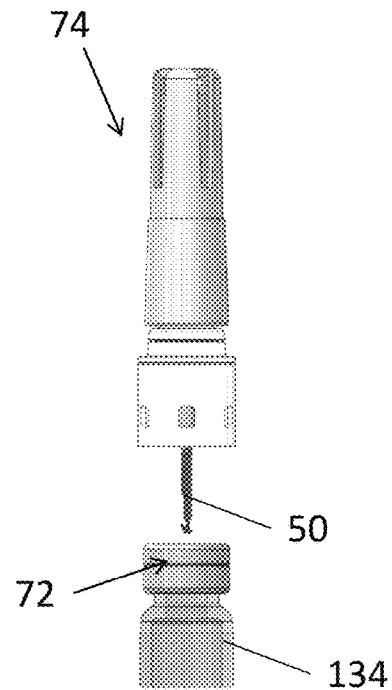
Figure 23D:
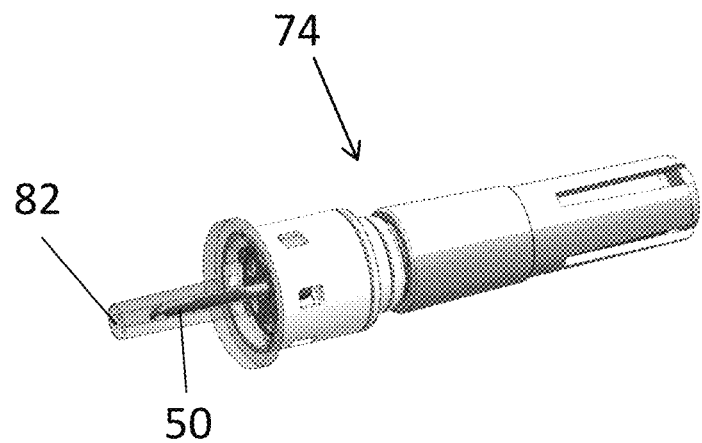
Figure 23E:
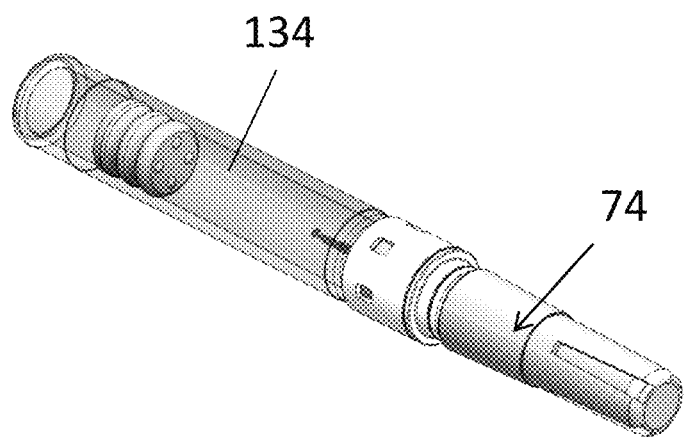

FIGS. 23A-23E depict assembly of a needle hub assembly (74) and a cartridge (134) according to still another embodiment. FIGS. 23A and 23D depict the needle hub assembly (74) as shipped, which includes a point protector (82) removably coupled thereto. The point protector (82) is configured to prevent damage to the needle proximal end (50). The needle hub assembly (74) as shipped may be gamma sterilized in a quadruple bag. FIG. 23B illustrates removal of the point protector (82) from the needle hub assembly (74) prior to assembly with the cartridge (134). FIG. 23C shows the needle hub assembly (74) disposed adjacent the cartridge (72) of the cartridge (134) prior to assembly. FIG. 23E depicts an assembled cartridge (134)/needle hub assembly (74).

Exemplary Cartridge and Needle Assembly and Injection Methods

Having described cartridge safe injection systems including secondary/backup seals (110) according to various embodiments, methods of assembling cartridge safe injection systems and performing injections using same will now be described.

Figure 24A:
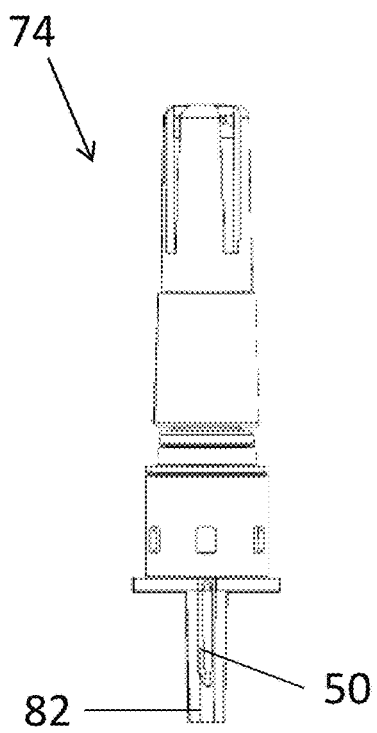
FIGS. 24A-24R depict a method of assembling a cartridge safe injection system and performing an injection using same according to one embodiment.
Figure 24B:
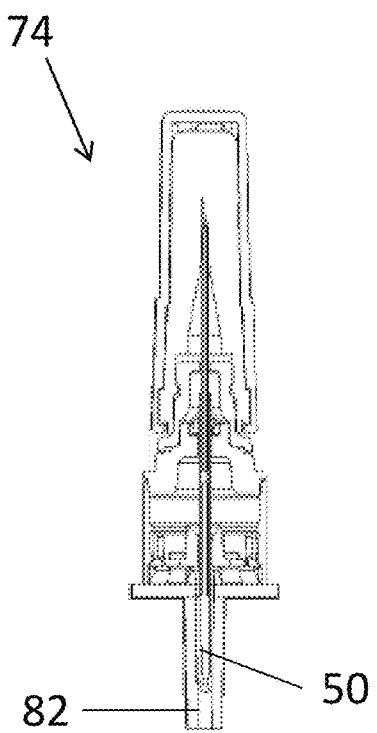
Figure 24C:
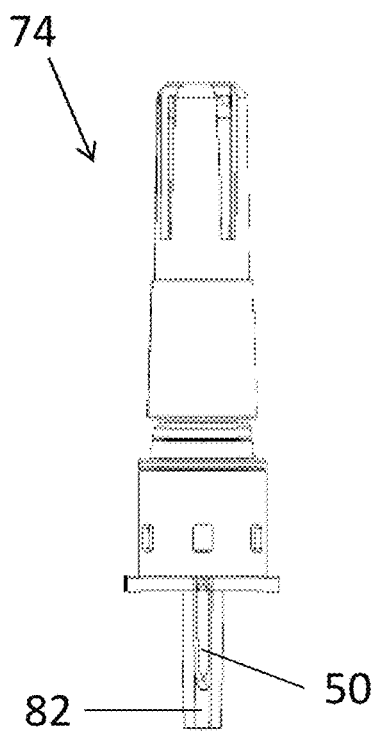
Figure 24D:
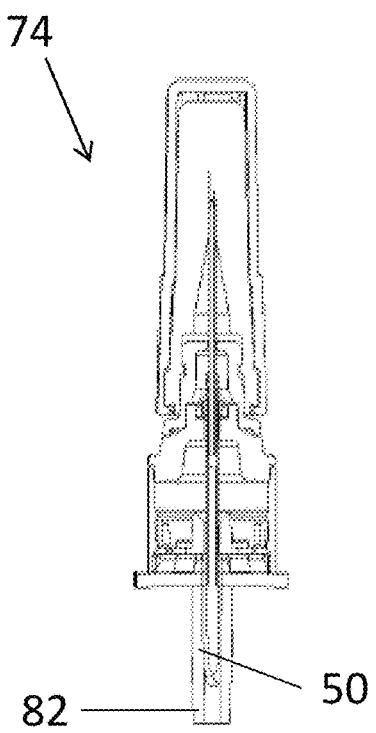
Figure 24E:
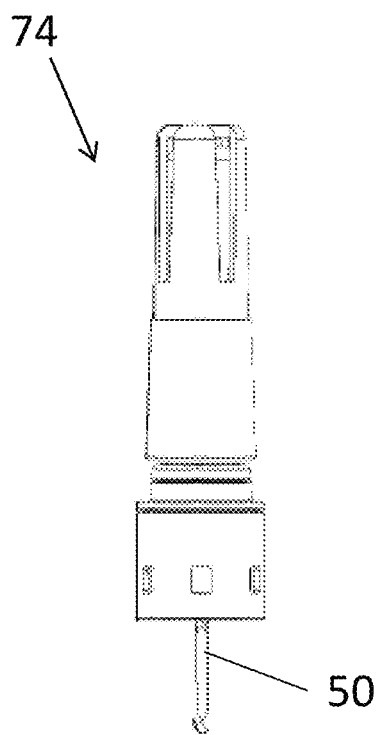
Figure 24F:
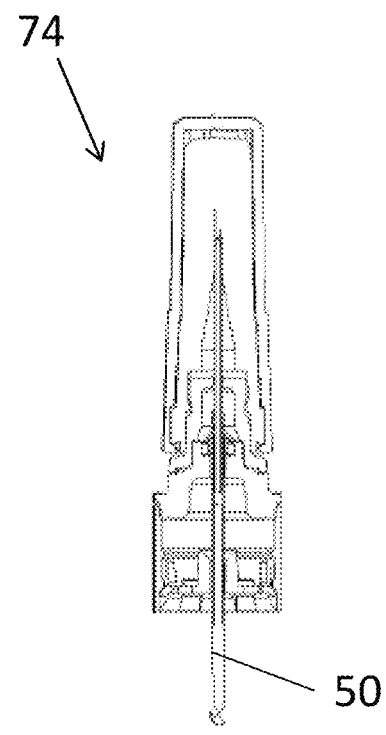
Figure 24G:
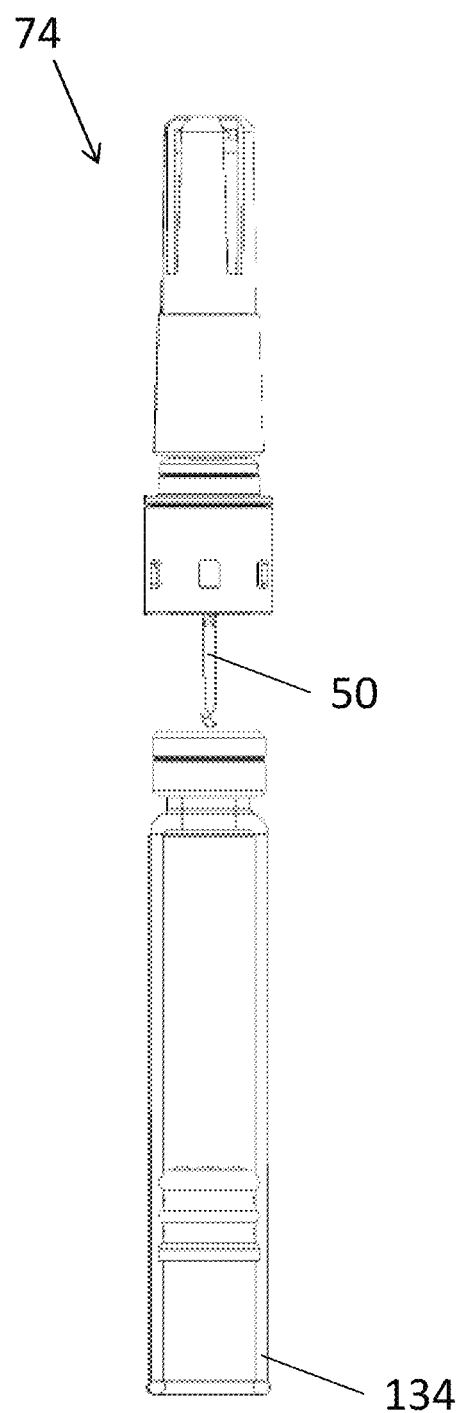
Figure 24H:
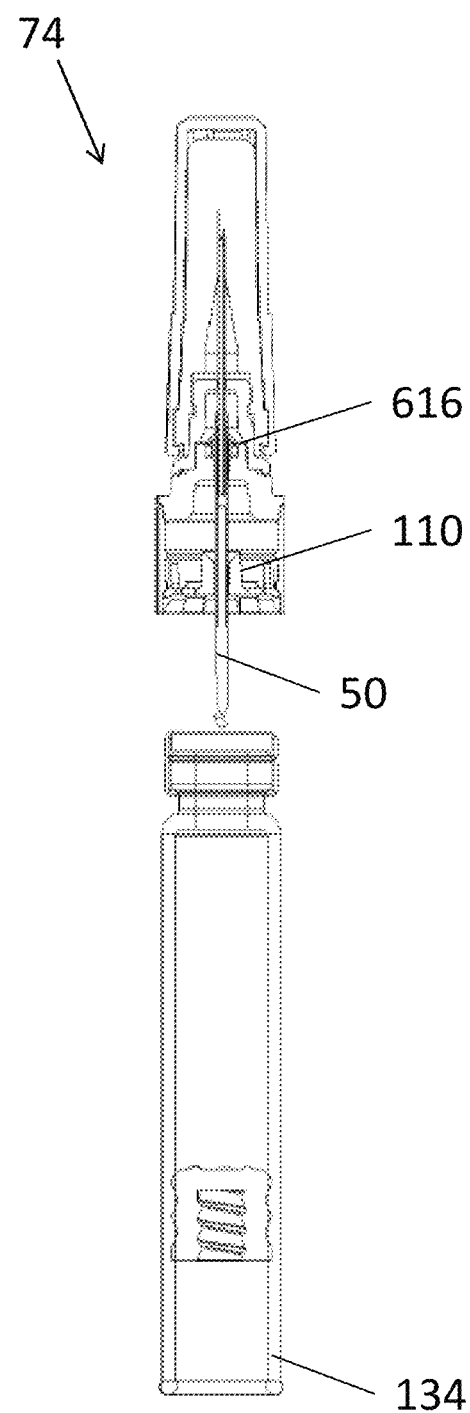
Figure 24I:
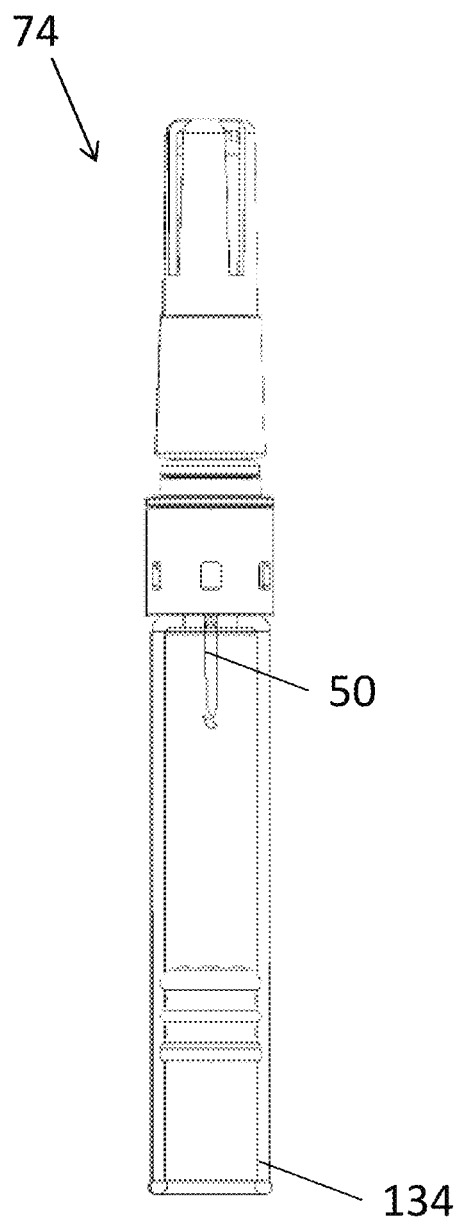
Figure 24J:
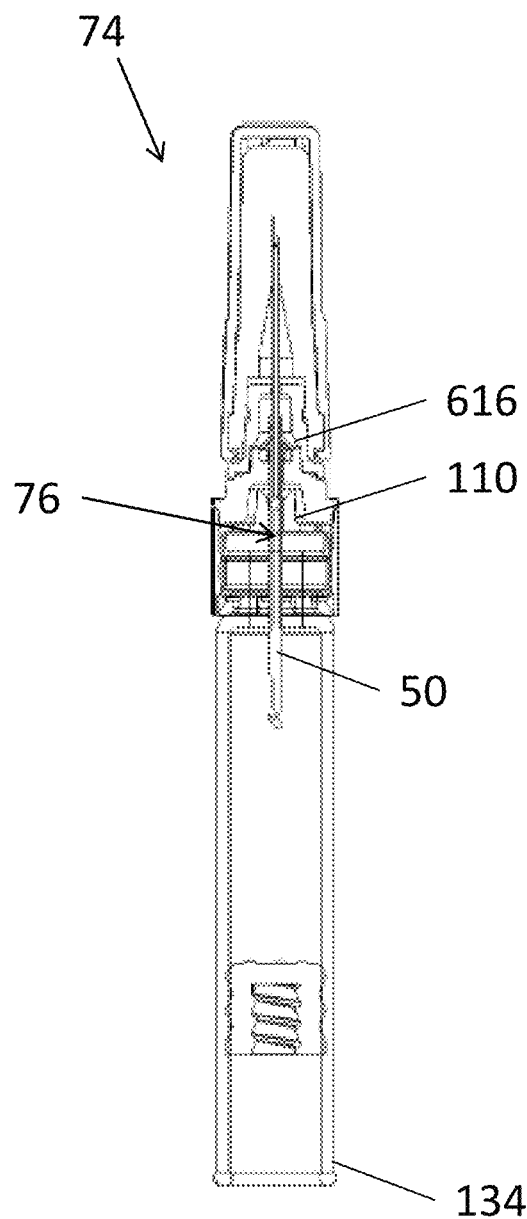
Figure 24K:
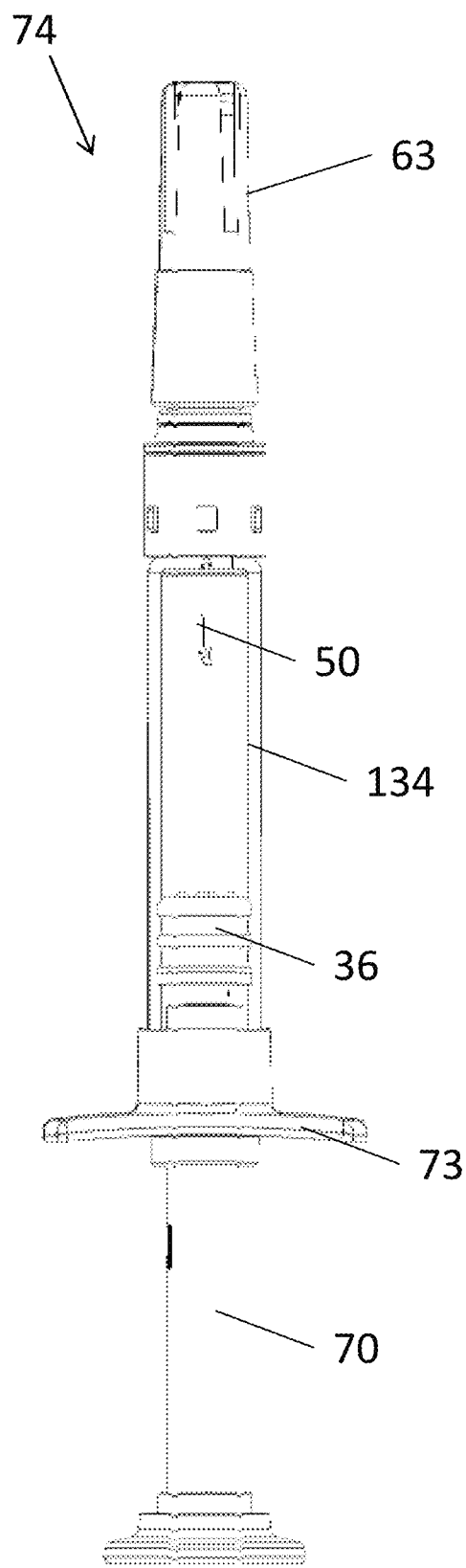
Figure 24L:
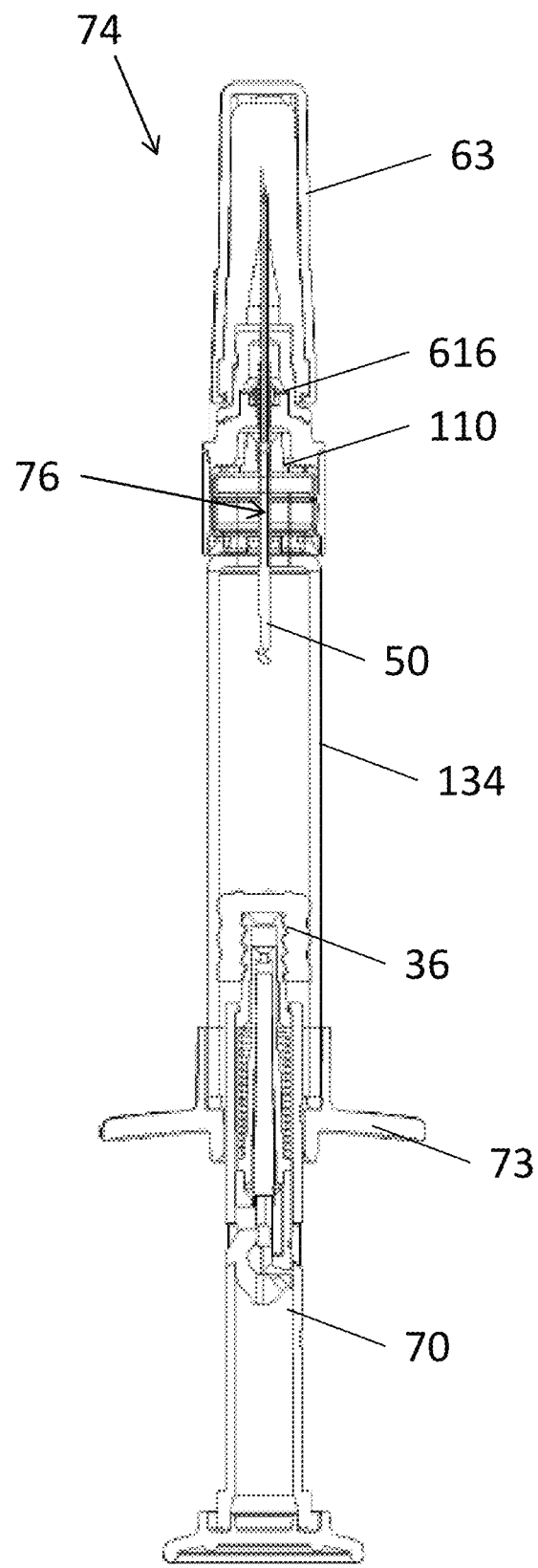
Figure 24M:
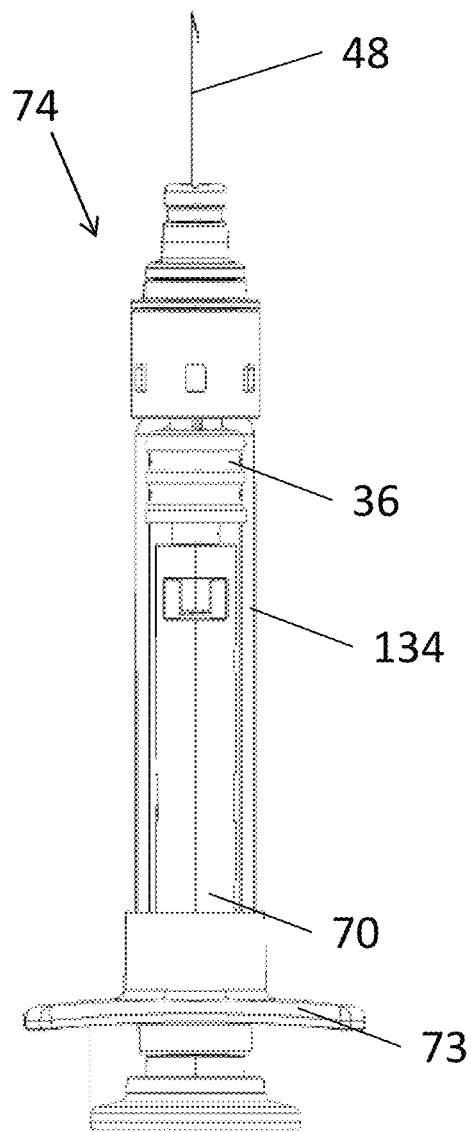
Figure 24N:
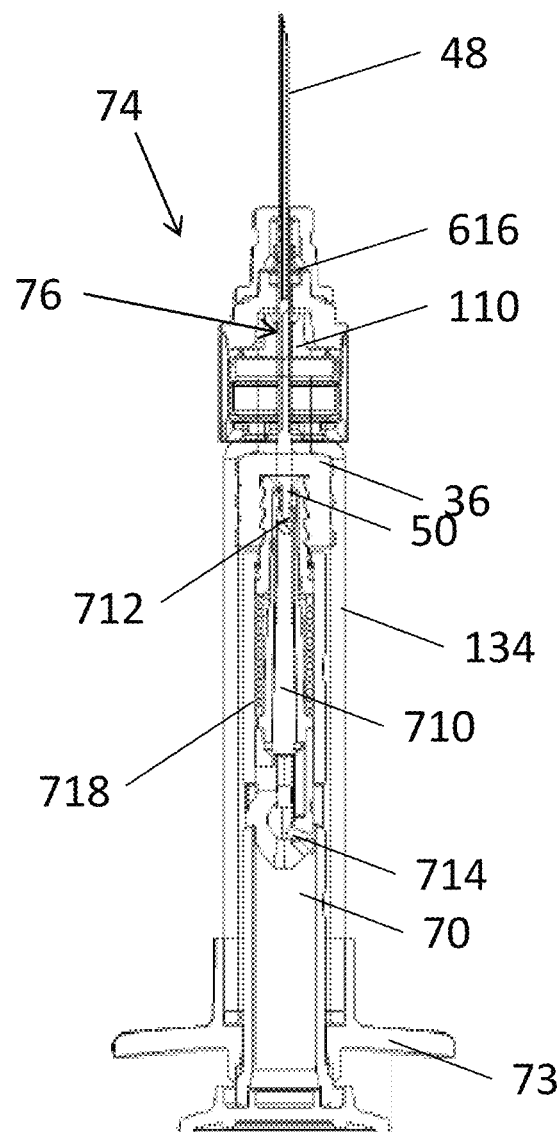
Figure 24O:
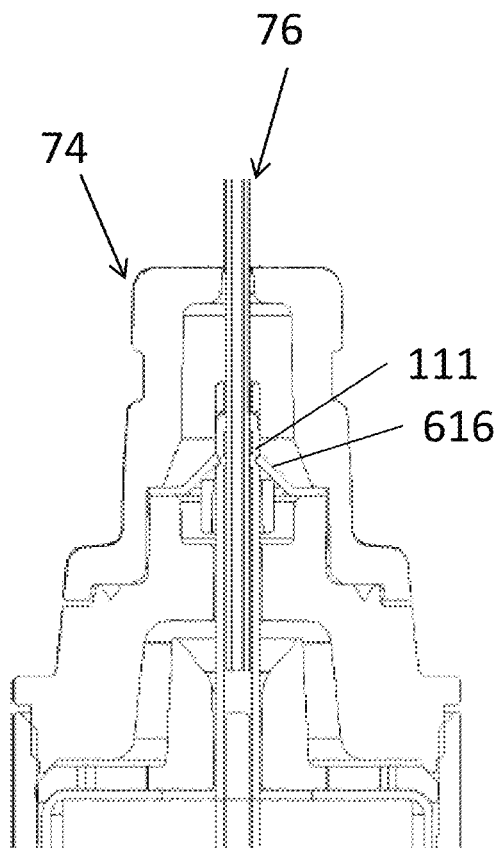
Figure 24P:
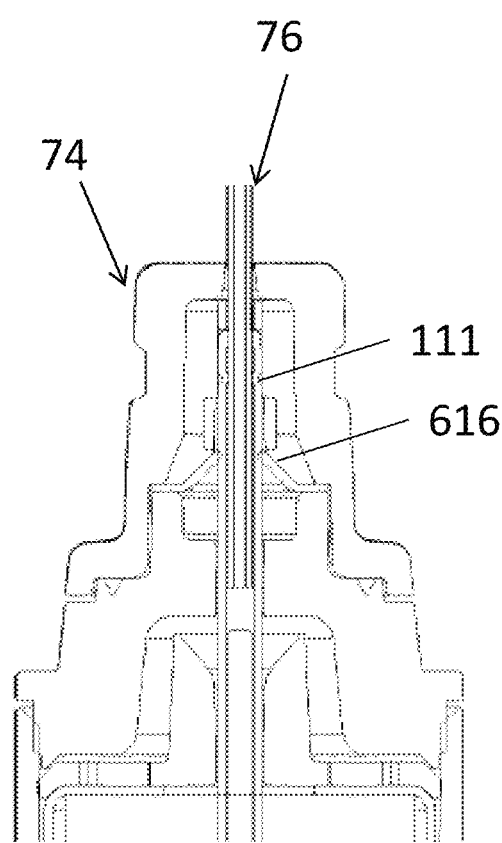
Figure 24Q:
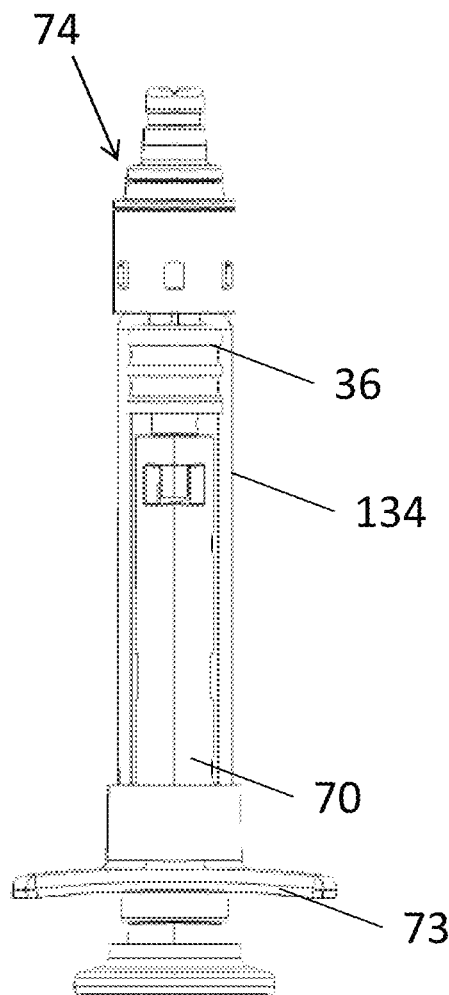
Figure 24R:
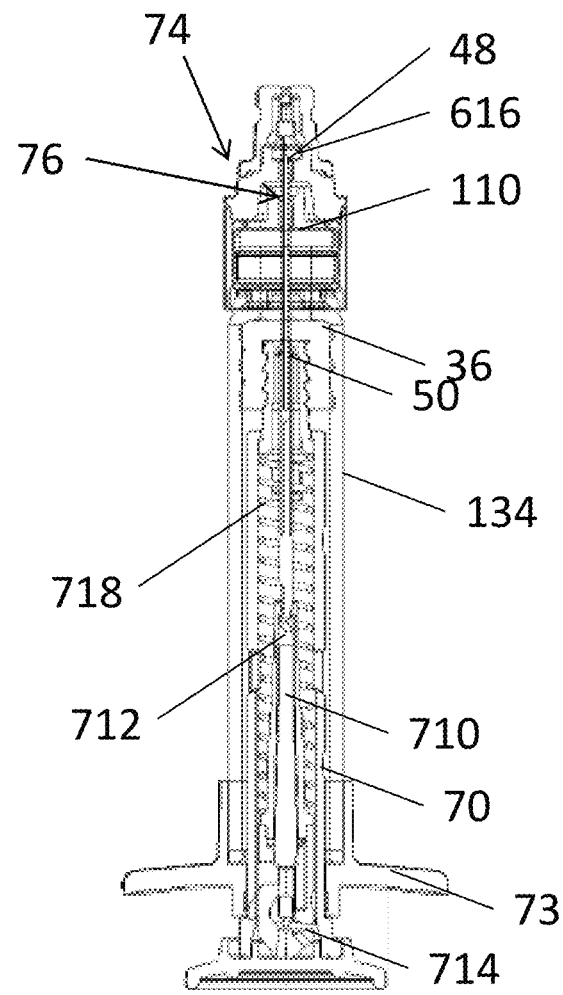
Figure 25C:
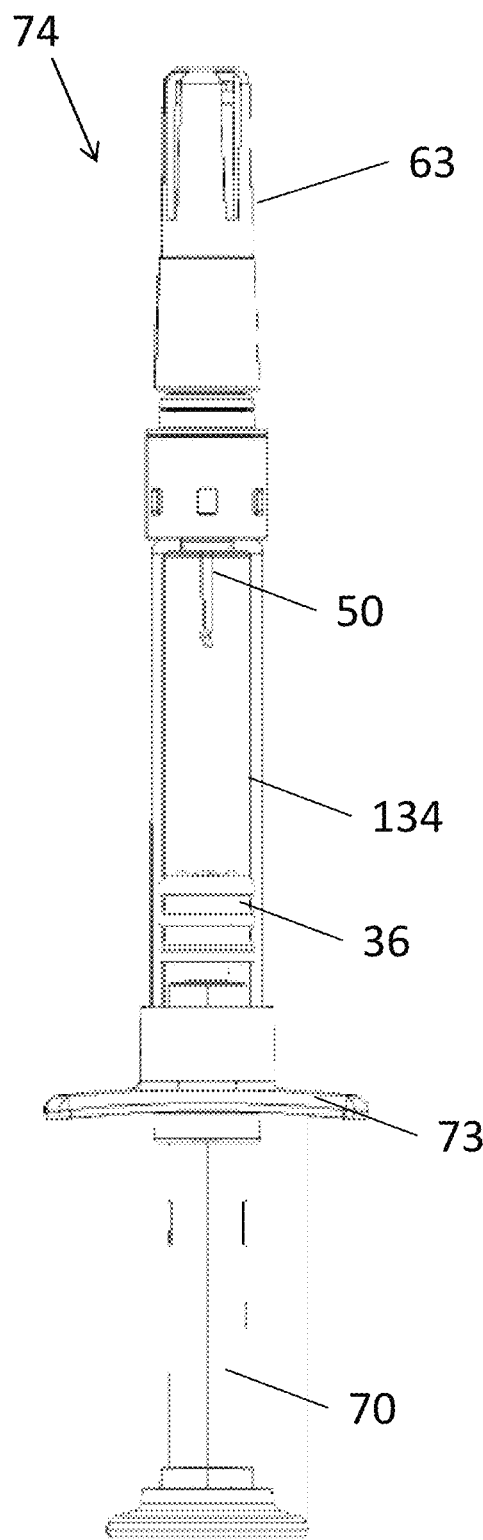
Figure 25D:
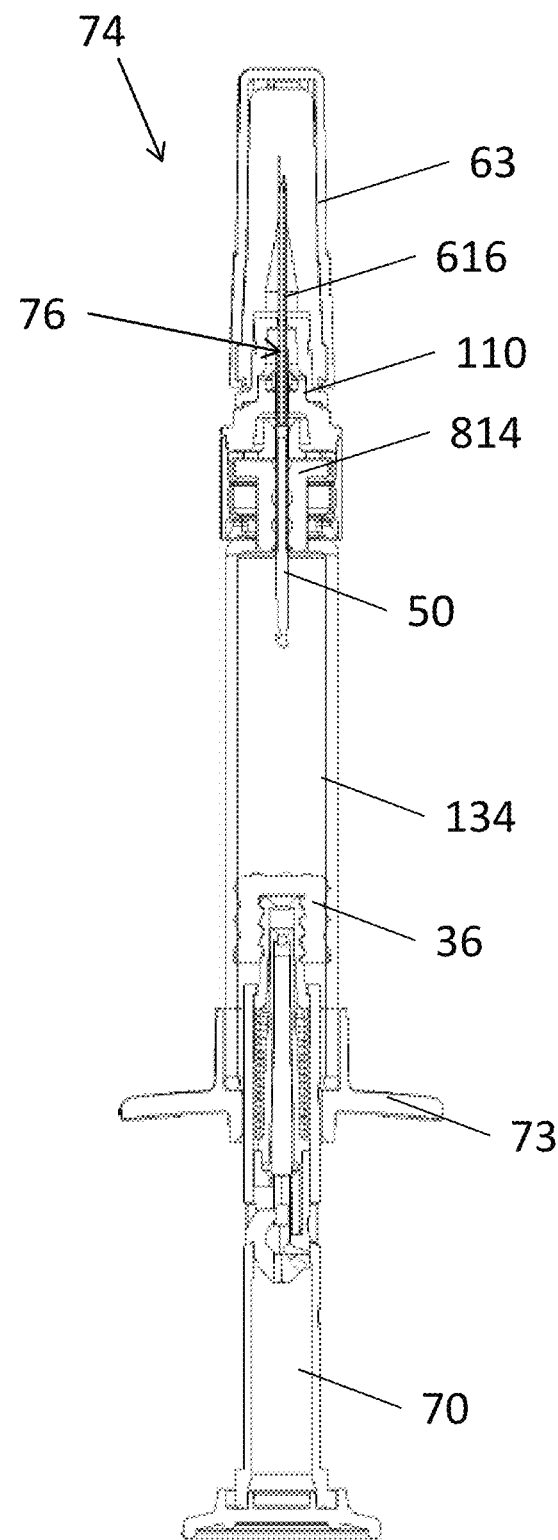
Figure 25E:
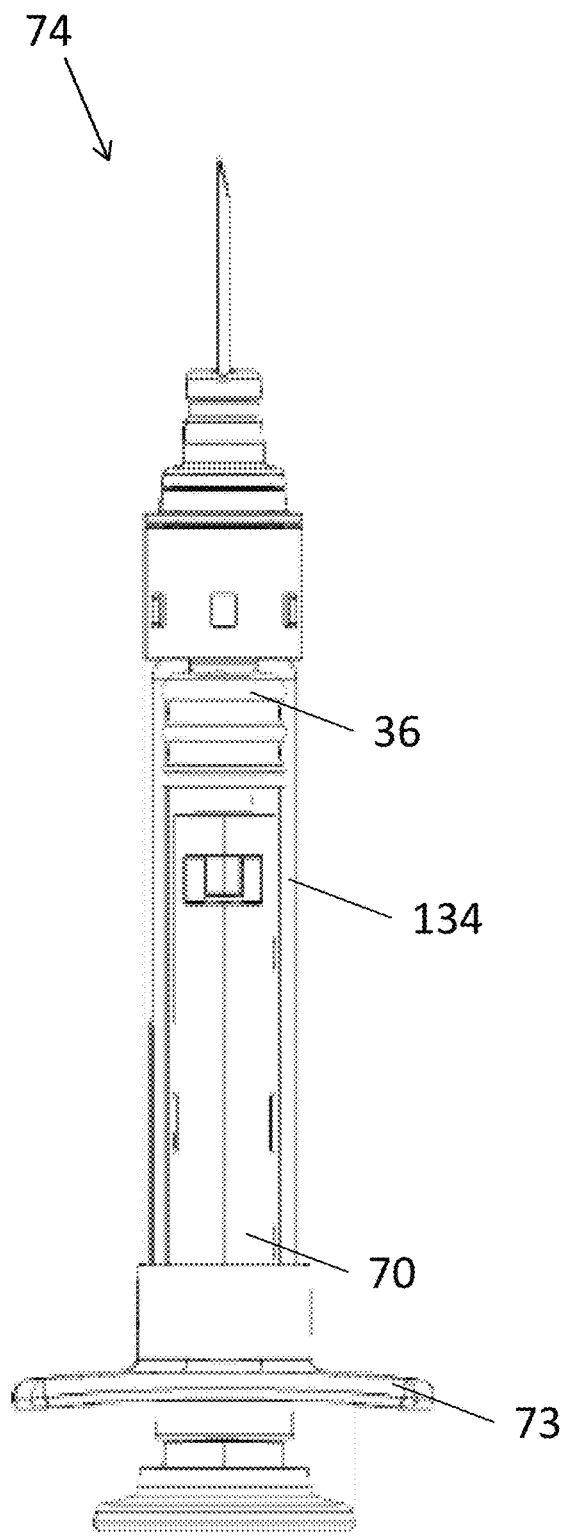
Figure 25F:
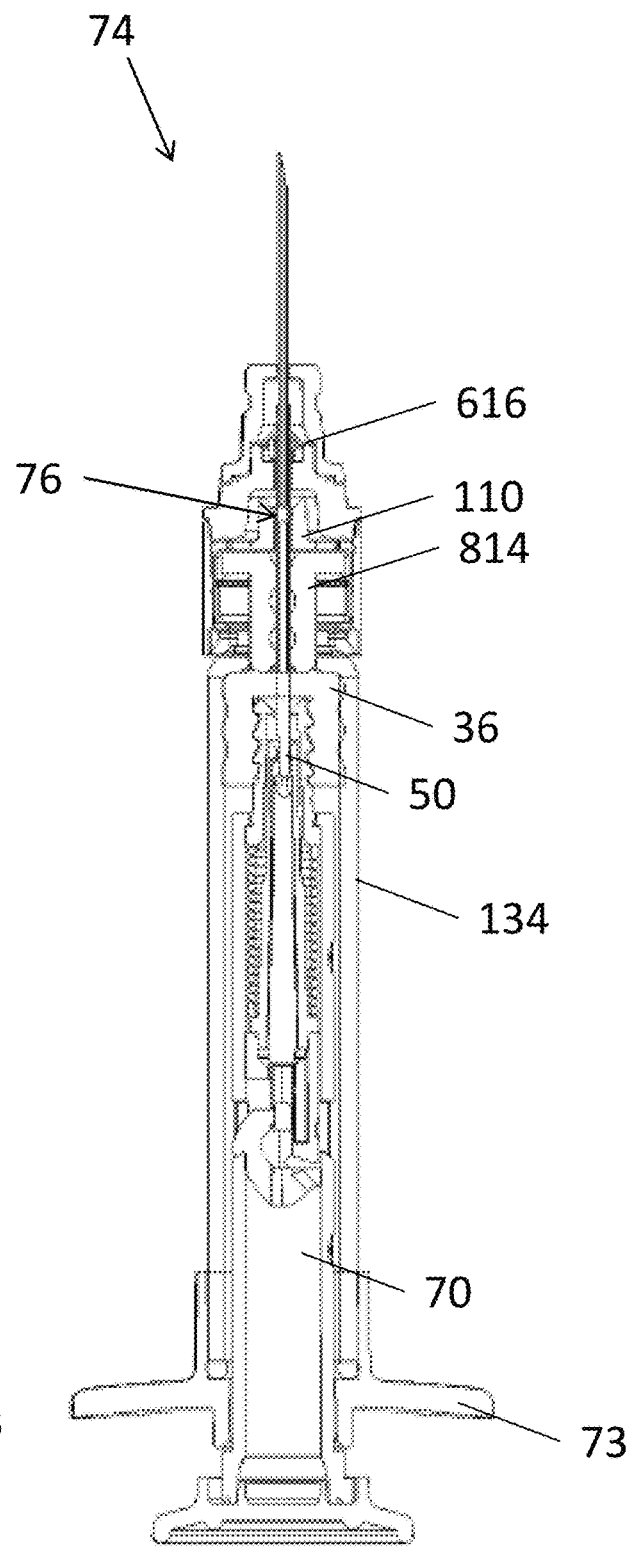
Figure 25G:
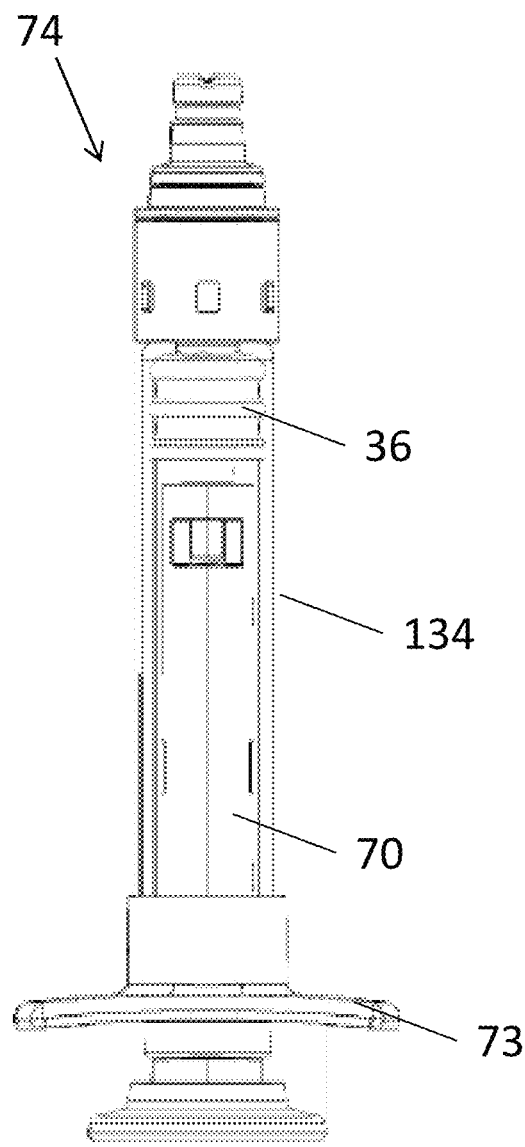
Figure 25H:
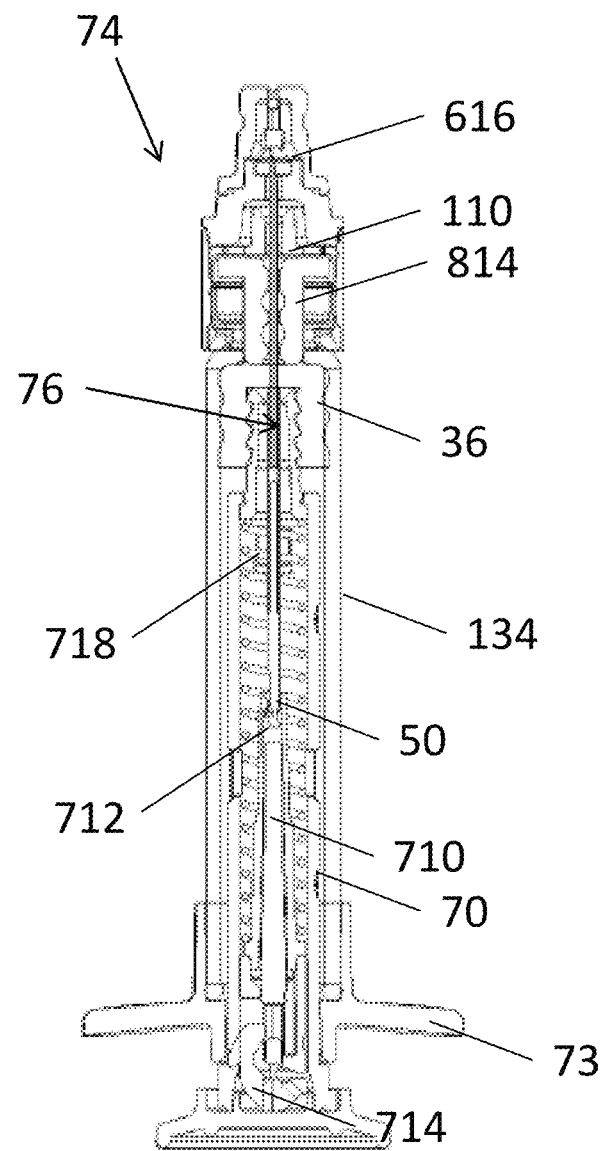

FIGS. 24A to 24R depict a method of assembling a cartridge safe injection system and performing an injection using same according to one embodiment. FIGS. 24A and 24B depict a needle hub assembly (74) as shipped, which includes a point protector (82) removably coupled thereto. FIGS. 24C and 24D depict the needle hub assembly (74) as shipped disposed over a cartridge (134). FIGS. 24E and 24F depict the needle hub assembly (74) with the point protector (82) removed. FIGS. 24G and 24H depict the needle hub assembly (74) disposed over the cartridge (134), with the point protective (82) removed from the needle hub assembly (74). As shown in FIG. 24H, the secondary/backup seal (110) is in a proximal position ready for the assembly of the needle hub assembly (74) and the cartridge (134). As described above, in the proximal position, the secondary/backup seal (110) prevents premature needle latch (616) disengagement during safe injection system assembly.

FIGS. 24I and 24J depict the needle hub assembly (74) assembled with (i.e.: coupled onto) the cartridge (134), As shown in FIG. 24J, the secondary/backup seal (110) is in a distal position ready for distal movement of the needle spine assembly (76) to disengage the needle latch at the end of an injection. FIGS. 24I and 24J illustrate assembly of the needle hub assembly (74) and the cartridge (134).

FIGS. 24K and 24L depict complete assembly of the cartridge safe injection system. The assembly is completed by addition of a finger flange (73) and a plunger rod (70). The plunger rod (70) may be coupled to (e.g., screwed into) a stopper member (36) in the proximal end of the cartridge (134). Complete assembly of the cartridge safe injection system readies the system for injection. The steps depicted in FIGS. 24A-24J or 24L may be performed at a factory rather than directly before an injection is to be given. The fully assembled cartridge safe injection system may be stored and/or transported.

FIGS. 24M and 24N depict removal of a needle cover member (63; see FIGS. 24K and 24L) from the needle hub assembly (74) and complete injection of an injectable substance from the interior of the cartridge (134) with distally directed pressure applied to the plunger rod (70) to move the stopper member (36) distally inside of the cartridge (134). With complete seating of the stopper member (36) into the cartridge (134), the needle proximal end (50) is stabbed through the stopper member (36). Elastic deformation of the material comprising the stopper member (36) allows the stopper member (36) to reach the bottom of the cartridge (134) to expel all of the injectable substance, and trigger an energy-storing member (718) to retract the needle while accounting for geometric variation of cartridge (134) and other components due to manufacturing and assembly tolerances. A needle retention feature (712) is configured to prevent pull-out of the needle proximal end (50) once it has been stabbed into and captured by the needle retention feature (712). The capturing interaction between the needle retention feature (712) and a proximal end harpoon of the needle proximal end (50) is configured to allow relatively easy motion (using less force) in the compressive/coupling direction (i.e., during the stabbing-in motion with the proximal end harpoon of the needle proximal end (50)), and relatively difficult motion (withstanding more force) in the axial tension/decoupling motion (i.e., with a needle retracting load from the plunger assembly to pull the needle distal tip (48) into a safe configuration).

With complete insertion of the stopper member (36), the needle latch (616) is configured to become unseated from its previous latched position in the groove (111) on the needle joining member (83), as shown in FIGS. 24O (latched) and 24P (unlatched), to allow for retraction of the needle spine assembly (76). Concomitantly, the needle proximal end (50) is configured to directly abut or compress against an unlatching member (710) or rod that is configured to allow a rotatable latching member (714) to transform from a latched condition to an unlatching condition. In this latched condition, a load generated by a compressed energy-storing member (718), such as a spring, is reacted/opposed by the geometric state of the latching member (714), maintaining the compressed state of the energy-storing member (718). In the unlatching condition, the load generated by the compressed energy-storing member (718) is released and retracts the needle spine assembly (76) at least partially into the plunger rod (70) such that the distal end of the needle distal tip (48) is retracted at least into the needle hub assembly (74) such that no sharp surface is exposed (see FIGS. 24Q and 24R). After the needle distal tip (48) is retracted at least into the needle hub assembly (74), the cartridge safe injection system is in a "safe" condition for disposal while minimizing the risk of an unintentional needle stick.

FIGS. 25A-25H depict a method of assembling a cartridge safe injection system and performing an injection using same according to another embodiment. The method depicted in FIGS. 25A-25H is similar to the method depicted in FIGS. 24A to 24R and described above. The differences between the two methods are: (A) the finger flange (73) and the plunger rod (70) are attached to the cartridge (134) before the needle hub assembly (74) is coupled thereto; and (B) a distal seal (814) is coupled to the flange portion (222) of the cartridge (134) before the cartridge (134) is coupled to the needle hub assembly (74). The cartridge cap (72) may be present, or may be omitted as the distal seal (814) may be held in place on the cartridge (134) by the needle hub assembly (74) alone.

FIGS. 24A to 25H depict cartridges which have been filled with a drug, capped, and the needle hub assembly (74) attached. An alternative order of assembly would be to first attach the needle hub assembly (74) to the cartridge without the plunger tip (34) installed. Then, filling of the drug would be from the open proximal end (214, see FIGS. 6A and 6B) of the cartridge (134). The plunger tip (34) would then be installed to contain the drug in the cartridge (134).

As shown in FIGS. 9A-9B, the distal seal (814) has a proximal facing cartridge sealing surface (816) and a proximally projecting cartridge sealing surface (818). The interior of the distal seal (814) also includes at least one sealing gland (820) for sealing against the external surfaces of the needle.

Figure 26A:
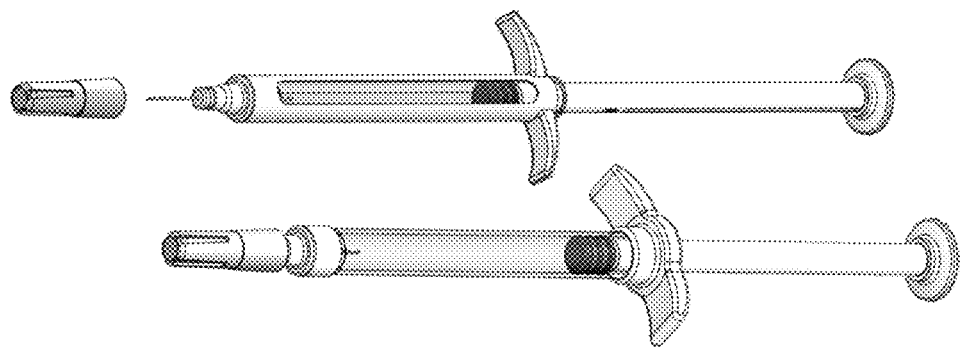
FIG. 26A depicts cartridge safe injection systems having finger flanges according to two embodiments.
Figure 26B:
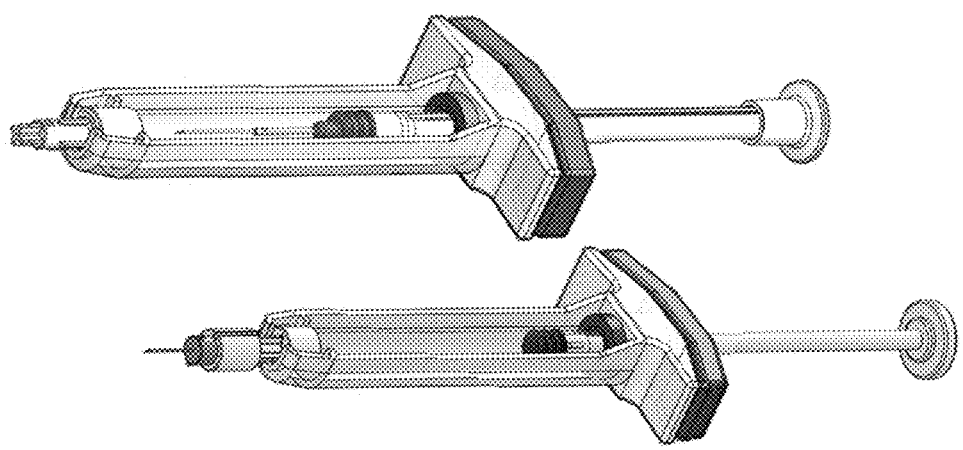
FIG. 26B depicts reusable cartridge safe injection systems having finger flanges according to two other embodiments.

FIG. 26A depicts a finger flange design for use with a cartridge according to two embodiments. The top portion of FIG. 26A depicts an integral sleeve/skirt (see below)/finger flange for use with a cartridge. FIG. 26B represents two reusable cartridge holders, which include a finger flange similar to those depicted in FIG. 26A.

Various features of safe injection systems built around a cartridge (134) can also be used with auto injectors or pen injectors. The cartridges (134) and stopper members (36) in the embodiments described herein may be off-the-shelf (i.e., bulk manufactured and/or sold as a fungible commodity). The cartridges of these systems may also incorporate an integral glass or plastic finger flange similar to what is employed on the syringe based systems.

Protective Cartridge Sleeve

Figure 27:
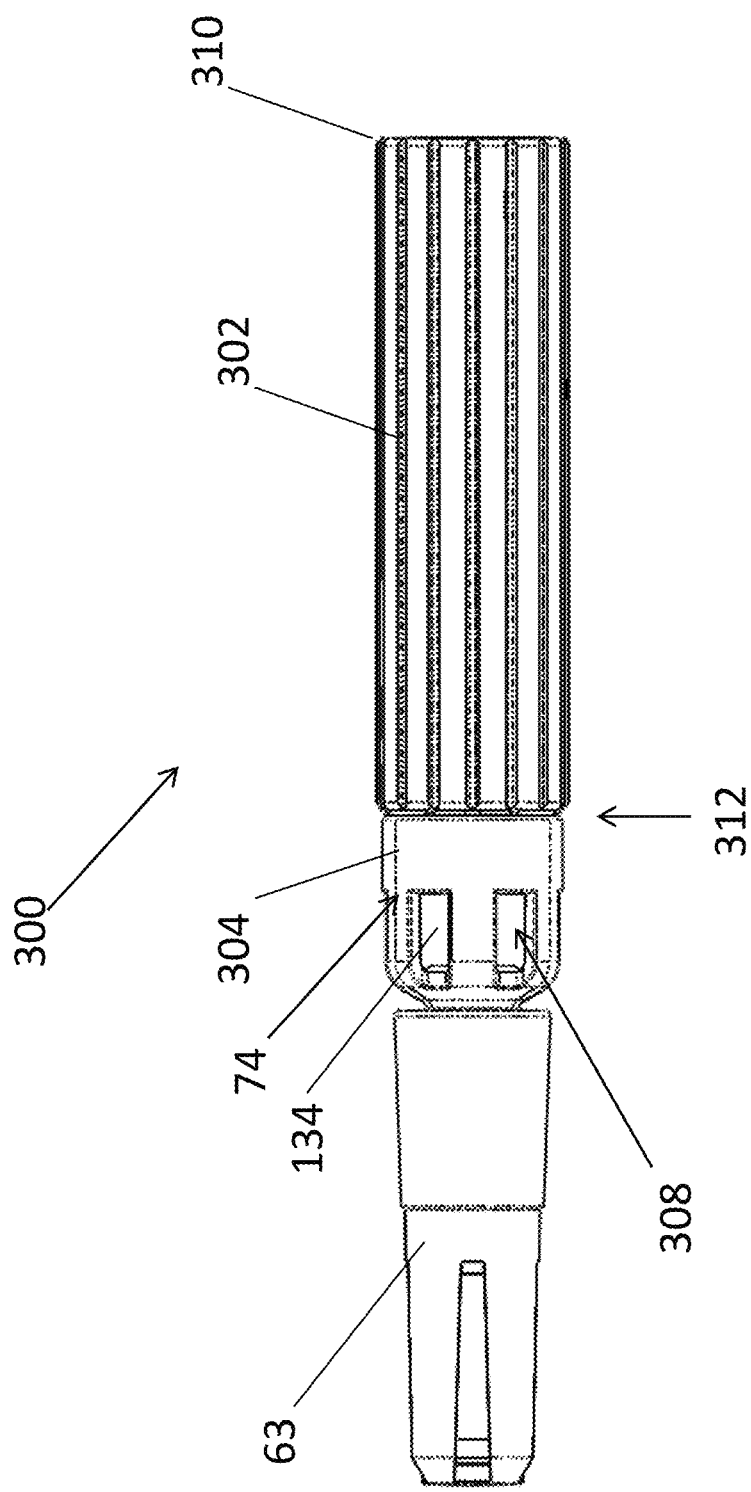

FIGS. 27-41 depict a cartridge safe injection system, and the constituent components of same including a cartridge (134) having a protective sleeve (300) disposed over at least a portion of the cartridge (134) according to one embodiment. FIG. 27 illustrates that the sleeve (300) includes a proximal portion (302) and a distal portion (304). The proximal and distal portions (302, 304) are removably coupled to each other by a plurality of breakable tabs (306). The sleeve (300) can be made from an elastic material (e.g., a polymer) that cushions the cartridge (134), which may be made from a more breakable material (e.g., glass).

The cartridge (134) shown in FIG. 27 is visible through the openings (308) in the distal portion (304) of the sleeve (300), because the sleeve (300) is disposed over the cartridge (134) such that it covers the entire cartridge (134). For instance, a proximal end (310) of the sleeve (300) extends either at or proximal of a proximal end of the cartridge (134). Further, the distal portion (304) of the sleeve (300) is coupled to the cartridge (134) (e.g., to the flange portion (222) of the cartridge (134) with an interference fit). Consequently, the sleeve (300) is coupled to the cartridge (134), and a portion of the sleeve (i.e., the proximal portion (302)) is removably coupled to the cartridge (134) by virtue of the proximal portion (302) of the sleeve (300) being removably coupled to the distal portion (304) of the sleeve (300). As such, the sleeve (300) is "partially removably coupled" to the cartridge (134).

The distal portion (304) of the sleeve (300) also releasably couples a needle spine assembly (76) to the cartridge (134). The distal portion (304) of the sleeve (300) includes sections that are structurally and functionally similar to the following portions of the needle hub assembly (74) depicted in FIG. 20: proximal portion (78); distal portion (80); and skirt (136), The sections of the distal portion (304) of the sleeve (300) are also structurally and functionally similar to the needle coupling assembly (606) and the snap over interface (822) of the retractable safety needle (810), depicted in FIG. 9A.

Figure 28:
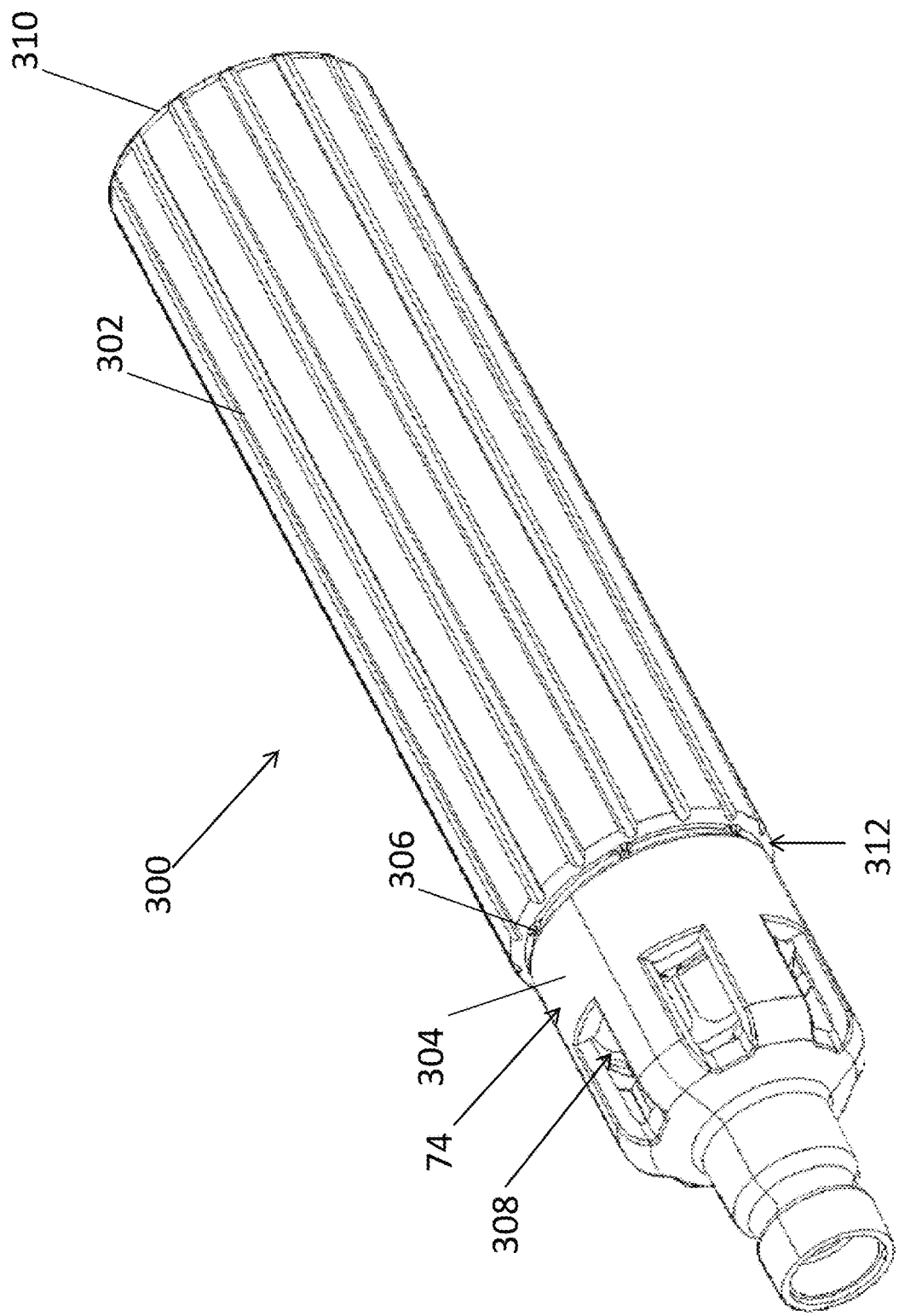
Figure 29:
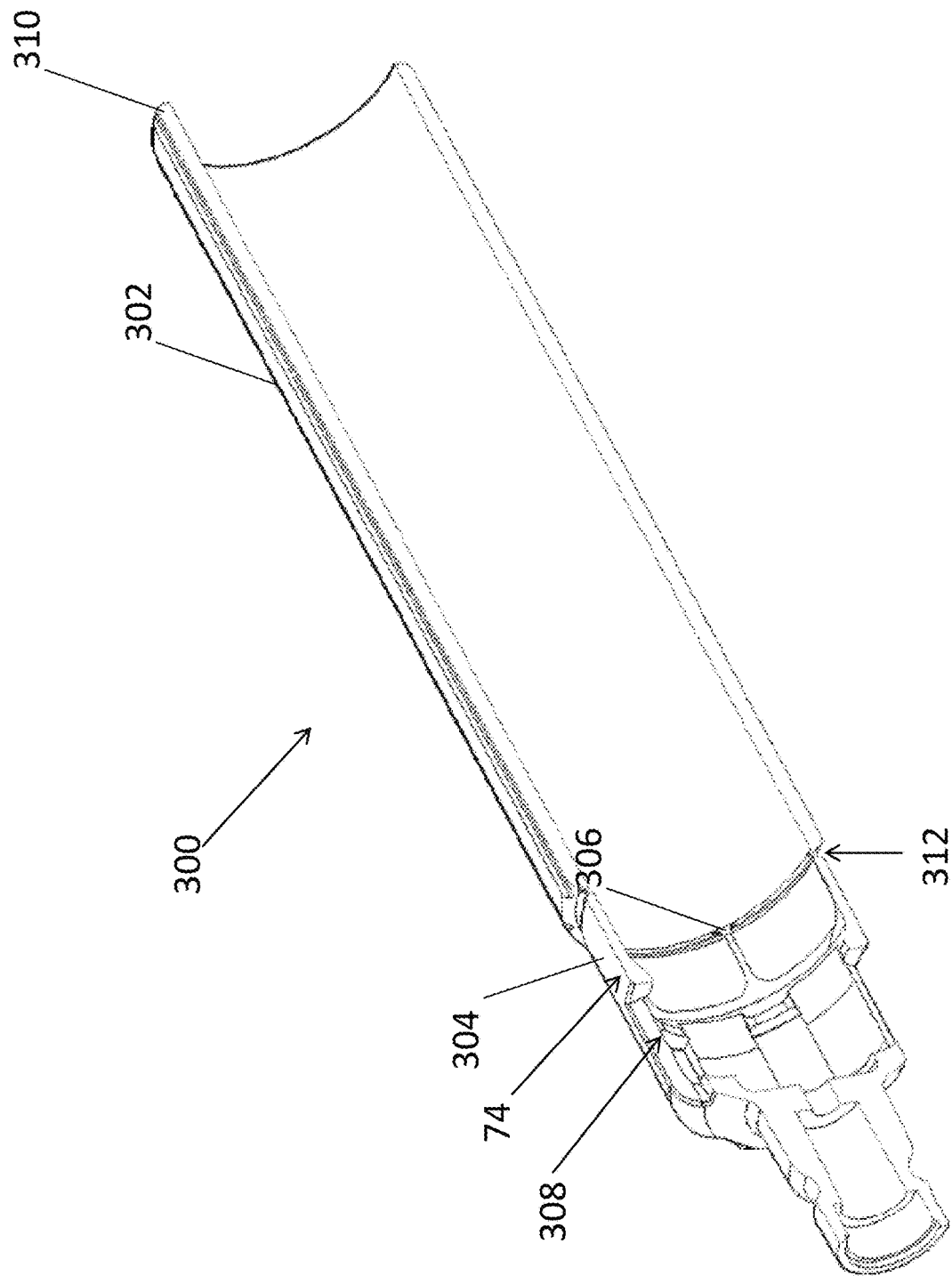
Figure 30:
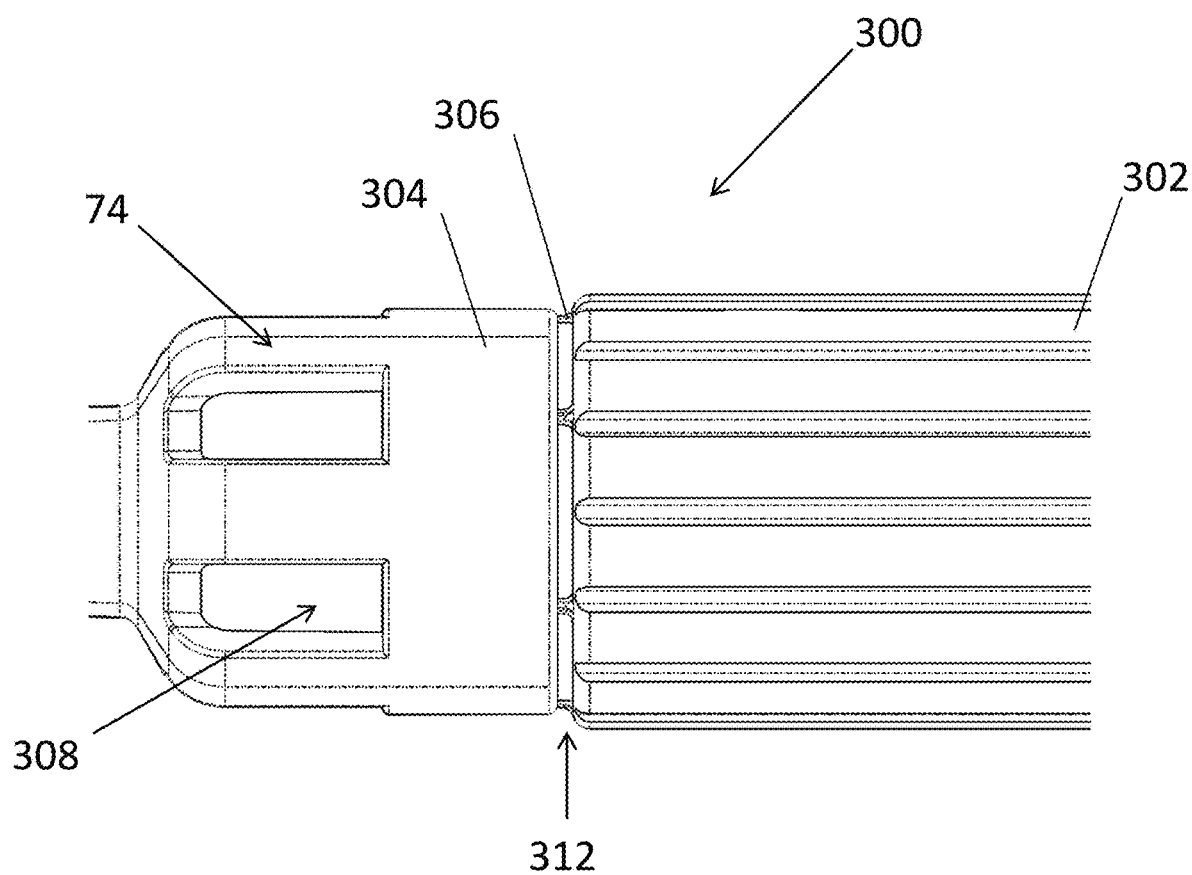
Figure 31:
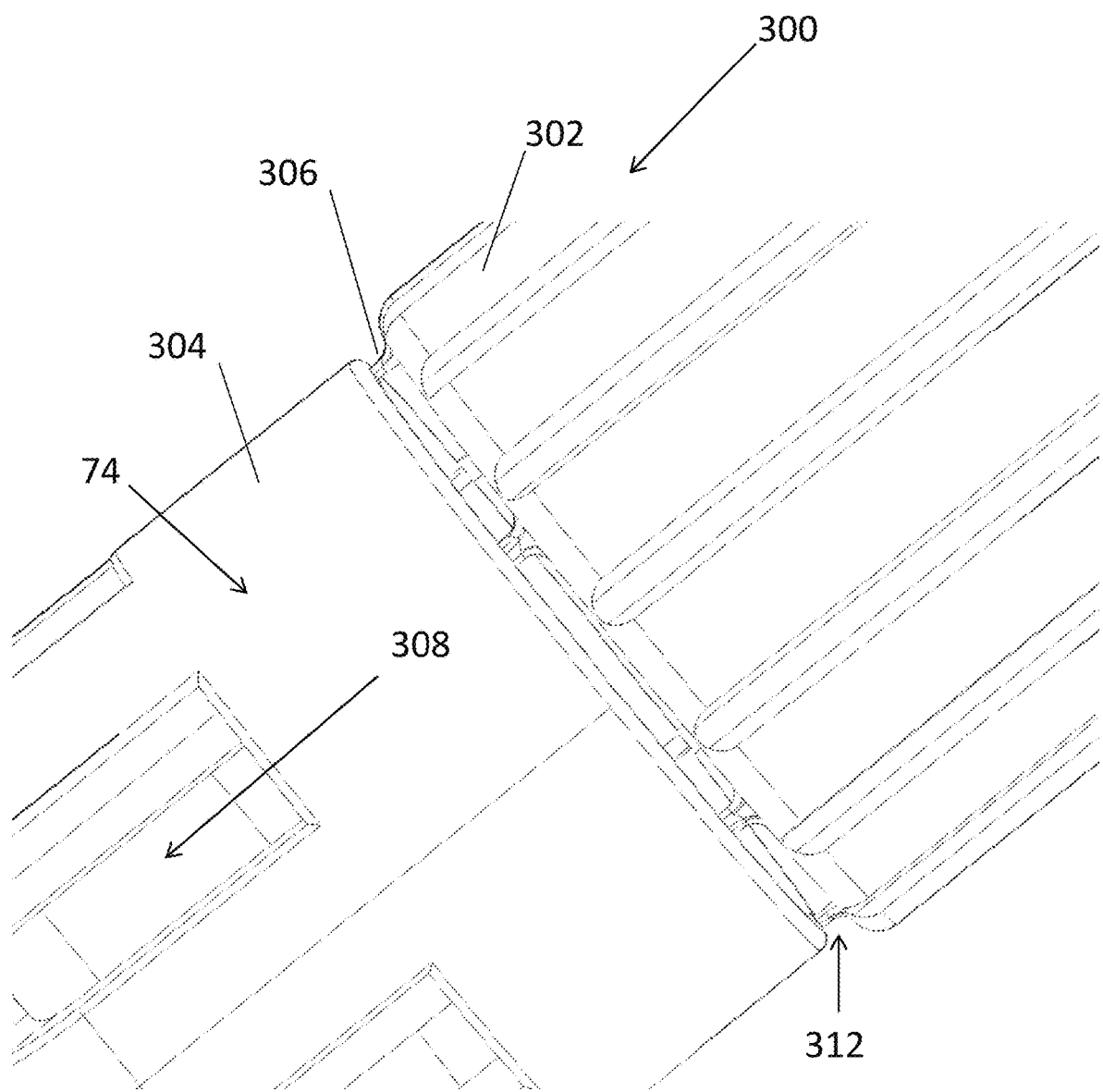
Figure 32:
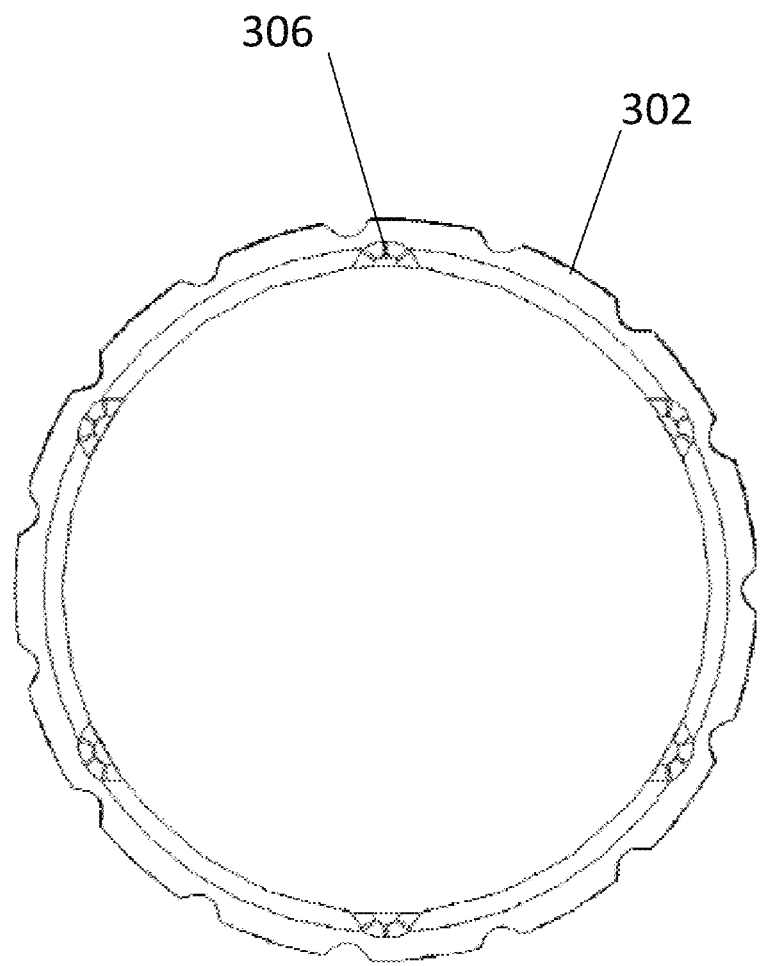

FIGS. 28 and 29 depict the sleeve (300) before installation on a cartridge (134). FIGS. 30 and 31 depict the interface (312) between the proximal and distal portions (302, 304) of the sleeve (300) in greater detail. FIG. 31 shows that the proximal and distal portions (302, 304) of the sleeve (300) are removably coupled to each other with a plurality of breakaway tabs (306). As shown in the axial cross-sectional view in FIG. 32, the embodiment depicted in FIGS. 27-41 includes six breakaway tabs (306) that removably couple the proximal and distal portions (302, 304) of the sleeve (300).

Figure 33:
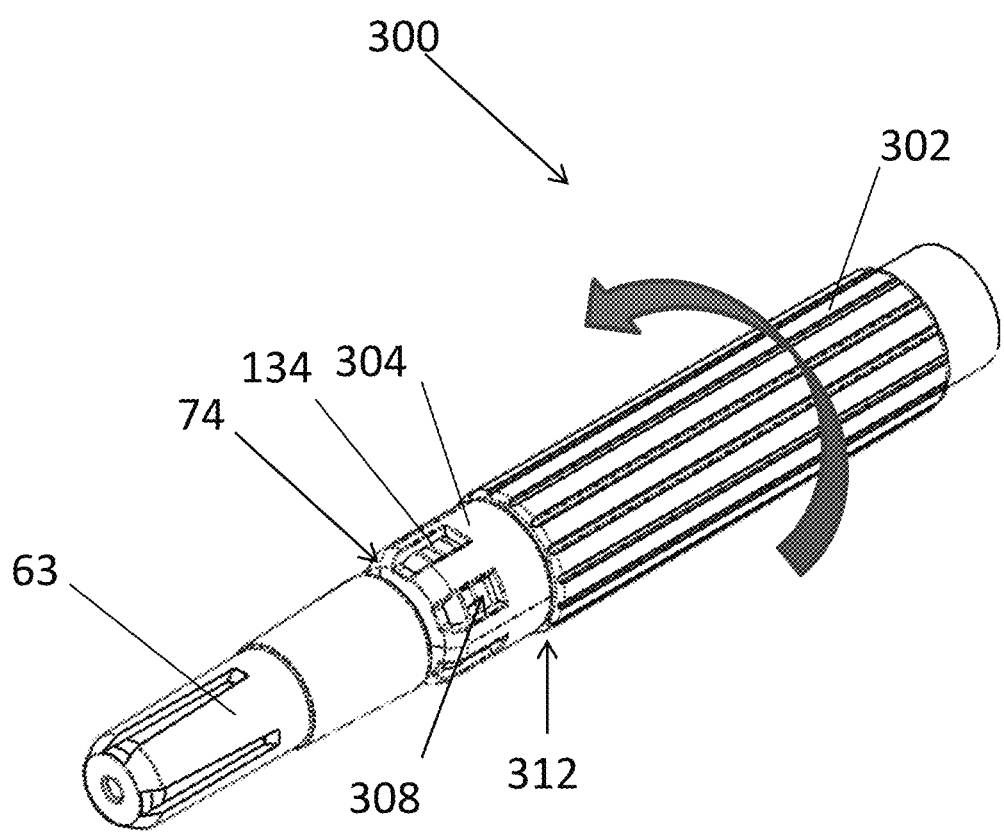
Figure 34:
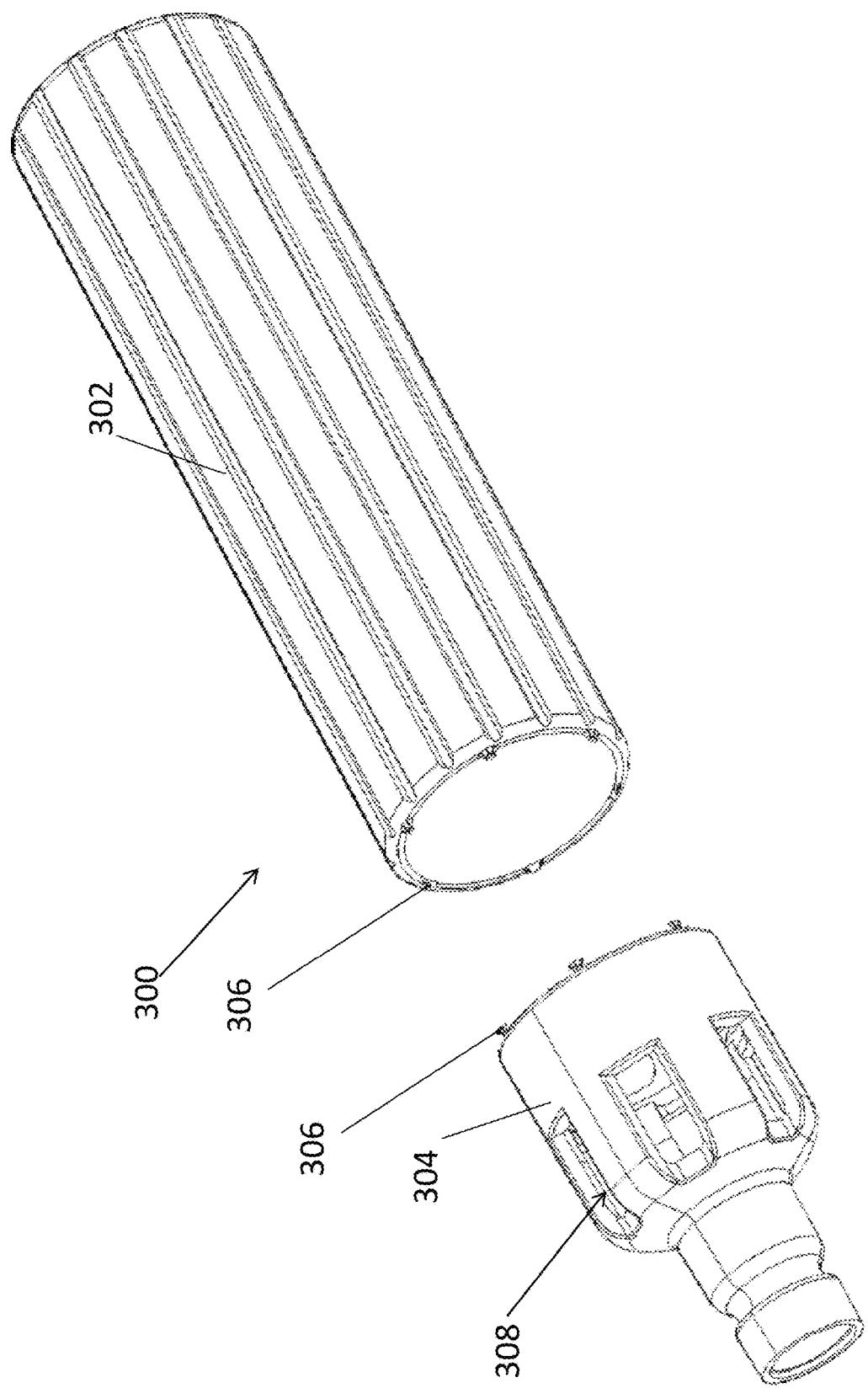
Figure 35:
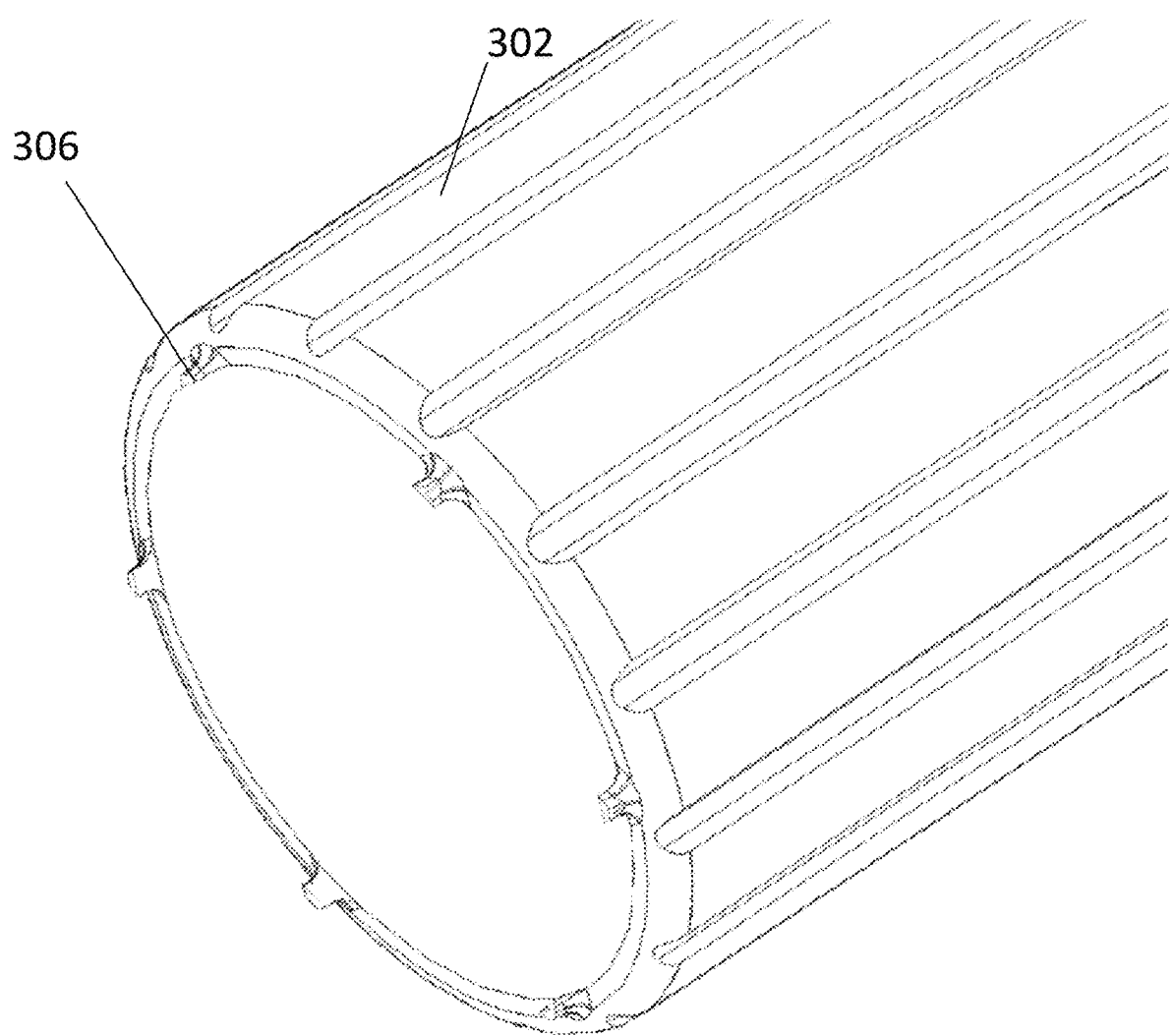
Figure 36:
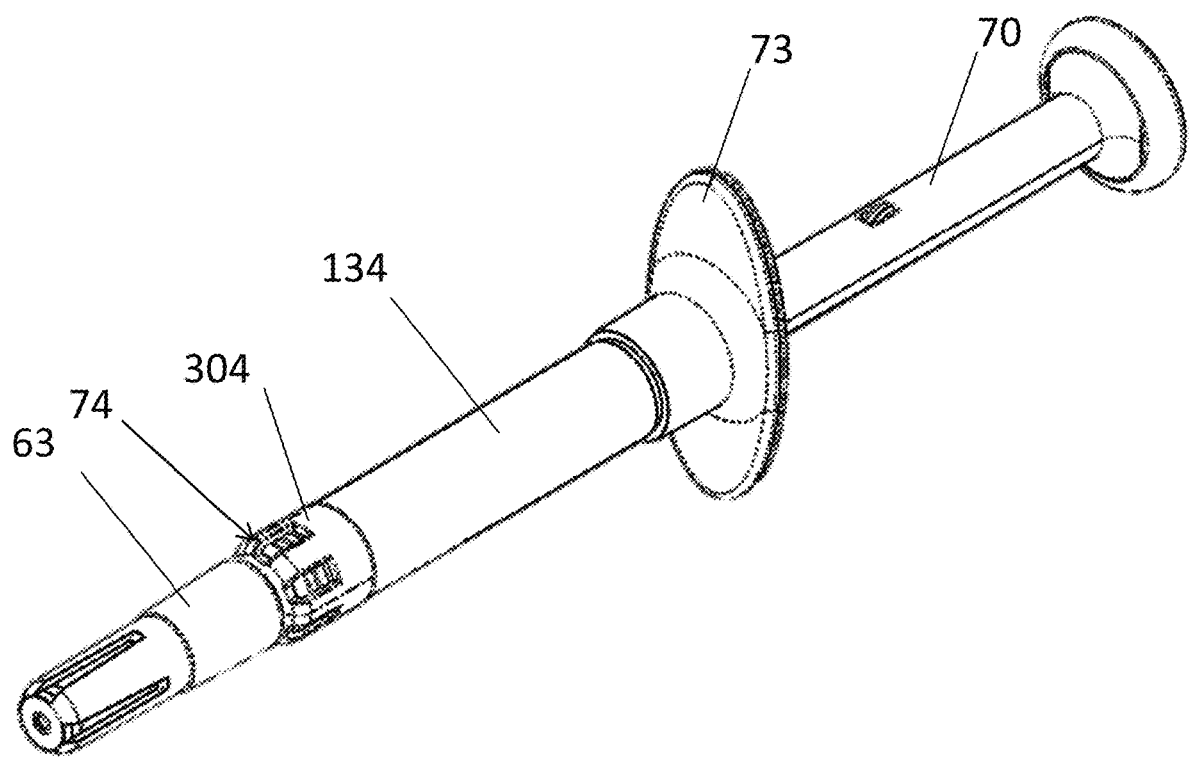
Figure 37:
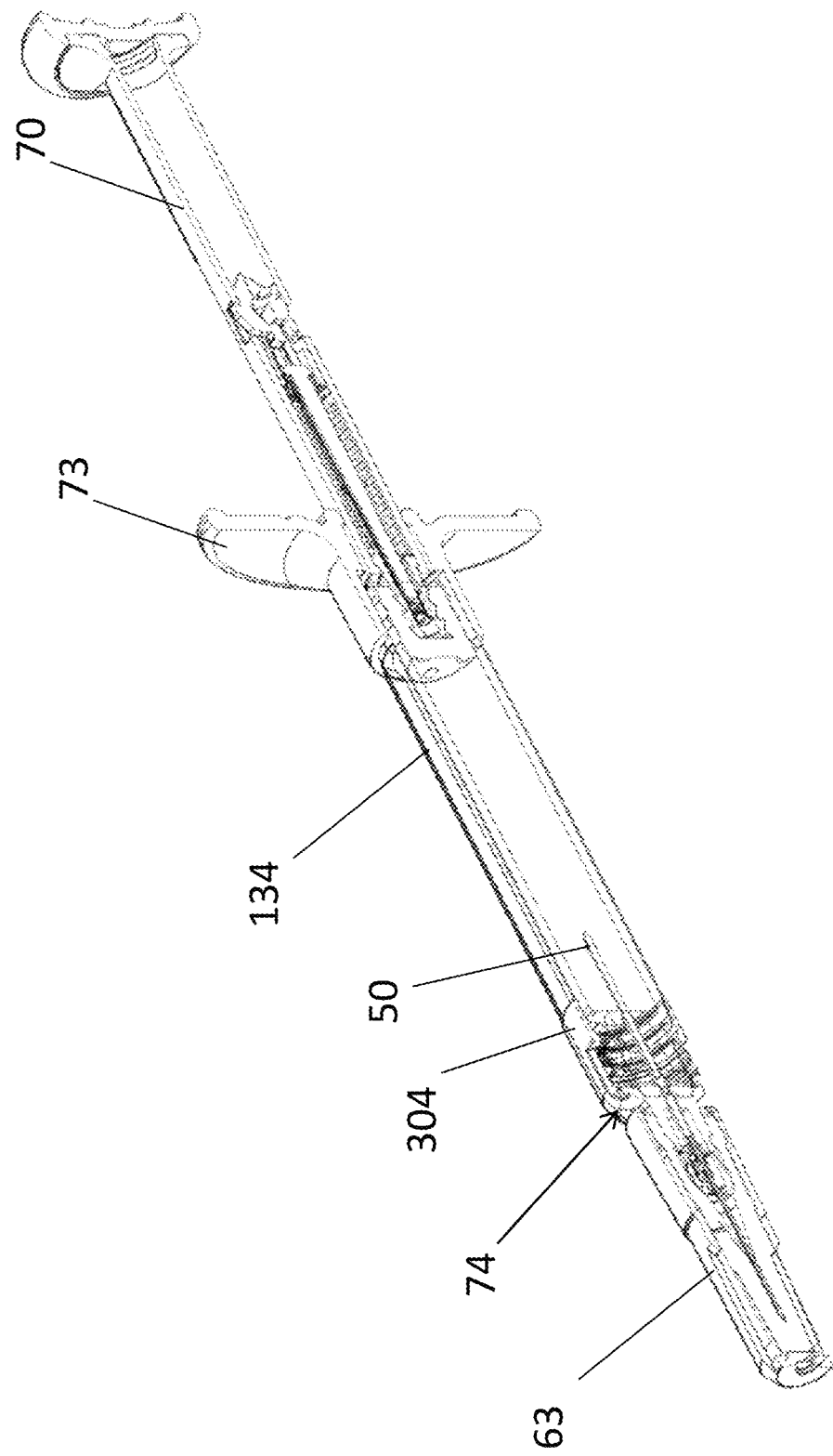
Figure 38:
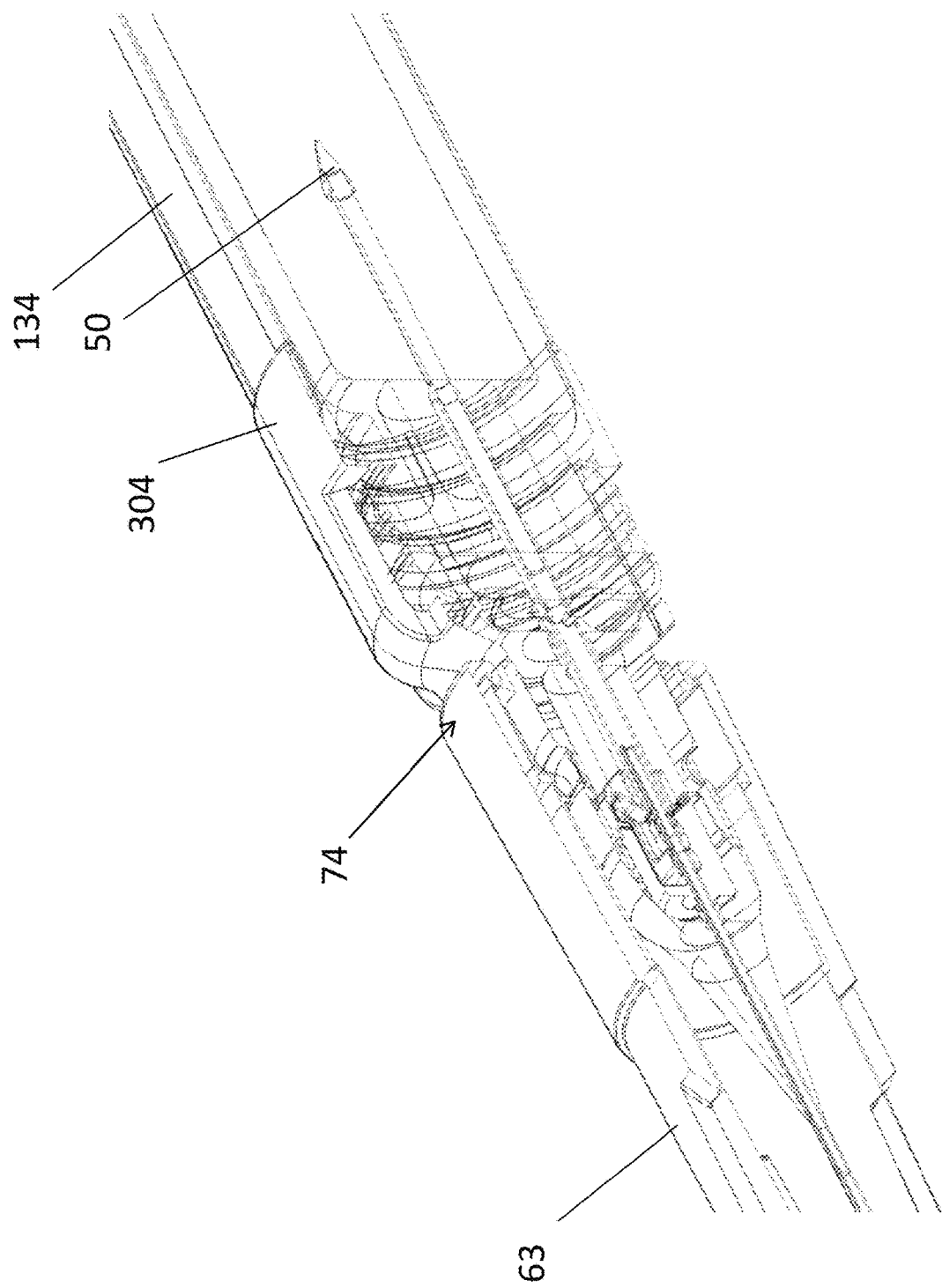

FIG. 33 depicts one method of separating/uncoupling the proximal and distal portions (302, 304) of the sleeve (300). In this embodiment, the proximal and distal portions (302, 304) of the sleeve (300) can be uncoupled from each other by twisting the proximal portion (302) relative to the distal portion (304). This relative rotating motion stretches the breakaway tabs (306) until the tabs (306) reach their breaking point, at which the tabs (306) or broken as shown in FIG. 34. FIG. 35 illustrates the distal end of the proximal portion (302) after it has been separated/uncoupled from the distal portion (304). While FIG. 33 depicts separating/uncoupling using a twisting motion, the proximal and distal portions (302, 304) of the sleeve (300) can also be separated/uncoupled from each other using other methods. In one embodiment, the proximal and distal portions (302, 304) of the sleeve (300) can be separated/uncoupled from each by pulling the proximal and distal portions (302, 304) apart from each other along the longitudinal axis. In another embodiment, the proximal and distal portions (302, 304) of the sleeve (300) can be separated/uncoupled from each by cutting or melting the breakaway tabs (306). In another embodiment, the proximal and distal portions (302, 304) may be connected via a thread, snap fit, press fit, or other releasable mechanical connection. In still other embodiments, the various methods of separating/uncoupling the proximal and distal portions (302, 304) of the sleeve (300) from each other can be combined either simultaneously and/or serially.

Figure 39:
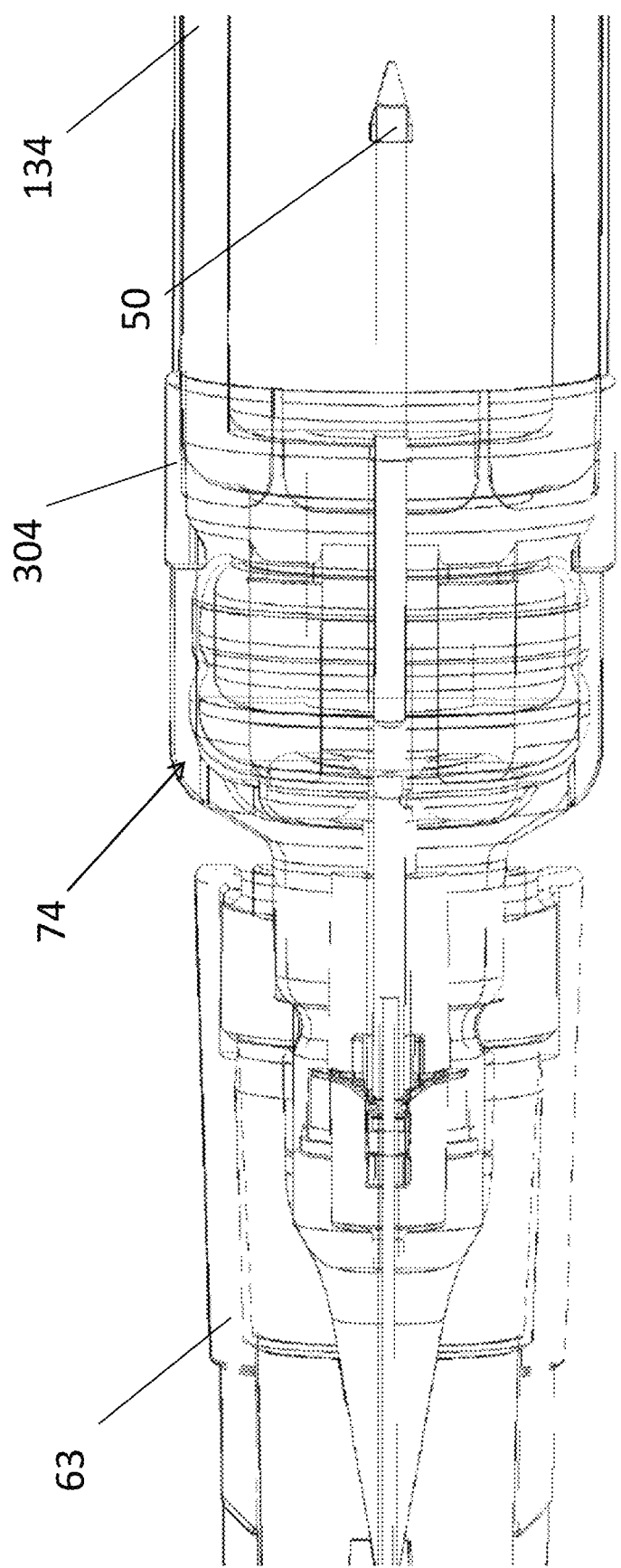

FIGS. 36-39 depict a safe injection system including a distal portion (304) of a protective sleeve (300) after the proximal portion (302) has been separated from the distal portion (304) and removed for system assembly. The safety needle injection system includes a plunger rod assembly (70), a finger flange (73), a cartridge (134), and a needle hub assembly (74), which includes the distal portion (304) of the protective sleeve (300). As shown in FIG. 39, the distal portion (304) of the protective sleeve (300) couples the needle hub assembly (74) to the flange portion (222) of the cartridge (134) with an interference fit.

Figure 41:
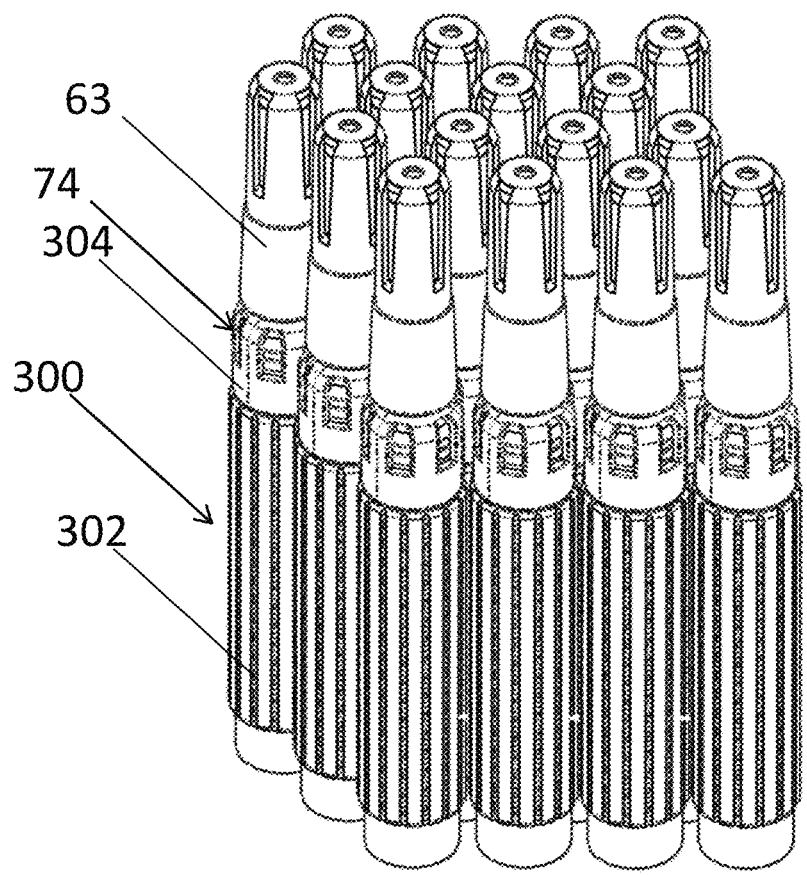

FIGS. 40A, 40B, and 41 depict the advantages of various embodiments including a protective sleeve (300). FIGS. 40A and 40B depicts an embodiment wherein the protective sleeve (300) has been coupled to a needle hub assembly (74) before coupling with a cartridge (134). An outer diameter of the distal portion (304) of the protective sleeve (300) is larger than inner diameter of the proximal portion (302) of the protective sleeve (300). Consequently, even when a needle cover member (63-1) of a first needle hub assembly (74-1) finds its way into the proximal end (310-2) of a second needle hub assembly (74-2) (e.g., during storage and transportation of system components), the relative outer and inner diameters of the distal end proximal portions (304-1, 302-2) prevent the needle cover member (63-1) of the first needle hub assembly (74-1) from impinging upon and potentially damaging the needle proximal end (50-2) of the second needle hub assembly (74-2), as shown in FIG. 40B.

FIG. 41 depicts a plurality of cartridges (134) onto which has been assembled respective needle hub assemblies (74) including proximally-extending protective sleeves (300). The sleeves (300) protect the cartridges (134), which may be made of glass, from breakage from impacting with each other during manufacturing, storage, and transportation. The sleeves (300) also allow the cartridges (134) to be stacked without fanning. In this embodiment, the cartridges (134) can be stored with the needle hub assembly (74) and the protective sleeve (300) coupled thereto. Further, the cartridges (134) can be stored with the needle hub assembly (74) and the protective sleeves (300) are easily stackable for automation of the assembly process.

In some embodiments, the sleeve (300) protects the needle proximal ends (50) of digital hub assemblies (74) without the requirement for other components. Further, the dimensions (e.g., diameter, cross-sectional geometry, and length) of the sleeve (300) can be customized to protect a particular needle hub assembly (74) with a particular needle proximal end (50).

Needle Proximal End Protectors

Figure 42A:
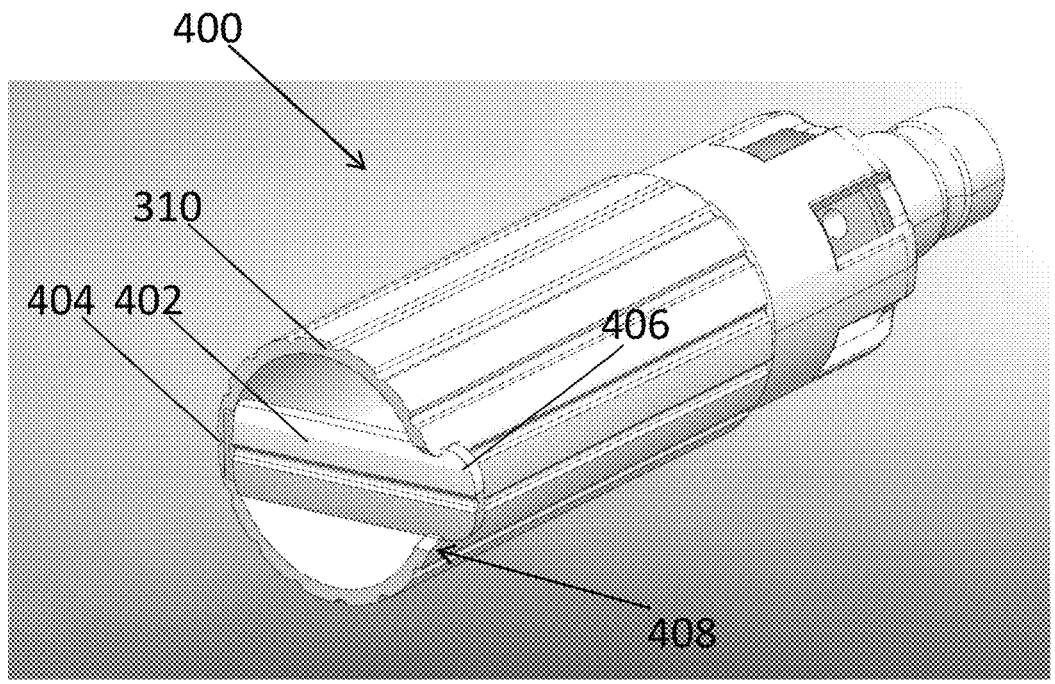
FIGS. 42A and 42B depict needle proximal end protector according to one embodiment.
Figure 42B:
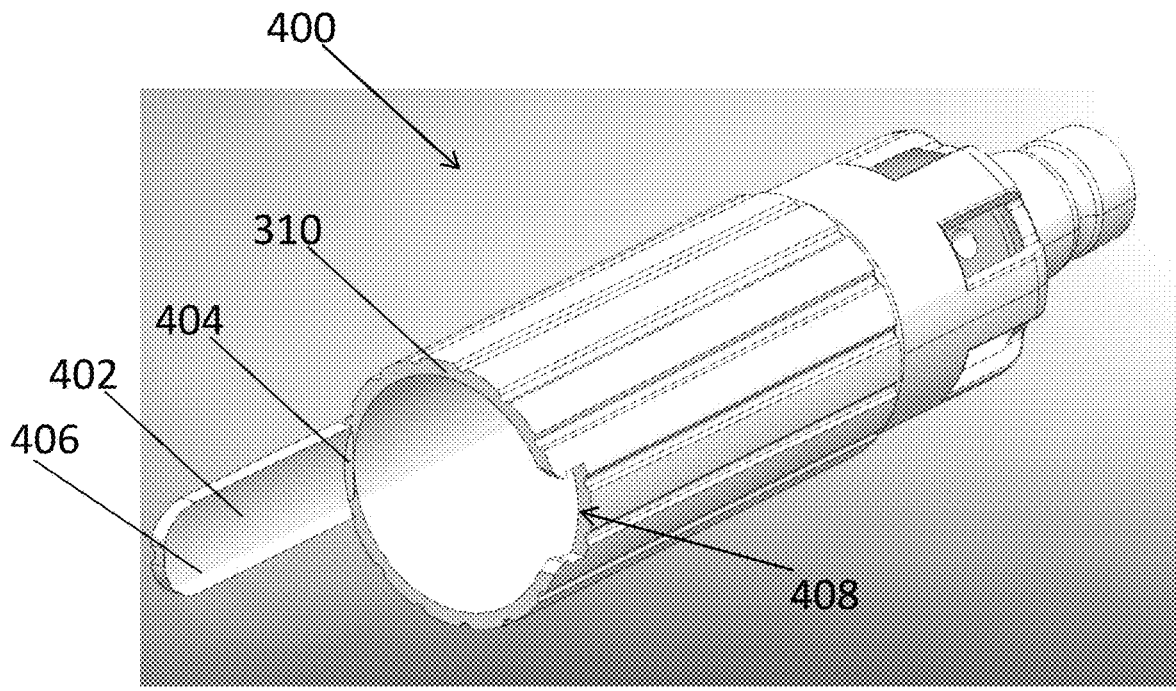

FIGS. 42A-60 depict various embodiments of protectors (400) for needle proximal ends (50) of needle hub assemblies (74). FIGS. 42A and 42B depict a first embodiment of a needle proximal end protector (400) that is similar to the proximally-extending protective sleeve (300) depicted in FIGS. 27-41. Similar to the proximally-extending protective sleeve (300), and the door (402) depicted in FIGS. 42A and 42B, the needle proximal end protector (400) includes proximal and distal portions detachably coupled by a plurality of breakaway tabs. One difference is that the needle proximal end protector (400) includes a door (402) formed at the proximal end (310) of the needle proximal end protector (400). The door (402) is attached to a first portion of the proximal end (310) of the needle proximal end protector (400) with a hinge (404). The door (402) rotates about the hinge (404) between a closed position (FIG. 42A) and an open position (FIG. 42B). In the closed position, a distal end (406) of the door (402) is removably coupled to a second portion of the proximal end (310) of the needle proximal end protector (400) by an interference fit with a notch (408) formed in the second portion. In the closed position, the door (402) forms a radial projection, which at least partially impinges on the internal diameter of the protective sleeve (400) such that the door (402) prevents other components, such as needle cover members (63) of other needle hub assemblies (74) from entering the needle proximal end protector (400) and damaging the needle proximal end (50) of the needle hub assembly (74). One radial projection (402) is shown in this embodiment, however the protector (400) may be configured to have a plurality of radial projections that prevent other components from entering the needle proximal end protector (400). The door (402) also prevents the needle hub assemblies (73) from becoming stuck together during manufacturing, storage, and/or shipping.

Figure 43:
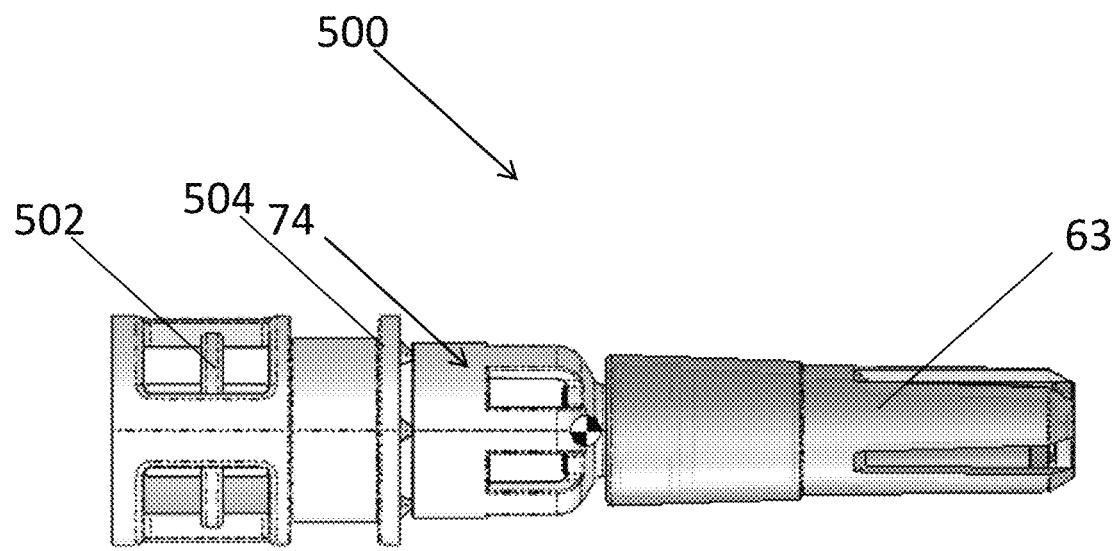
Figure 44:
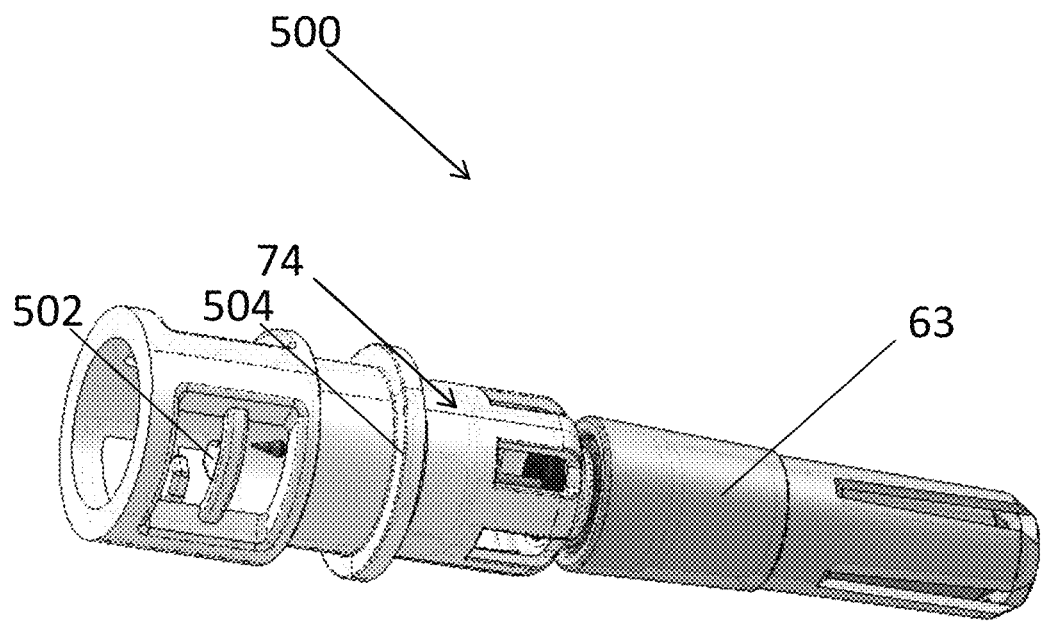

FIGS. 43-48B depict a second embodiment of a needle proximal end protector (500), that is a variation on the embodiment depicted in the FIGS. 42A and 42B, and embodying the same operative concepts. Similar to the proximally-extending protective sleeve (300) depicted in FIGS. 27-41, and the door (402) depicted in FIGS. 42A and 42B, the needle proximal end protector (500) includes proximal and distal portions detachably coupled by a plurality of breakaway tabs. One difference (see FIG. 44) is that the proximal portion of the needle proximal end protector (500) includes a plurality (e.g., three) of movable tabs (502) that reduce the inner diameter of the proximal end (310) of the needle proximal end protector (500), thereby preventing other components, such as needle cover members (63) of other needle hub assemblies (74) from entering the needle proximal end protector (500) and damaging the needle proximal end (50) of the needle hub assembly (74). The movable tabs (502) are functionally similar to the door (402) in the needle proximal end protector (500) in FIGS. 42A and 42B. FIGS. 43 and 44 also depict a flange (504) disposed on the proximal portion (302) of the needle proximal end protector (500) to facilitate automated (i.e., mechanized) handling of the proximal and distal portions (302, 304) of the needle proximal end protector (500) to allow for pushing and pulling during system assembly and separation of the proximal portion.

FIGS. 45A-45C depict three positions of a movable tab (502) of the needle proximal end protector (500). FIG. 45A depicts the position of the movable tab (502) after the needle proximal end protector (500) has been formed (e.g., molded) and is ready for assembly into a needle hub assembly (74). In the position depicted in FIG. 45A, the movable tab (502) does not reduce the inner diameter of the proximal end (310) of the needle proximal end protector (500). This allows for assembly of the needle hub assembly (74). FIG. 45B depicts the position of the movable tab (502) after a needle hub assembly (74) (not shown) has been formed. In this position, the movable tab (502) reduces the inner diameter of the proximal end (310) of the needle proximal end protector (500), thereby preventing other components, such as needle cover members (63) of other needle hub assemblies (74) from entering the needle proximal end protector (500) and damaging the needle proximal end (50) of the needle hub assembly (74). FIG. 45C depicts the position of the movable tab (502) after a cartridge (134) has been combined with the needle hub assembly (74). Insertion of the cartridge (134) into the proximal end (310) of the needle proximal end protector (500) deforms the movable tab (502) from the position depicted in FIG. 45B to the position depicted in FIG. 45C.

Figure 46:
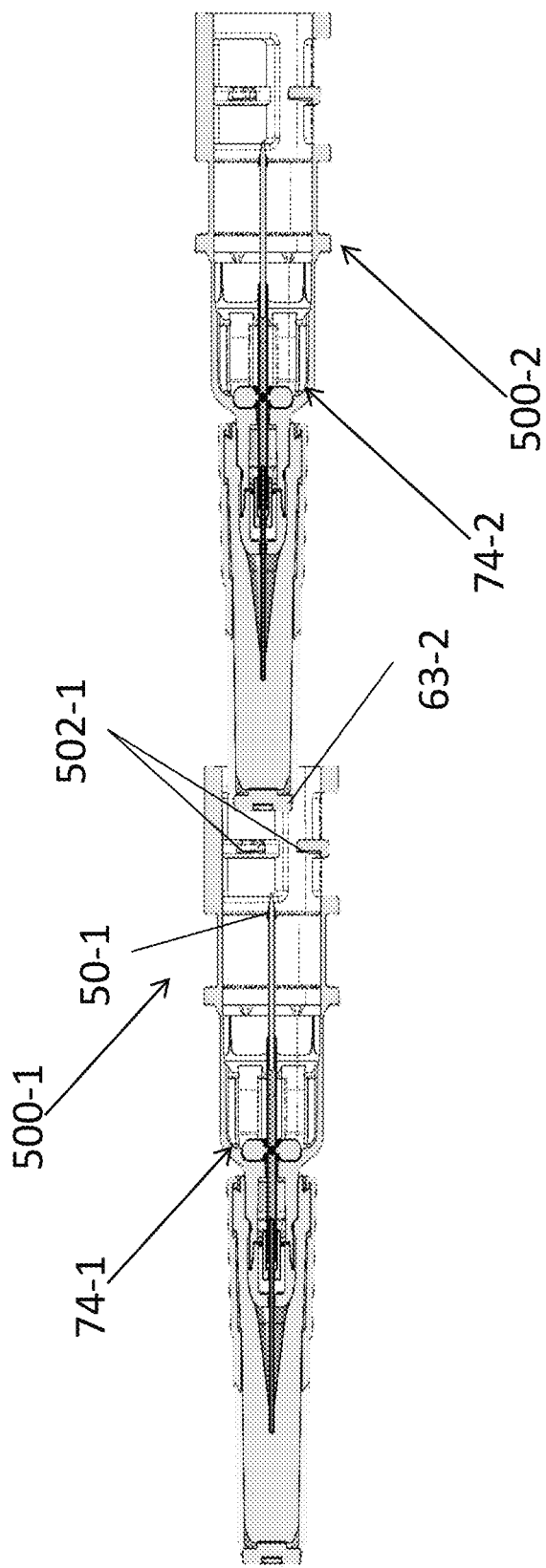
Figure 47A:
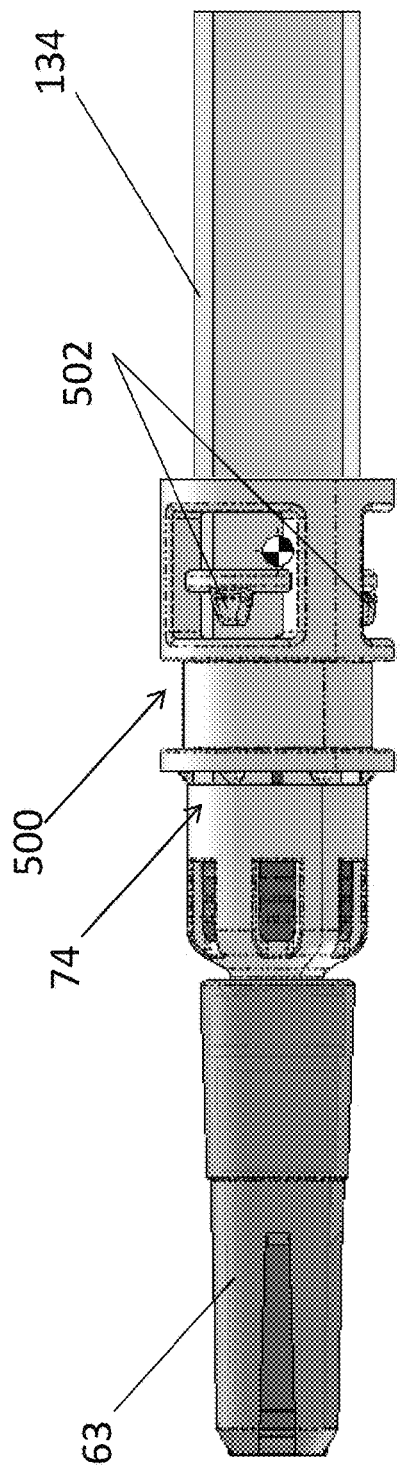
Figure 47B:
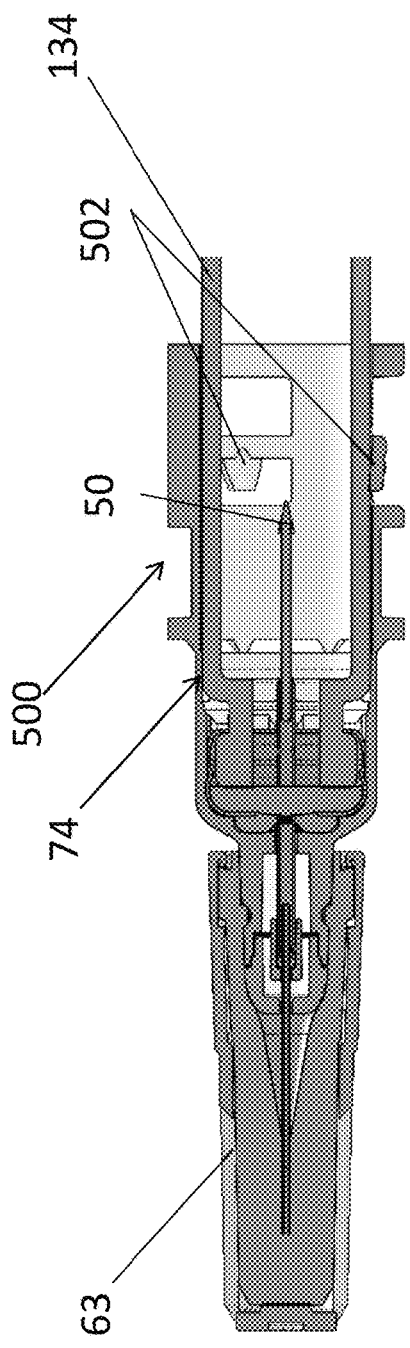
Figure 48A:
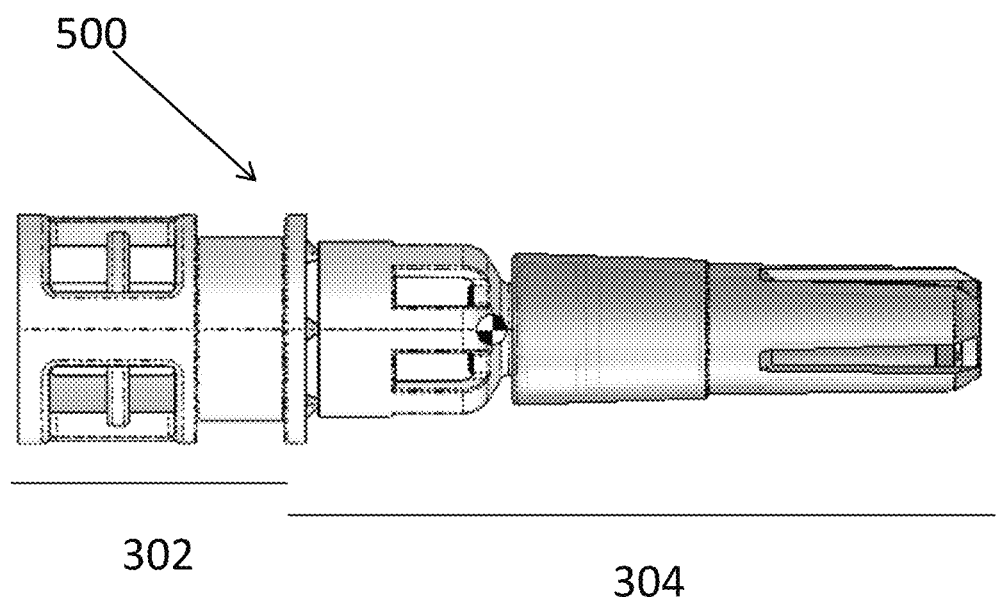
Figure 48B:
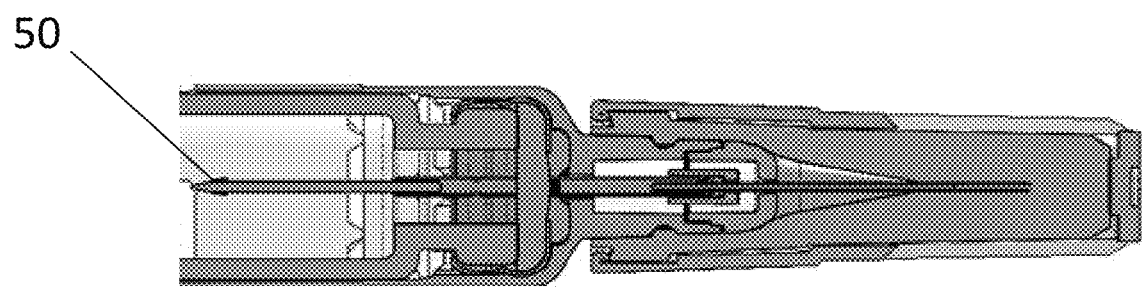

FIG. 46 depicts the reduction in the inner diameter of the proximal end (310) of the needle proximal end protector (500) by the movable tabs (502-1) of a first needle hub assembly (74-1), thereby preventing a needle cover members (63-2) of a second needle hub assemblies (74-2) from entering the first needle proximal end protector (500-1) and damaging the needle proximal end (50-1) of the first needle hub assembly (74-1). Insertion of the cartridge (134) into the proximal end (310) of the needle proximal end protector (500) is shown in FIGS. 47A and 47B. FIGS. 48A and 48B depict some design considerations for the needle proximal end protector (500). The distal portion (304) of the needle proximal end protector (500) forms a part of the needle hub assembly (74), and therefore preferably conforms to the design of the safe injection system. On the other hand, the proximal portion (302) the needle proximal end protector (500) is removed from the needle hub assembly (74) after assembly of the safe injection system. Accordingly, dimensions (e.g., diameter, cross-sectional geometry, and length) of the proximal portion (302) can be modified to accommodate the dimensions of various components of the safe injection system, including the needle proximal end (50), which is shown in FIG. 48B.

FIGS. 49-51C depict a third embodiment of a needle proximal end protector (600), that is another variation on the embodiment depicted in the FIGS. 42A and 42B, and embodying the same operative concepts. This needle end protector (600) is very similar to the proximally-extending protective sleeve (300) depicted in FIGS. 27-41. Similar to the proximally-extending protective sleeve (300), and the door (402) depicted in FIGS. 42A and 42B, the needle proximal end protector (600) includes proximal and distal portions detachably coupled by a plurality of breakaway tabs. Further, various dimensions (e.g., diameter, cross-sectional geometry, and length) of the proximal portion (302) can be modified to prevent other components, such as needle cover members (63) of other needle hub assemblies (74) from entering the needle proximal end protector (600) and damaging the needle proximal end (50) of the needle hub assembly (74). The needle proximal end protector (600) has openings (308') in the proximal portion (302) thereof, in addition to openings (308) in the distal portion (304) thereof. These openings (308, 308') facilitate assembly by allowing grasping of the needle spine assembly (76) with a fixture placed therethrough during piercing of the cartridge seal (72).

Figure 53:
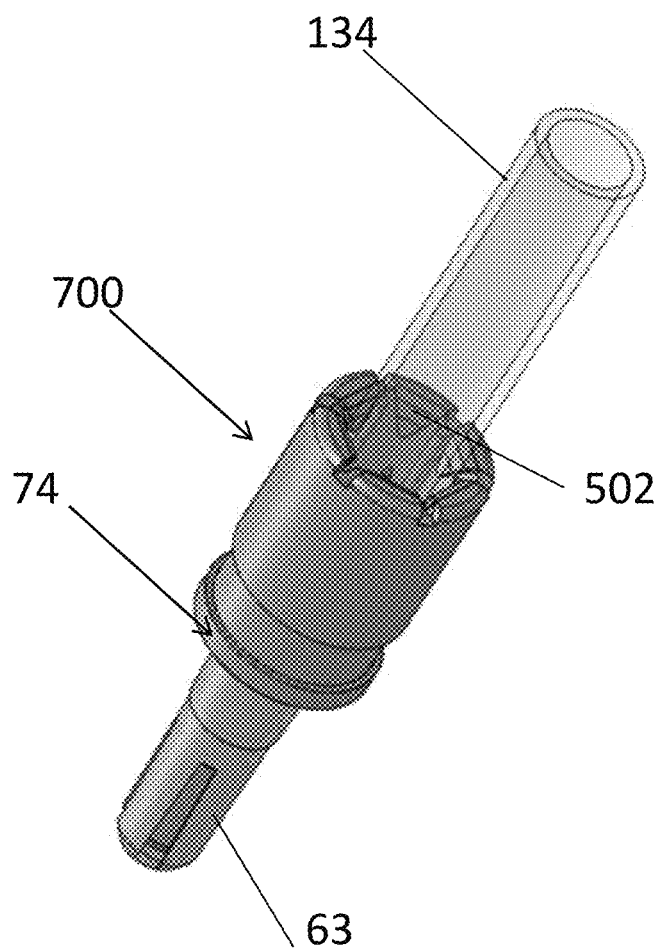
Figure 54A:
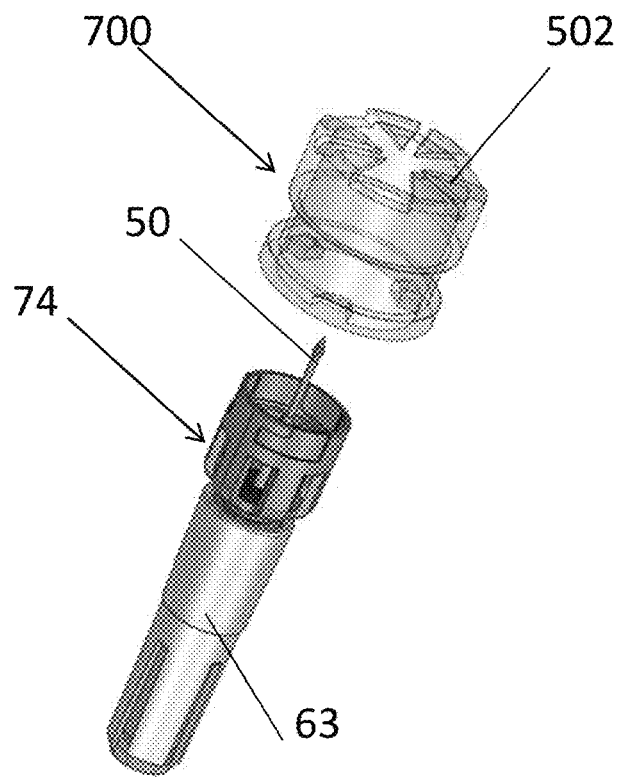
Figure 54B:
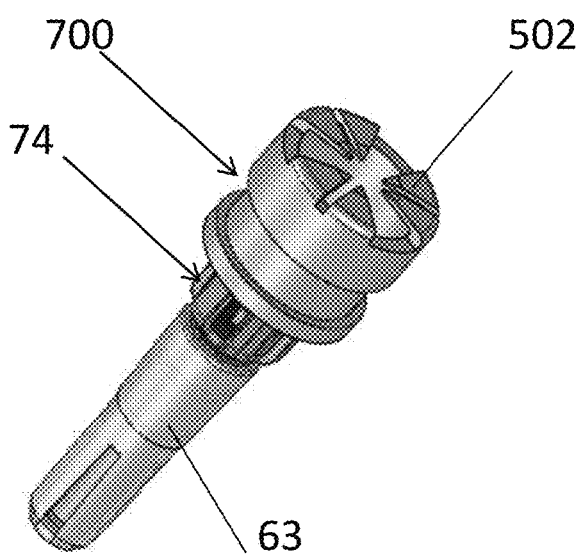
Figure 55:
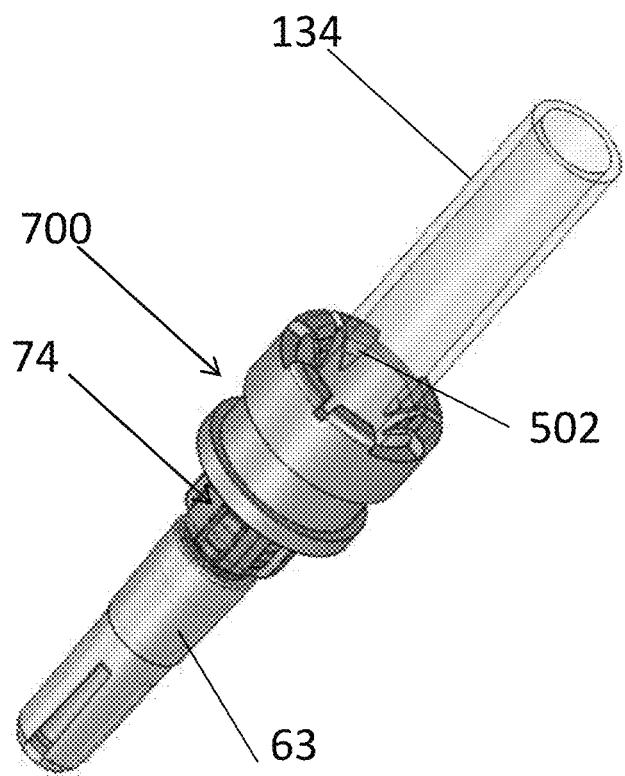

FIGS. 52A-60 depict a fourth embodiment of a needle proximal end protector (700). This needle proximal end protector (700) can either be formed (e.g., molded) as a part of a needle hub assembly (74) (see FIGS. 52A-53), or formed separately and coupled to a needle hub assembly (74) (see FIGS. 54A-55). In either embodiment, the proximal end of the needle proximal end protector (700) includes a plurality (e.g., six) of movable tabs (702) that are configured to prevent other components, such as needle cover members (63) of other needle hub assemblies (74) from entering the needle proximal end protector (700) and damaging the needle proximal end (50) of the needle hub assembly (74). The tabs (702) are also configured to bend inwardly when impinged upon by a cartridge (134) during assembly to allow the cartridge (134) to pass into the proximal end protector (700) and coupled to the needle hub assembly (74), as shown in FIGS. 53 and 55. The movable tabs (702) are functionally similar to the door (402) in the needle proximal end protector (500) in FIGS. 42A and 42B.

Figure 56:
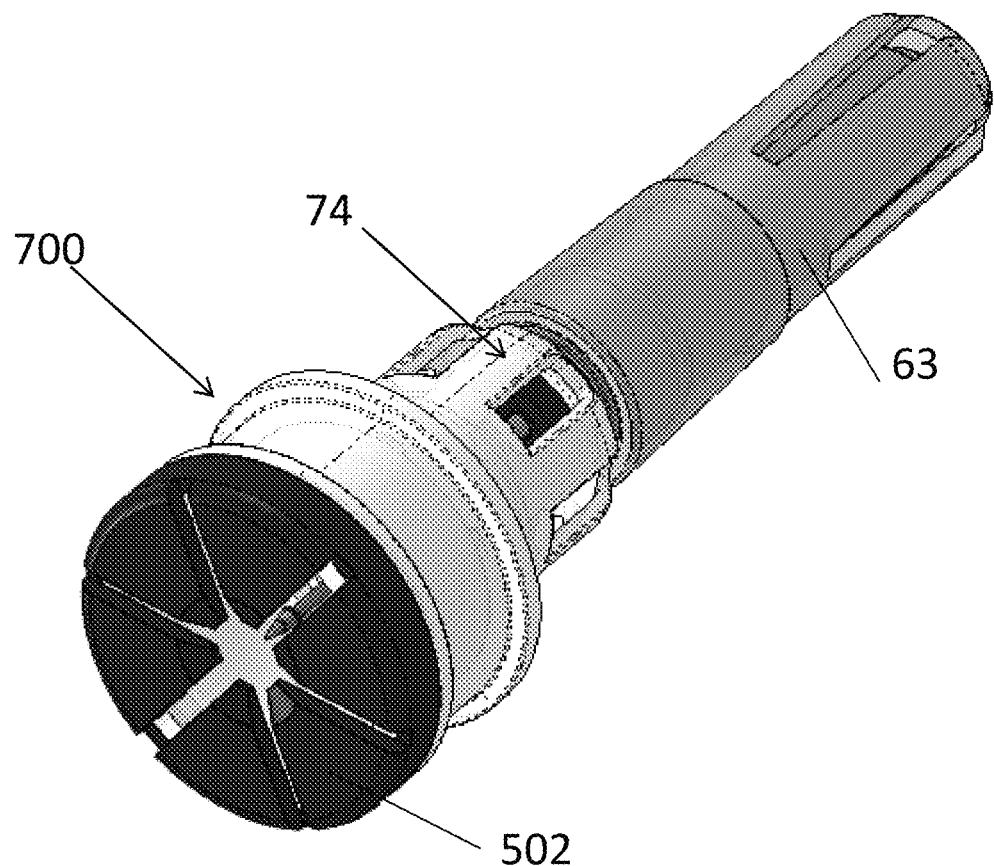
Figure 57:
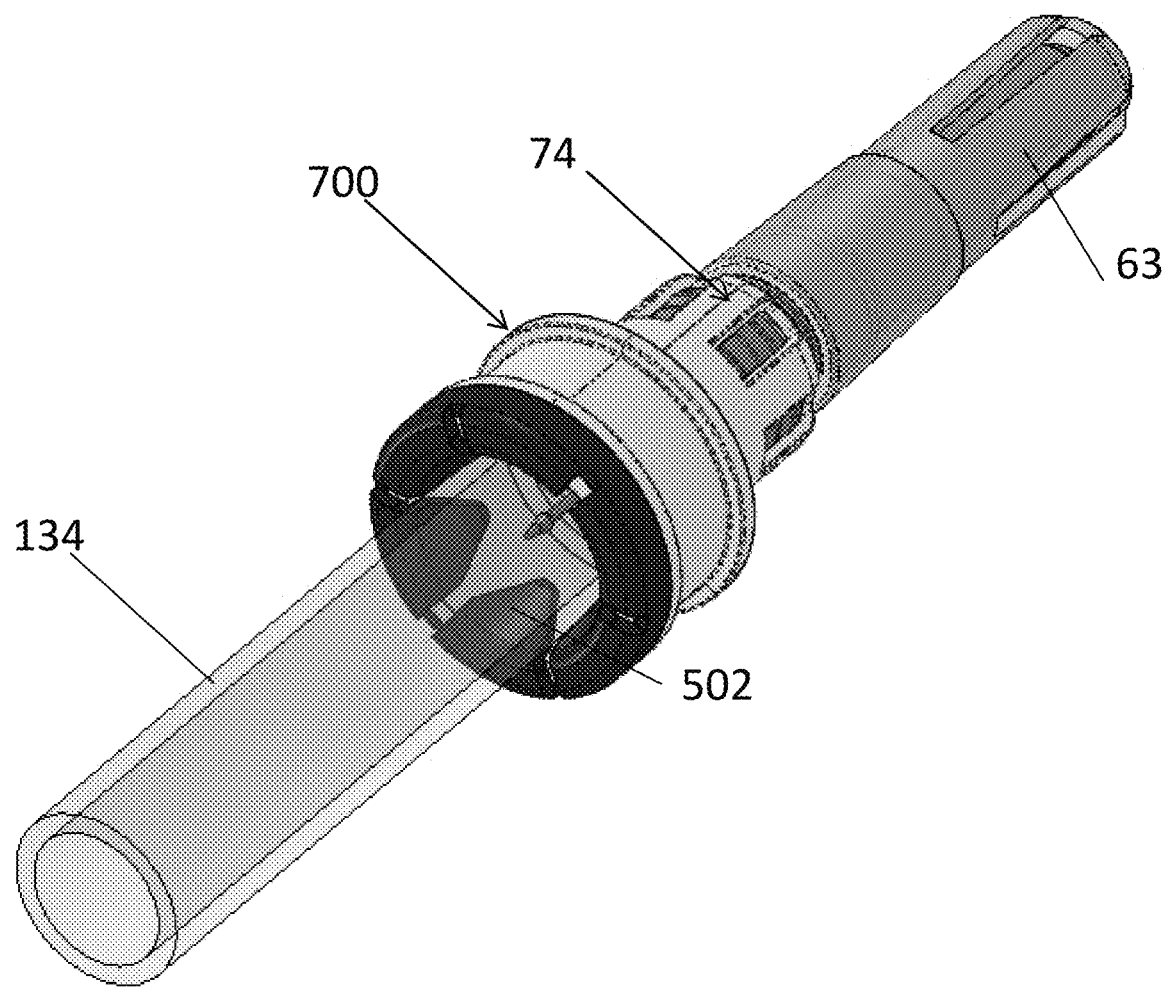
Figure 58A:
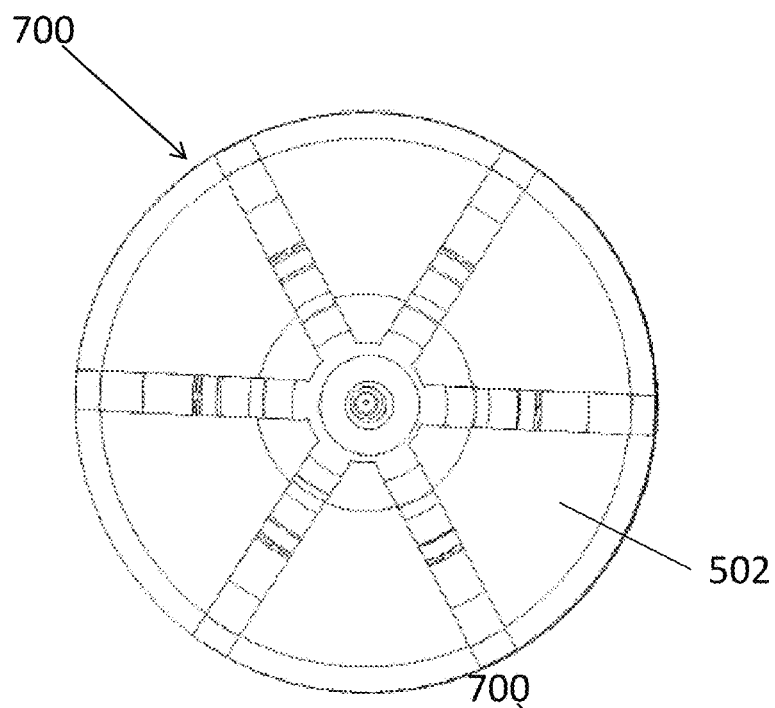
Figure 58B:
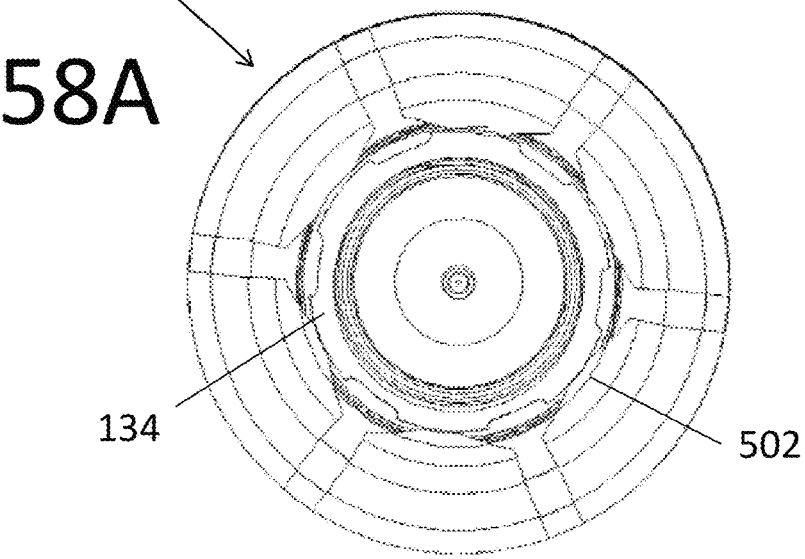
Figure 60:
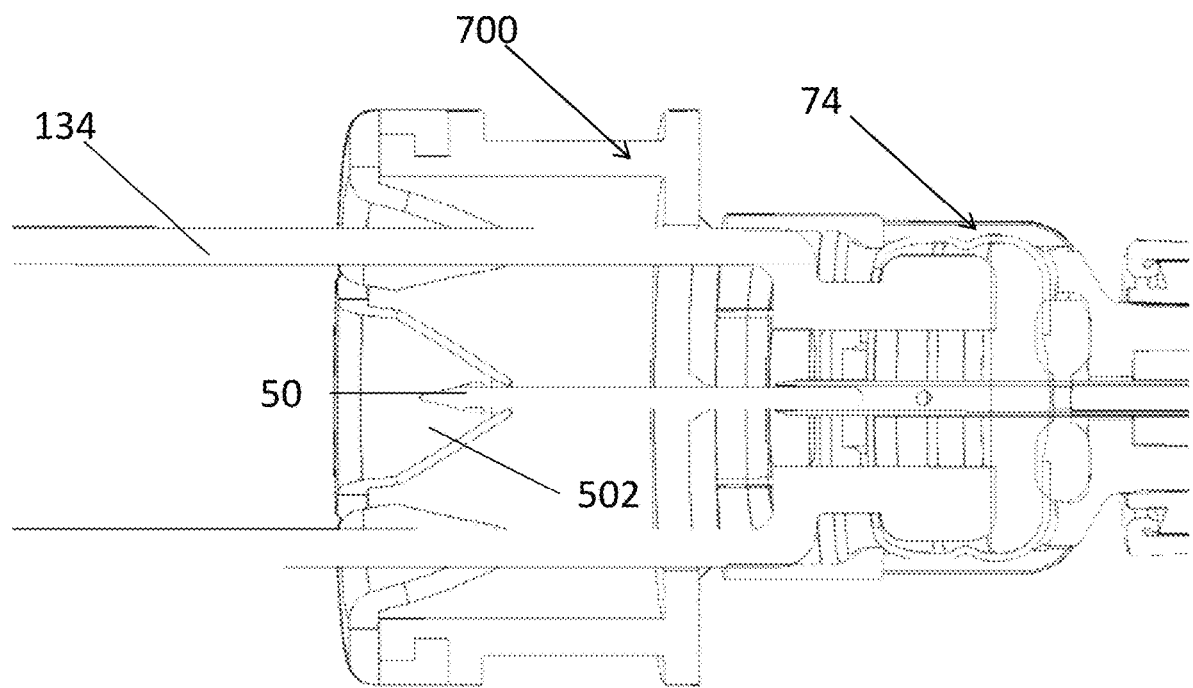

FIGS. 56 and 57 depicts the needle proximal end protector (700) shown from a perspective angle to demonstrate protection of the needle proximal end (50) by the tabs (702). FIGS. 58A and 58B depict the needle proximal end protector (700) from an axial view before and after a cartridge (134) is inserted to show the change in inner diameter of the needle proximal end protector (700) caused by insertion of the cartridge (134). FIGS. 59A-59C depict the needle proximal end protector (700) in a longitudinal cross-sectional view before and after a cartridge (134) is inserted to show the bending of the tabs (702) by insertion of the cartridge (134).

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, PTFE, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element-irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A system for injecting, comprising:
a cartridge body having proximal and distal openings, and a distal cartridge body interface;
a distal cartridge seal coupled to the distal cartridge body interface of the cartridge body;
a stopper member disposed in a cartridge interior of the cartridge body;
a plunger member having a plunger interior and configured to be manually manipulated to insert the stopper member relative to the cartridge body, the plunger member including
a needle retention feature disposed in the plunger interior,
an energy-storage member disposed in the plunger interior, and
an energy-storage member latching member disposed in the plunger interior;
a needle hub assembly coupled to the distal cartridge body interface of the cartridge body, the needle hub assembly including
a needle having a needle proximal end feature,
a hub, and
a needle latching member configured to selectively prevent the needle from moving proximally relative to the hub;
a needle hub seal disposed around the needle within the needle hub assembly, wherein the needle hub seal is configured to form a fluid tight seal between the hub, the needle, and the distal cartridge seal,
wherein manipulating the plunger member relative to the cartridge body to transform the energy-storage member latching member from a latched state to an unlatched state retracts the needle proximal end feature proximally through the stopper member,
wherein the hub comprises a snap over interface configured to couple the needle hub assembly to the distal cartridge body interface of the cartridge body,
wherein the snap over interface comprises a skirt, and the distal cartridge body interface comprises a flange, and
wherein the skirt extends proximally beyond the distal cartridge body interface when the needle hub assembly is coupled to the distal cartridge body interface, thereby reducing movement of the needle hub assembly relative to the cartridge body.

2. The system of claim 1, wherein the skirt comprises an expandable proximal portion configured to interface with the flange to couple the needle hub assembly to the distal cartridge body interface of the cartridge body, wherein the expandable proximal portion is biased in an unexpanded state, wherein inserting the flange through the expandable proximal portion elastically expands a proximal ring to allow the flange to move distally past the expandable proximal portion.

3. The system of claim 1, wherein the needle proximal end feature is configured to pierce the distal cartridge seal, thereby forming a fluid tight seal between an interior of the cartridge body and an exterior of the needle.

4. The system of claim 1, wherein the hub of the needle hub assembly is configured to substantially enclose the distal cartridge seal when the needle hub assembly is coupled to the distal cartridge body interface.

5. The system of claim 1, further comprising a second needle hub seal disposed in the needle hub assembly, wherein a proximal portion of the second needle hub seal is configured to be inserted into the distal opening in the cartridge body, thereby forming a fluid tight seal between the proximal portion of the second needle hub seal and the distal cartridge body interface of the cartridge body.

6. The system of claim 1, wherein the hub is configured stabilize the needle extending therethrough to facilitate insert of the needle proximal end feature through the distal opening of the cartridge body and into the cartridge interior.

7. The system of claim 1, wherein the needle hub seal is also configured to prevent contaminants from contacting an exterior surface of the needle.

8. The system of claim 1, wherein the needle hub seal is also configured to stabilize the needle passing therethrough.

9. The system of claim 1, the needle hub seal comprising a rigid substrate and a flexible gasket disposed thereon.

10. The system of claim 1, wherein the needle hub seal is configured to center the needle.

11. The system of claim 1, wherein the needle proximal end feature is configured to pass through the needle hub seal, thereby forming a fluid tight seal between an interior of the needle hub seal and an exterior of the needle.

12. The system of claim 1, wherein the needle hub seal is distal to the distal cartridge seal.

13. The system of claim 1, wherein the needle hub seal abuts the distal cartridge seal.

14. The system of claim 1, wherein the needle hub seal has a proximal state in the needle hub assembly, wherein the needle hub seal is configured to increase a force required to move the needle distally, and a distal state in the needle hub assembly, wherein the needle hub seal is configured to have a minimal effect on the force required to move the needle distally.

15. The system of claim 14, wherein moving the cartridge body into the needle hub assembly moves the needle hub seal from the proximal state to the distal state.

16. The system of claim 1, the needle hub seal comprising concentric inner and outer gaskets disposed about a portion of the needle.

17. The system of claim 16, wherein the inner gasket forms a fluid tight seal around the portion of the needle.

18. The system of claim 16, wherein the outer gasket forms a first fluid tight seal between the needle hub seal and the distal cartridge body interface of the cartridge body, and a second fluid tight seal between the needle hub seal and the hub.

* * * * *